(12) United States Patent
Clark et al.

(10) Patent No.: US 6,849,627 B2
(45) Date of Patent: Feb. 1, 2005

(54) 6,7-DIHYDRO-5H-PYRAZOLO[1,2-A] PYRAZOL-1-ONES WHICH CONTROL INFLAMMATORY CYTOKINES

(75) Inventors: Michael Philip Clark, Loveland, OH (US); Matthew John Laufersweiler, Morron, OH (US); Adam Golebiowski, Loveland, OH (US); Mark Sabat, Loveland, OH (US); Todd Andrew Brugel, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 74 days.

(21) Appl. No.: 10/390,216

(22) Filed: Mar. 17, 2003

(65) Prior Publication Data
US 2004/0038971 A1 Feb. 26, 2004

Related U.S. Application Data

(63) Continuation-in-part of application No. 10/246,214, filed on Sep. 18, 2002, now Pat. No. 6,730,668.
(60) Provisional application No. 60/323,625, filed on Sep. 20, 2001.

(51) Int. Cl.[7] .................. C07D 403/04; C07D 403/14; A61K 31/501
(52) U.S. Cl. ..................... 514/245; 514/275; 544/212; 544/296; 544/331
(58) Field of Search .................. 514/242, 245, 514/275; 544/182, 212, 296, 331

(56) References Cited

U.S. PATENT DOCUMENTS

| 3,449,359 A | 6/1969 | Testa et al. | |
| 2003/0134867 A1 * | 7/2003 | Clark et al. | 514/275 |

FOREIGN PATENT DOCUMENTS

| CH | 529153 A | 10/1972 | |
| WO | WO 01/57042 A2 | 8/2001 | |
| WO | WO 03/024971 A1 | 3/2003 | |
| WO | WO 03/023971 A1 * | 3/2004 | |

OTHER PUBLICATIONS

Illei, G. G. et al., "Novel, non–antigen–specific therapeutic approaches to autoimmune/inflammatory diseases", *Current Opinion in Immunology*, 2000, vol. 12, Issue 6, pp. 712–718.

Black, R. A. et al., "Agents that Block TNF–αSynthesis or Activity", *Annual Reports in Medicinal Chemistry–32*, Chapter 24, Academic Press, Inc., 1997, pp. 241–250.

U.S. Appl. No. 10/246,214, Michael Philip Clark et al., filed Sep. 18, 2002.

* cited by examiner

*Primary Examiner*—Thomas McKenzie
(74) *Attorney, Agent, or Firm*—Richard S. Echler, Sr.

(57) ABSTRACT

The present invention relates to compounds which are capable of preventing the extracellular release of inflammatory cytokines, said compounds, including all enantiomeric and diasteriomeric forms and pharmaceutically acceptable salts thereof, have the formula:

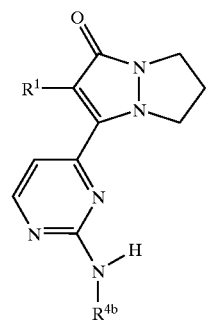

wherein $R^1$ is substituted aryl; $R^4$ is substituted or unsubstituted aryl or heteroaryl.

17 Claims, No Drawings

6,7-DIHYDRO-5H-PYRAZOLO[1,2-A] PYRAZOL-1-ONES WHICH CONTROL INFLAMMATORY CYTOKINES

CROSS REFERENCE TO RELATED APPLICATIONS

This application in a Continuation-In-Part Application of application Ser. No. 10/246,214 filed Sep. 18, 2002, now U.S. Pat. No. 6,730,668 issued May 4, 2004, which claims priority under Title 35, United States Code 119(e) from Provisional Application Ser No. 60/323,625, filed Sep. 20, 2001.

FIELD OF THE INVENTION

The present invention relates to 6,7-dihydro-5H-pyrazolo [1,2a]pyrazol-1-ones which inhibit the extracellular release of inflammatory cytokines, said cytokines responsible for one or more human or higher mammalian disease states. The present invention further relates to compositions comprising said 6,7-dihydro-5H-pyrazolo[1,2a]pyrazol-1-ones and method for preventing, abating, or otherwise controlling enzymes which are understood to be the active components responsible for the herein described disease states.

BACKGROUND OF THE INVENTION

Interleukin-1 (IL-1) and Tumor Necrosis Factor-□ (INF-□) are among the important biological substances known collectively as "cytokines." These molecules are understood to mediate the inflammatory response associated with the immunological recognition of infectious agents.

These pro-inflammatory cytokines are suggested as an important mediators in many disease states or syndromes, inter alia, rheumatoid arthritis, osteoarthritis, inflammatory bowel disease (IBS), septic shock, cardiopulmonary dysfunction, acute respiratory disease, cachexia, and therefore responsible for the progression and manifestation of human disease states.

There is therefore a long felt need for compounds and pharmaceutical compositions which comprise compounds, which can block, abate, control, mitigate, or prevent the release of cytokines from cells which produce them.

SUMMARY OF THE INVENTION

The present invention meets the aforementioned needs in that it has been surprisingly found that certain bicyclic pyrazolones and derivatives thereof are effective for inhibiting release of inflammatory cytokines, inter alia, interleukin-1 (IL-1) and tumor necrosis factor (TNF) from cells and thereby preventing, abating, or otherwise controlling enzymes which are proposed to be the active components responsible for the herein described disease states.

The first aspect of the present invention relates to compounds, including all enantiomeric and diasteriomeric forms and pharmaceutically acceptable salts thereof, said compounds having the formula:

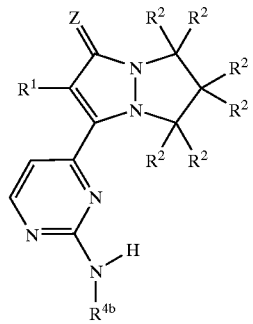

wherein $R^1$ is:
a) substituted or unsubstituted aryl; or
b) substituted or unsubstituted heteroaryl;

each $R^2$ unit is independently selected from the group consisting of:
a) hydrogen;
b) —$(CH_2)_jO(CH_2)_nR^8$;
c) —$(CH_2)_jNR^{9a}R^{9b}$;
d) —$(CH_2)_jCO_2R^{10}$;
e) —$(CH_2)_jOCO_2R^{10}$;
f) —$(CH_2)_jCON(R^{10})_2$;
g) —$(CH_2)_jOCON(R^{10})_2$;
h) two $R^2$ units can be taken together to form a carbonyl unit;
i) and mixtures thereof;

$R^8$, $R^{9a}$, $R^{9b}$, and $R^{10}$ are each independently hydrogen, $C_1$–$C_4$ alkyl, and mixtures thereof;

$R^{9a}$ and $R^{9b}$ can be taken together to form a carbocyclic or heterocyclic ring comprising from 3 to 7 atoms; two $R^{10}$ units can be take together to form a carbocyclic or heterocyclic ring comprising from 3 to 7 atoms; j is an index from 0 to 5, n is an index from 0 to 5;

Z is O, S, $NR^{11}$, or $NOR^{11}$; $R^{11}$ is hydrogen or $C_1$–$C_4$ alkyl $R^{4b}$ is substituted or unsubstituted aryl or substituted or unsubstituted heteroaryl.

Another aspect of the present invention relates to pharmaceutical compositions which can deliver the compounds of the present invention to a human or higher mammal, said compositions comprising:
a) an effective amount of one or more of the compounds according to the present invention; and
b) one or more pharmaceutically acceptable excipients.

A further aspect of (he present invention relates to methods for controlling one or more inflammatory cytokine mediated or inflammatory cytokine modulated mammalian diseases or conditions, said method comprising the step of administering to a human or higher mammal and effective amount of a composition comprising one or more of the compounds according to the present invention.

Another aspect of the present invention relates to forms of the compounds of the present invention, which under normal physiological conditions, will release the compounds as described herein.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The present invention relates to compounds which are capable of mediating, controlling or otherwise inhibiting the extracellular release of certain cytokines, especially inflammatory cytokines, said cytokines playing a role in the stimulation, cause or manifestation of a wide variety of diseases, disease states, or syndromes.

For the purposes of the present invention the term "hydrocarbyl" is defined herein as any organic unit or moiety which is comprised of carbon atoms and hydrogen atoms. Included within the term hydrocarbyl are the heterocycles which are described herein below. Examples of various unsubstituted non-heterocyclic hydrocarbyl units include pentyl, 3-ethyloctanyl, 1,3-dimethylphenyl, cyclohexyl, cis-3-hexyl, 7,7-dimethylbicyclo[2.2.1]-heptan-1-yl, and naphth-2-yl.

Included within the definition of "hydrocarbyl" are the aromatic (aryl) and non-aromatic carbocyclic rings, non-limiting examples of which include cyclopropyl, cyclobutanyl, cyclopentanyl, cyclohexane, cyclohexenyl, cycloheptanyl, bicyclo-[0.1.1]-butanyl, bicyclo-[0.1.2]-pentanyl, bicyclo-[0.1.3]-hexanyl (thujanyl), bicyclo-[0.2.2]-hexanyl, bicyclo-[0.1.4]-heptanyl (caranyl), bicyclo-[2.2.1]-heptanyl (norboranyl), bicyclo-[0.2.4]-octanyl (caryophyllenyl), spiropentanyl, diclyclopentanespiranyl, decalinyl, phenyl, benzyl, naphthyl, indenyl, 2H-indenyl, azulenyl, phenanthryl, anthryl, fluorenyl, acenaplitiylenyl, 1,2,3,4-tetrahydronaphthalenyl, and the like.

The term "heterocycle" includes both aromatic (heteroaryl) and non-aromatic heterocyclic rings non-limiting examples of which include: pyrrolyl, 2H-pyrrolyl, 3H-pyrrolyl, pyrazolyl, 2H-imidazolyl, 1,2,3-triazolyl, 1,2,4-triazolyl, isoxazolyl, oxazoyl, 1,2,4-oxadiazolyl, 2H-pyranyl, 4H-pyranyl, 2H-pyran-2-one-yl, pyridinyl, pyridazinyl, pyrimidinyl, pyrazinyl, piperazinyl, s-triazinyl, 4H-1,2-oxazinyl, 2H-1,3-oxazinyl, 1,4-oxazinyl, morpholinyl, azepinyl, oxcpinyl, 4H-1,2-diazepinyl, indenyl 2H-indenyl, benzofuranyl, isobenzofuranyl, indolyl, 3H-indolyl, 1H-indolyl, benzoxazolyl, 2H-1-benzopyranyl, quinoliinyl, isoquinolinyl, quinazolinyl, 2H-1,4-benzoxazinyl, pyrrolidinyl, pyrrolinyl, quinoxalinyl, furanyl, thiophenyl, benzimidazolyl, and the like each of which can be substituted or unsubstituted.

An example of a unit defined by the term "alkylenearyl" is a benzyl unit having the formula:

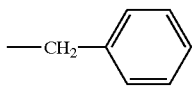

whereas an example of a unit defined by the term "alkyleneheteroaryl" is a 2-picolyl unit having the formula:

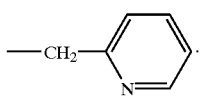

The term "substituted" is used throughout the specification. The term "substituted" is defined herein as "encompassing moieties or units which can replace a hydrogen atom, two hydrogen atoms, or three hydrogen atoms of a hydrocarbyl moiety. Also substituted can include replacement of hydrogen atoms on two adjacent carbons to form a new moiety or unit." For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. An epoxide unit is an example of a substituted unit which requires replacement of a hydrogen atom on adjacent carbons. The term substituted is used throughout the present specification to indicate that a hydrocarbyl moiety, inter alia, aromatic ring, alkyl chain, can have one or more of the hydrogen atoms replaced by a substituent. When a moiety is described as "substituted" any number of the hydrogen atoms may be replaced. For example, 4-hydroxyphenyl is a "substituted aromatic carbocyclic ring". (N,N-dimethyl-5-amino)octanyl is a "substituted $C_8$ alkyl unit, 3-guanidinopropyl is a "substituted $C_3$ alkyl unit," and 2-carboxypyridinyl is a "substituted heteroaryl unit." The following are non-limiting examples of units which can serve as a replacement for hydrogen atoms when a hydrocarbyl unit is described as "substituted."

i) —$[C(R^{12})_2]_p(CH=CH)_qR^{12}$; wherein p is from 0 to 12; q is from 0 to 12;
ii) —$C(Z)R^{12}$;
iii) —$C(Z)_2R^{12}$;
iv) —$C(Z)CH=CH_2$;
V) —$C(Z)N(R^{12})_2$;
vi) —$C(Z)NR^{12}N(R^{12})_2$;
vii) —CN;
viii) —CNO;
ix) —$CF_3$, —$CCl_3$, —$CBr_3$;
Z) —$N(R^{12})_2$;
xi) —$NR^{12}CN$;
xii) —$NR^{12}C(Z)R^{12}$;
xiii) —$NR^{12}C(Z)N(R^{12})_2$;
xiv) —$NHN(R^{12})_2$;
xv) —$NHOR^{12}$;
xvi) —NCS;
xvii) —$NO_2$;
xviii) —$OR^{12}$;
xix) —OCN;
xx) —$OCF_3$, —$OCCl_3$, —$OCBr_3$;
xxi) —F, —Cl, —Br, —I, and mixtures thereof;
xxii) —SCN;
xxiii) —$SO_3M$;
xxiv) —$OSO_3M$;
xxv) —$SO_2N(R^{12})_2$;
xxvi) —$SO_2R^{12}$;
xxvii) —$P(O)H_2$;
xxviii) —$PO_2$;
xxix) —$P(O)(OH)_2$;
xxx) and mixtures thereof;

wherein $R^{12}$ is hydrogen, substituted or unsubstituted $C_1$–$C_{20}$ linear, branched, or cyclic alkyl, $C_6$–$C_{20}$ aryl, $C_7$–$C_{20}$ alkylenearyl, and mixtures thereof, M is hydrogen, or a salt forming cation; Z is =O, =S, =$NR^{11}$, and mixtures thereof. Suitable salt forming cations include, sodium, lithium, potassium, calcium, magnesium, ammonium, and the like.

The first aspect of the present invention relates to compounds having the formula:

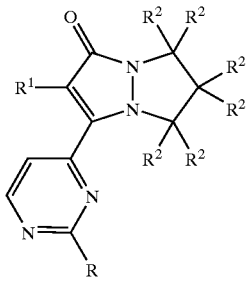

which are 2-R¹-substituted-3-(2-R-substituted-pyrimidin4-yl)-6,7-dihydro-5H-pyrazolo[1,2a]pyrazol-1-ones.

The second aspect of the present invention relates to compounds having the formula:

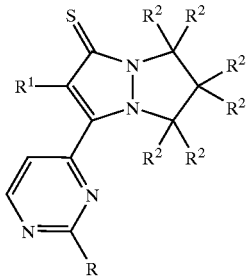

which are 2-R¹substituted-3-(2-R-substituted-pyrimidin-4-yl)-6,7-dihydro-5H-pyrazolo[1,2a]pyrazol-1-thiones.

The third aspect of the present invention relates to compounds having the formula:

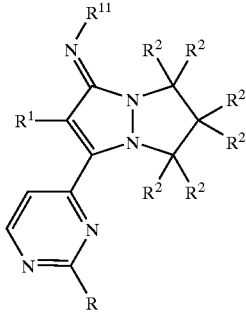

which are 2-R¹substituted-3-(2-R-substituted-pyrimidin4-yl)-6,7-dihydro-5H-pyrazolo[1,2a]pyrazol-1-ylideneamines and derivatives thereof.

R is a substituent at the 2-position of the pyrimidin4-yl portion of the general scaffold, said R unit is:
 a) an ether having the formula —O[CH$_2$]$_k$R$^3$; or
 b) a primary or secondary amino unit having the formula —NR$^{4a}$R$^{4b}$;
wherein R$^3$ is substituted or unsubstituted C$_1$–C$_4$ alkyl, substituted or unsubstituted cyclic hydrocarbyl, substituted or unsubstituted heterocyclyl, substituted or unsubstituted aryl or alkylenearyl, substituted or unsubstituted heteroaryl or alkyleneheteroaryl; the index k is from 0 to 5.

The following are the various aspects of R units according to the present invention wherein R is an ether having the formula —O[CH$_2$]$_k$R$^3$. However, the formulator is not limited to the herein exemplified iterations and examples.

A) R units encompassing ethers having the formula —OR$^3$ (the index k equal to 0) and R$^3$ is substituted or unsubstituted aryl.
 i) One iteration of this aspect of R comprises ethers having the formula —OR$^3$ and R$^3$ is substituted or unsubstituted aryl. This iteration includes the following non-limiting example of R: phenoxy, 2-fluorophenoxy, 3-fluorophenoxy, 4-fluorophenoxy, 2,4-difluorophenoxy, 3-trifluoromethylphenoxy, 4-trifluoromethylphenoxy, 2,4-trifluoromethyl phenoxy, and the like.
 ii) Another iteration of this aspect of R comprises ethers having the formula —OR$^3$ and R$^3$ is substituted or unsubstituted aryl. This iteration includes the following non-limiting examples: 2-methylphenoxy, 3-methylphenoxy, 4-methylphenoxy, 2,4-dimethylphenoxy, 2-cyanophenoxy, 3-cyanophenoxy, 4cyanophenoxy, 4-ethylphenoxy, and the like.
 iii) A further iteration of this aspect of R comprises ethers having the formula —OR$^3$ and R$^3$ is substituted or unsubstituted aryl. This iteration includes the following non-limiting examples: (2-methyoxy)phenoxy, (3-methoxy)phenoxy, (4-methoxy)phenoxy, 3-[(N-acetyl)amino]phenoxy, 3-benzo[1,3]dioxol-5-yl, and the like.

B) R units encompassing ethers having the formula —OR$^3$ (the index k equal to 0) and R$^3$ is substituted or unsubstituted heteroaryl.
 i) A first iteration of this aspect of R comprises ethers having the formula —OR$^3$ and R$^3$ is unsubstituted heteroaryl. This iteration includes the following non-limiting examples: pyrimidin-2-yl, pyrimidin4-yl, pyridin-2-yl, pyridin-3-yl, pyridin4-yl, and the like.
 ii) A second iteration of this aspect of R comprises ethers having the formula —OR$^3$ and R$^3$ is substituted heteroaryl. This iteration includes the following non-limiting examples: 2-aminopyrimidin4-yl, and the like.

C) R units encompassing ethers having the formula —OCH$_2$R$^3$ (the index k equal to 1) and R$^3$ is substituted or unsubstituted aryl.
 i) A first iteration of this aspect of R comprises ethers having the formula —OCH$_2$R$^3$ and R$^3$ is substituted or unsubstituted heteroaryl. This iteration includes the following non-limiting examples: pyrimidin-2-yl, pyrimidin-4-yl, 2-aminopyrimidin-4-yl, 4-aminopyrimidin-6-yl, pyridin-2-yl, pyridin-3-yl, pyridin-4-yl, and the like. p1 ii) A second iteration of this aspect of R wherein R is an ether having the formula —OCH$_2$R$^3$ and R$^3$is substituted or unsubstituted alkyleneheteroaryl-aryl. This iteration includes the following non-limiting examples: pyridin-3-ylethyl, (2-methyl-2-pyridin-3-yl)ethyl, and the like.

D) R units encompassing ethers having the formula —OR$^3$ (the index k equal to 1) and R$^3$ is R$^3$ is substituted or unsubstituted C$_1$–C$_4$ alkyl.
 i) A first iteration of this aspect of R is an ether having the formula —OR$^3$ and R$^3$ is unsubstituted C$_1$–C$_4$ linear, branched, or cyclic alkyl. This iteration includes the following non-limiting examples: methyl, ethyl, isopropyl, (S)-1-methypropyl, and the like.
 ii) A second iteration of this aspect of R is an ether having the formula —OR$^3$ and R$^3$ is a substituted C$_1$–C$_4$ linear, branched, or cyclic alkyl. This iteration includes the following non-limiting examples: 2-methoxyethyl, (S)-1-methy-3-methyoxypropyl, and the like.

The following are the various aspects of R units according to the present invention wherein R is an amine having the formula —NR$^{4a}$R$^{4b}$, R$^{4a}$ and R$^{4b}$ are each independently:
a) hydrogen; or
b) —[C(R$^{5a}$R$^{5b}$)]$_m$R$^6$;
each R$^{5a}$ and R$^{5b}$ are independently hydrogen, or C$_1$–C$_4$ linear, branched, —OR$^7$, —N(R$^7$)$_2$, —CO$_2$R$^7$, —CON(R$^7$)$_2$; cyclic alkyl, and mixtures thereof, R$^6$ is hydrogen, substituted or unsubstituted C$_1$–C$_4$ alkyl, substituted or unsubstituted heterocyclic, substituted or unsubstituted aryl, or substituted or unsubstituted heteroaryl; —OR$^7$, —N(R$^7$)$_2$, —CO$_2$R$^7$, —CON(R$^7$)$_2$, R$^7$is hydrogen, a water-soluble cation, C$_1$–C$_4$ alkyl, or substituted or unsubstituted aryl; the index m is from 0 to 5. However, the formulator is not limited to the herein exemplified iterations and examples.

A) R units encompassing chiral amino groups wherein R$^{4a}$ is hydrogen, R$^{5a}$ is hydrogen and R$^{5b}$ is methyl, said units having the formula:

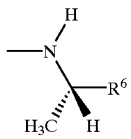

and the indicated stereochemistry.
i) A first iteration of this aspect of R is an amine comprising an R$^6$ which is substituted or unsubstituted phenyl. This iteration includes the following non-limiting examples: (S)-1-methyl-1-phenylmethylamino, (S)-1-methyl-1-(4-fluorophenyl)methylamino, (S)-1-methyl-1-(4-methylphenyl)methyl-amino, (S)-1-methyl-1-(4-methoxyphenyl)methylamino, (S)-1-methyl-1-(2-aminophenyl)methylamino, (S)-1-methyl-1-(4-aminophenyl)methylamino, and the like.
ii) A second iteration of this aspect of R is an amine comprising an R$^6$ which is substituted or unsubstituted heteroaryl. This iteration includes the following non-limiting examples: (S)-1-methyl-1-(pyridin-2-yl)methylamino, (S)-1-methyl-1-(pyridin-3-yl)methylamino, (S)-1-methyl-1-(pyridin4-yl)methylamino, (S)-1-methyl-1-(furan-2-yl)methylamino, (S)-1-methyl-1-(3-benzol[_b 1,3]dioxol-5-yl)methylamino, and the like.
iii) A third iteration of this aspect of R is an amine comprising an R$^6$ which is C$_1$–C$_4$ substituted or unsubstituted alkyl. This iteration includes the following non-limiting examples: (S)-1-methylpropylamino, (S)-1-methyl-2-(methoxy)ethylamino.

B) R units encompassing chiral amino groups wherein R$^{4a}$ is hydrogen, R$^{5a}$ and R$^{5b}$ are each C$_1$–C$_4$ alkyl, said units having the formula:

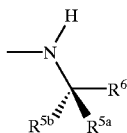

and the indicated stereochemistry when R$^{5a}$, R$^{5b}$ and R$^6$ are not the same.
i) A first iteration of this aspect of R is an amine which does not have a chiral center, non-limiting examples of which includes 1,1-dimethylethylamine, 1,1-dimethylbenzylamine and the like.
ii) A second iteration of this aspect of R is an amine comprising an R$^6$ which is substituted or unsubstituted C$_1$–C$_4$ alkyl. This iteration includes the following non-limiting examples: (S)-1-methyl-2-hydroxy-2-methylpropylamine, (S)-1-methyl-2-hydroxy-2-methylbutylamine, and the like.

C) R units encompassing alkylenearyl amines wherein R$^{4a}$ is hydrogen, both R$^{5a}$ and R$^{5b}$ of R$^{4b}$ are hydrogen. R$^6$ is substituted or unsubstituted aryl, said unit having the formula:

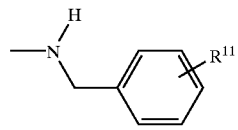

wherein R$^{11}$ is hydrogen or a "substituted unit" as defined herein above.
i) A first iteration of this aspect comprises the following non-limiting examples of R units: benzylamino, (2-aminophenyl)methylamino; (4-fluorophenyl)methylamino, (4-methoxyphenyl)methylamino; (4-propanesulfonylphenyl)methylamino; and the like.
ii) A second iteration of this aspect comprises the following non-limiting examples of R units: (2-methylphenyl)methylamino; (3-methylphenyl)-methylamino; (4-methylphenyl)methylamino; and the like.

D) K units encompassing amines wherein R$^{4a}$ is hydrogen, R$^{4b}$ comprises R$^{5a}$ equal to hydrogen and R$^{5b}$ equal to —CO$_2$R$^7$ or —CON(R$^7$)$_2$; said unit having the formula:

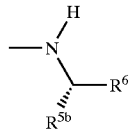

i) A first iteration of this aspect of R is an amine comprising an R$^6$ which is substituted or unsubstituted phenyl. This iteration includes the following non-limiting examples:

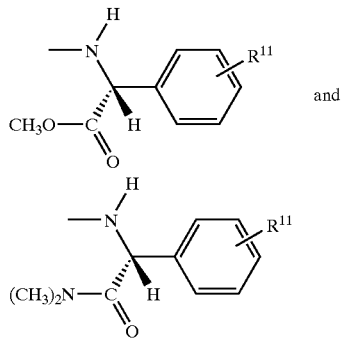

wherein R$^{11}$ is hydrogen or a "substitute" as defined herein above.
ii) A second iteration of this aspect of R is an amine comprising an R$^6$ which is substituted or unsubstituted alkyl. This iteration includes the following non-limiting examples:

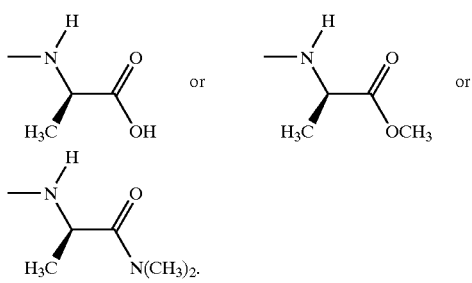
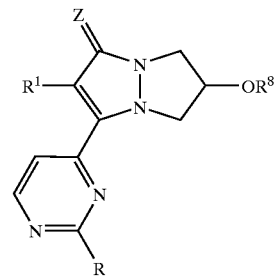

$R^1$ units are selected from:
a) substituted or unsubstituted aryl; or
b) substituted or unsubstituted heteroaryl.

A The first aspect of $R^1$ units encompasses halogen substituted phenyl units, non-limiting examples of which include 4-fluorophenyl, 2,4-difluorophenyl, 4-chlorophenyl, and the like.

Each $R^2$ unit is independently selected from the group consisting of:
a) hydrogen;
b) $-(CH_2)_jO(CH_2)_nR^8$;
c) $-(CH_2)_jNR^{9a}R^{9b}$;
d) $-(CH_2)_jCO_2R^{10}$;
e) $-(CH_2)_jOCO_2R^{10}$;
f) $-(CH_2)_jCON(R^{10})_2$;
g) $-(CH_2)_jOCON(R^{10})_2$;
h) two $R^2$ units can be taken together to form a carbonyl unit;
i) and mixtures thereof, $R^8$, $R^{9a}$, $R^{9b}$, and $R^{10}$ are each independently hydrogen, $C_1$–$C_4$ alkyl, and mixtures thereof; $R^{9a}$ and $R^{9b}$ can be taken together to form a carbocyclic or heterocyclic ring comprising from 3 to 7 atoms; two $R^{10}$ units can be take together to form a carbocyclic or heterocyclic ring comprising from 3 to 7 atoms; j is an index from 0 to 5, n is an index from 0 to 5.

The first aspect of the present invention relating to $R^2$ encompasses scaffolds having the formula:

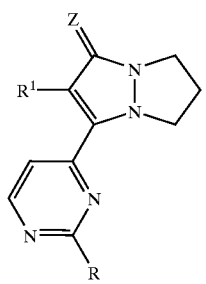

wherein each $R^2$ unit is hydrogen.

A second aspect relates to scaffolds having the formula:

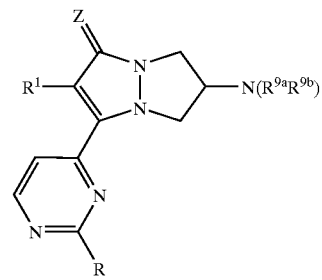

wherein $R^8$ is hydrogen or $C_1$–$C_4$ alkyl.

A third aspect relates to scaffolds having the formula:

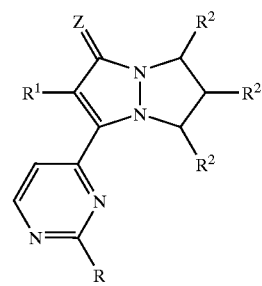

wherein $R^{9a}$ and $R^{9b}$ are each independently hydrogen, methyl, or $R^{9a}$ and $R^{9b}$ can be taken together to form a piperidine or morpholine ring.

A fourth aspect relates to scaffolds having the formula:

wherein one $R^2$ is $-CO_2R^{10}$ and the other $R^2$ units are hydrogen; one $R^{10}$ is hydrogen or methyl.

Z is O, S, $NR^{11}$, or $NOR^{11}$; $R^{11}$ is hydrogen or $C_1$–$C_4$ alkyl. The first aspect of the present invention as it relates to Z units, comprises oxygen atoms which provide 2-$R^1$substituted-3-(2-R-substituted-pyrimidin-4-yl)-6,7dihydro-5H-pyrazolo[1,2a]pyrazol-1-ones, the second aspect relates to Z units comprising sulfur atoms which provide 2-$R^1$ substituted-3-(2-R-substituted-pyrinidin-4-yl)-6,7-dihydro-5H-pyrazolo[1,2a]pyrazol-1-thiones, and the third aspect of the present invention as it relates to Z units, comprises $NR^{11}$ units thereby providing 2-$R^1$substituted-3-(2-R-substituted-pyrimidin-4-yl)6,7-dihydro-5H-pyrazolo[1,2a]pyrazol-1-ylideneamines and derivatives thereof.

The present invention relates to the surprising discovery that the compounds which comprise Category IV of the present invention have increased cytokine inhibition. The compounds which comprise the Category IV have the formula;

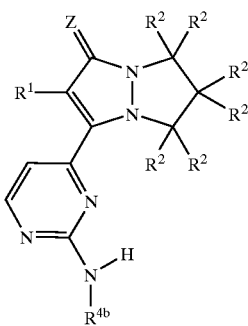

wherein $R^1$ is:

a) substituted or unsubstituted aryl; or b) substituted or unsubstituted heteroaryl;

each $R^2$ unit is independently selected from the group consisting of:
a) hydrogen;

b) $—(CH_2)_jO(CH_2)_nR^8$;

c) $—(CH_2)_jNR^{9a}R^{9b}$;

d) $—(CH_2)_jCO_2R^{10}$;

e) $—(CH_2)_jOCO_2R^{10}$;

f) $—(CH_2)_jCON(R^{10})_2$;

g) $—(CH_2)_jOCON(R^{10})_2$;

h) two $R^2$ units can be taken together to form a carbonyl unit;
i) and mixtures thereof;
$R^8$, $R^{9a}$, $R^{9b}$, and $R^{10}$ are each independently hydrogen, $C_1$–$C_4$ alkyl, and mixtures thereof; $R^{9a}$ and $R^{9b}$ can be taken together to form a carbocyclic or heterocyclic ring comprising from 3 to 7 atoms; two $R^{10}$ units can be take together to form a carbocyclic or heterocyclic ring comprising from 3 to 7 atoms; j is an index from 0 to 5, n is an index from 0 to 5;

Z is O, S, $NR^{11}$, or $NOR^{11}$; $R^{11}$ is hydrogen or $C_1$–$C_4$ alkyl $R^{4b}$ is substituted or unsubstituted aryl or substituted or unsubstituted heteroaryl.

The first and second aspects of Category IV relate to compounds having the formula:

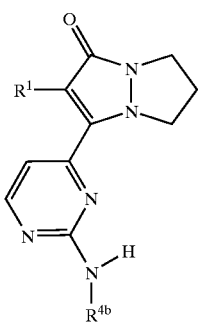

The first aspect of $R^1$ relates to substituted aryl units selected from 4-fluorophenyl, 3-fluorophenyl, 2,4-difluorophenyl, 4-chlorophenyl, 3-chlorophenyl, 2,4-chlorophenyl, or 3-trifluorophenyl. Two particular $R^1$ units which imbue efficacy in our hands against cytokine release includes 4-fluorophenyl and 3-trifluoromethylphenyl, particularly 4-fluorophenyl.

The first aspect of $R^4$ relates to substituted and unsubstituted aryl unit.

The first iteration of this aspect relates to an aryl unit or halogen substituted aryl unit selected from the group consisting of phenyl, 2-fluorophenyl, 3-fluorophenyl, 4-fluorophenyl, 2,4-difluorophenyl, 2,6-difluorophenyl, 3,5-difluorophenyl, 2,4,6-trifluorophenyl, 2-chlorophenyl, 3-chlorophenyl, 4-chlorophenyl, 2,4-dichlorophenyl, 2,6-dichlorophenyl, 3,5-dichlorophenyl, 2,4,6-trichlorophenyl, naphthylen-1-yl, and naphthylen-2-yl.

The second iteration of this aspect relates to a substituted aryl unit selected from the group consisting of 2-aminophenyl, 3-aminophenyl, 4-aminophenyl, 2-methylphenyl, 3-methylphenyl, 4-methylphenyl, 2,4-dimethylphenyl, 2-methoxyphenyl, 3-methoxyphenyl, 4-methoxyphenyl, 2-cyanophenyl, 3-cyanophenyl, and 4-cyanophenyl.

The third iteration of this aspect relates to a substituted aryl unit selected from the group consisting of 4-(methanesulfonyl)phenyl, 4-(ethanesulfonyl)phenyl 4-(propane-sulfonyl)phenyl, 2-(N-acylamino)phenyl, 3-(N-acylamino)phenyl, 4-(N-acylamino)phenyl, and 3-benzo[1, 3]dioxol-5-yl.

A fourth iteration of this aspect relates to an aryl unit selected from the group consisting of 2-trifluoromethylphenyl, 3-trifluoromethylphenyl, 4-trifluoromethylphenyl, and 3,5-bis(trifluoromethyl) phenyl.

The second aspect of $R^4$ relates to substituted and unsubstituted aryl unit.

The first iteration of this aspect relates to an aryl unit selected from the group consisting of 2-trifluoromethylphenyl, 3-trifluoromethylphenyl, 4-trifluoromethylphenyl, and 3,5-bis(trifluoromethyl) phenyl.

The second iteration of this aspect relates to a heteroaryl or substituted heteroaryl unit is selected from the group consisting of pyridin-2-yl, pyridin-3-yl, pyridin4-yl, pyrimidin-2-yl, pyrimidin4-yl, pyrimidin-5-yl, 4,6dichloropyrimidin-5-yl, and s-triazinyl.

Non-limiting examples of compounds of Category IV having the parent scaffold with the formula:

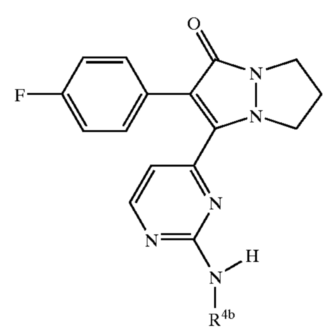

include:

2-(4-Fluorophenyl)-3-(2-phenylamino-pyrimidin-4-yl)-6, 7-dihydro-5H-pyrazolo[1,2-a]pyrazo-1-one;

3-[2-(2-Fluorophenylamino)-pyrimidin-4-yl]-2-(4-fluorophenyl)-6,7dihydro-5H-pyrazolo[1,2-a]pyrazol-1-one;

3-[2-(3-Fluorophenylamino)-pyrimidin-4-yl]-2-(4-fluorophenyl)6,7-dihydro-5H-pyrazolo[1,2-a]pyrazol-1-one;

3-[2-(4-Fluorophenylamino)-pyrimidin-4-yl] -2-(4-fluorophenyl)-6,7-dihydro-5H-pyrazolo[1,2-a]pyrazol-1-one;

3-[2-(2-Chlorophenylamino)-pyrimidin-4-yl]-2-(4-fluorophenyl)-6,7-dihydro-5H-pyrazolo[1,2-a]pyrazol-1-one;

3-[2-(3-Chlorophenylamino)-pyrimidin-4-yl ]-2-(4-fluorophenyl)6,7-dihydro-5H-pyrazolo[1,2-a]pyrazol-1-one;

3-[2-(4-Chlorophenylamino)-pyrimidin-4-yl]-2-(4-fluorophenyl)-6,7-dihydro-5H-pyrazolo[1,2-a]pyrazol-1-one;

3-[2-(2-Methylphenylamino)-pyrimidin-4-yl]-2-(4-fluorophenyl)-6,7-dihydro-5H-pyrazolo[1,2-a]pyrazol-1-one;

3-[2-(3-Methylphenylamino)-pyrimidin-4-yl]-2-(4-fluorophenyl)-6,7-dihydro-5H-pyrazolo[1,2-a]pyrazol-1-one;

3-[2-(4-Methylphenylamino)-pyrimidin-4-yl]-2-(4-fluorophenyl)-6,7-dihydro-5H-pyrazolo[1,2-a]pyrazol-1-one;

3-[2-(2-Cyanophenylamino)-pyrimidin-4-yl]-2-(4-fluorophenyl)-6,7-dihydro-5H-pyrazolo[1,2-a]pyrazol-1-one;

3-[2-(3-Cyanophenylamino)-pyrimidin-4-yl]-2-(4-fluorophenyl)-6,7-dihydro-5H-pyrazolo[1,2-a]pyrazol-1-one;

3-[2-(4-Cyanophenylamino)-pyrimidin-4-yl]-2-(4-fluorophenyl)-6,7-dihydro-5H-pyrazolo[1,2-a]pyrazol-1-one;

3-[2-(2-Chlorophenylamino)-pyrimidin-4-yl]-2-(4-fluorophenyl)-6,7-dihydro-5H-pyrazolo[1,2-a]pyrazol-1-one;

3-[2-(3-Chlorophenylamino)-pyrimidin-4-yl]-2-(4-fluorophenyl)-6,7-dihydro-5H-1-pyrazolo[1,2-a]pyrazol-1-one;

3-[2-(4-Chlorophenylamino)-pyrimidin-4-yl]-2-(4-fluorophenyl)-6,7dihydro-5H-pyrazolo[1,2-a]pyrazol-1-one;

3-[2-(2,4-Difluoro-phenylamino)-pyrimidin-4-yl]-2-(4-fluorophenyl)-6,7-dihydro-5H-pyrazolo[1,2-a]pyrazol-1-one;

3-[2-(3,5-Difluoro-phenylamino)-pyrimidin-4-yl]-2-(4-fluorophenyl)-6,7-dihydro-5H-pyrazolo[1,2-a]pyrazol-1-one;

3-[2-(2,6-Difluoro-phenylamino)-pyrimidin-4-yl]-2-(4-fluorophenyl)-6,7-dihydro-5H-pyrazolo[1,2-a]pyrazol-1-one;

3-[2-(2,6-Dichlorophenyl)-pyrimidin-4-yl]-2-(4-fluorophenyl)-6,7-dihydro-5H-pyrazolo[1,2-a]pyrazol-1-one;

2-(4-Fluorophenyl)-3-[2-(pyridin-2-ylamino)-pyrimidin-4-yl]-6,7-dihydro-5H-pyrazolo[1,2-a]pyrazol-1-one; and 3-[2-(4,6-Dichloropyrimidin-5-ylamino)-pyrimidin-4-yl]-2-(4-fluoro-phenyl)-6,7-dihydro-5H-pyrazolo[1,2-a]pyrazol-1-one.

The first category of inflammatory cytokine release inhibiting compounds according to the present invention have the general scaffold having the formula:

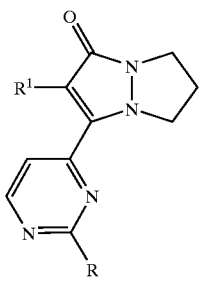

wherein R units are ethers having the formula —OR$^3$, wherein R$^1$ and R$^3$ are described herein below in TABLE I

TABLE I

| No. | R$^1$ | R |
|---|---|---|
| 1 | 4-fluorophenyl | phenoxy |
| 2 | 4-fluorophenyl | 2-fluorophenoxy |
| 3 | 4-fluorophenyl | 3-fluorophenoxy |
| 4 | 4-fluorophenyl | 4-fluorophenoxy |
| 5 | 4-fluorophenyl | 2,6-difluorophenoxy |
| 6 | 4-fluorophenyl | 2-cyanophenoxy |
| 7 | 4-fluorophenyl | 3-cyanophenoxy |
| 8 | 4-fluorophenyl | 2-trifluoromethylphenoxy |
| 9 | 4-fluorophenyl | 4-trifluoromethylphenoxy |
| 10 | 4-fluorophenyl | N-methylpiperadin-4-yl |
| 11 | 4-fluorophenyl | 4-methylphenoxy |
| 12 | 4-fluorophenyl | 2,4-dimethylphenoxy |
| 13 | 4-fluorophenyl | 3-N-acetylaminophenoxy |
| 14 | 4-fluorophenyl | pyran-4-yloxy |
| 15 | 4-fluorophenyl | 4-methoxyphenoxy |
| 16 | 4-fluorophenyl | 3-benzo[1,3]dioxol-5-yl |
| 17 | 2,4-difluorophenyl | phenoxy |
| 18 | 2,4-difluorophenyl | 2-fluorophenoxy |
| 19 | 2,4-difluorophenyl | 3-fluorophenoxy |
| 20 | 2,4-difluorophenyl | 4-fluorophenoxy |
| 21 | 2,4-difluorophenyl | 2,6-difluorophenoxy |
| 22 | 2,4-difluorophenyl | 2-cyanophenoxy |
| 23 | 2,4-difluorophenyl | 3-cyanophenoxy |
| 24 | 2,4-difluorophenyl | 2-trifluoromethylphenoxy |
| 25 | 2,4-difluorophenyl | 4-trifluoromethylphenoxy |
| 26 | 2,4-difluorophenyl | N-methylpiperadin-4-yl |
| 27 | 2,4-difluorophenyl | 4-methylphenoxy |
| 28 | 2,4-difluorophenyl | 2,4-dimethylphenoxy |
| 29 | 2,4-difluorophenyl | 3-N-acetylaminophenoxy |
| 30 | 2,4-difluorophenyl | pyran-4-yloxy |
| 31 | 2,4-difluorophenyl | 4-methoxyphenoxy |
| 32 | 2,4-difluorophenyl | 3-benzo[1,3]dioxol-5-yl |
| 33 | 3-trifluoromethylphenyl | phenoxy |
| 34 | 3-trifluoromethylphenyl | 2-fluorophenoxy |
| 35 | 3-trifluoromethylphenyl | 3-fluorophenoxy |
| 36 | 3-trifluoromethylphenyl | 4-fluorophenoxy |
| 37 | 3-trifluoromethylphenyl | 2,6-difluorophenoxy |
| 38 | 3-trifluoromethylphenyl | 2-cyanophenoxy |
| 39 | 3-trifluoromethylphenyl | 3-cyanophenoxy |
| 40 | 3-trifluoromethylphenyl | 2-trifluoromethylphenoxy |
| 41 | 3-trifluoromethylphenyl | 4-trifluoromethylphenoxy |
| 42 | 3-trifluoromethylphenyl | N-methylpiperadin-4-yl |
| 43 | 3-trifluoromethylphenyl | 4-methylphenoxy |
| 44 | 3-trifluoromethylphenyl | 2,4-dimethylphenoxy |
| 45 | 3-trifluoromethylphenyl | 3-N-acetylaminophenoxy |
| 46 | 3-trifluoromethylphenyl | pyran-4-yloxy |
| 47 | 3-trifluoromethylphenyl | 4-methoxyphenoxy |
| 48 | 3-trifluoromethylphenyl | 3-benzo[1,3]dioxol-5-yl |

The analogs 1–48 and others like them which comprise this category can be suitably prepared by the procedure outlined herein below. In the following example, R$^1$ is 4-fluorophenyl, however, the formulator may suitably substitute any starting material compatible with this procedure, inter alia, methyl phenylacetate, methyl 4-chlorophenylacetate, and methyl 3-(trifluoromethyl)phenylacetate.

General Scheme for Intermediate Type I

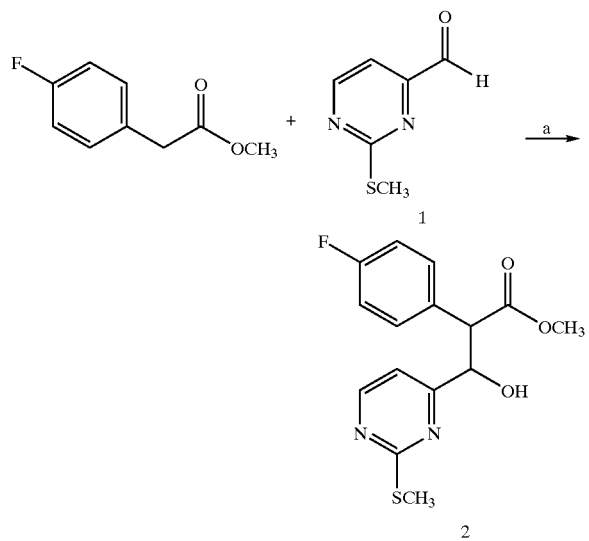

Reagents and conditions: (a) LDA, THF; −78° C., 1 hr.

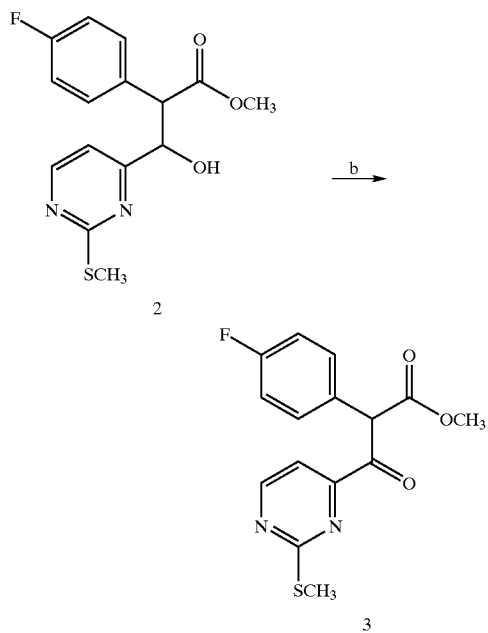

Reagents and conditions: (b) $CrO_3$, $CH_2Cl_2$; rt 16 hr.

EXAMPLE 1

2-(4-Fluorophenyl)-3-(2-methylsulfanyl-pyrimidin-4-yl)-3-oxo-propionic acid methyl ester (3)

The following is a procedure for the preparation of 2-methylsulfanyl-pyrimidine4-carbaldehyde, 1, adapted from the procedure of H. Bredereck et al., Chem. Ber., 97, pp 3407–3417 (1964) included herein by reference.

To a 12 L 3-neck flask under inert atmosphere is charged N,N-dimethyl-formamide dimethyl acetyl (801 g) and pyruvic aldehyde dimethyl acetal (779 g). The mixture is heated to reflux for 18 hours during which time the temperature decreases from about 109° C. to about 80° C. The solution is cooled and methanol (4 L) is added to dissolve the crude residue. The solution is then cooled to 20° C. and thiourea (892 g, 11.7 mol) is added. After allowing the mixture to stir about 15 minutes, sodium methoxide (741 g, 13.7 mol) is added in 4 equal portions over 1 hour while maintaining the solution temperature in the range of 18–28° C. The mixture is stirred for 5 hours at room temperature, cooled to 20° C., then methyl iodide (2 kg) is added over 1.25 hours while maintaining the reaction temperature in the range of 17–29° C. Stirring is continued for 18 hours at room temperature. The methanol and unreacted methyl iodide is removed by heating the solution at 35° C. @ 40 torr to produce about 4.46 kg of a dark residue which is partitioned between 14 L of water and 5 L of ethyl acetate. The water fraction is extracted a second time with ethyl acetate, the organic layers combined and concentrated in vacuo too afford 685 g of an oil which is purified over silica to 522 g of 4dimethoxymethyl-2-methylsulfanyl-pyrimidine.

The dimethyl acetal obtained above is then hydrolyzed to the free aldehyde by heating to 60° C. for 3 hours in 1 M HCl. Workup for neutral using ethyl acetate to extract the product affords 347 g crude product which is purified over silica to afford 401 g of 2-methylsulfanyl-pyrimidine-4-carbaldehyde, 1.

Preparation of 2-(4-fluorophenyl)-3-(2-methylsulfanyl-pyrimidin4)-3-hydroxypropionic acid methyl ester (2): To a cold (−78° C.) solution of lithium diisopropylamide (21.4 mL of 2M solution in THF, 42.8 mmol) in THF (70 mL) is added dropwise a solution of methyl 4-fluorophenyl-acetate (6.0 g, 35.7 mmol) in THF (30 mL). The solution is stirred for 1 hour at −78° C. after which a solution of 2-methylsulfanyl-pyrimidine4-carbaldehyde, 1, (6.0 g, 39.3 mmol) in THF (30 mL) is added dropwise to the reaction mixture. Stirring is continued for 45 minutes at −78° C. then the reaction is quenched by pouring the reaction solution into aqueous saturated $NH_4Cl$. The aqueous phase is extracted with ethyl acetate. The organic phases combined, dried ($MgSO_4$), filtered, and concentrated in vacuo. The crude residue is purified over silica (33% EtOAc/hexanes) to afford 8.7 g (76%) of the desired product as a mixture (1:1) of diastereomers.

Preparation of 2-(4-fluorophenyl)-3-(2-methylsulfanyl-pyrimidin-4yl)-3-oxo-propionic acid methyl ester (3): To a suspension of $CrO_3$ in $CH_2Cl_2$ (300 mL) is added pyridine. The mixture is stirred vigorously for 1 hour at room temp. A solution of the crude 2-(4-fluorophenyl)-3-(2-methylsulfanyl-pyrimidin-4-yl)-3-hydroxypropionic acid methyl ester, 2, prepared above in $CH_2Cl_2$ (50 mL) is added dropwise to the chromium suspension. The reaction mixture is stirred at room temperature for 16 hours, diluted with ether (1 L) and filtered through a pad of Celite. The filtrate is concentrated in vacuo and the resulting residue is purified over silica (25% EtOAc/hexanes) to afford 3.7 g (43% yield) of the desired product as a yellow solid.

The following example relates to the formation of 6,7dihydro-5H-pyrazolo[1,2-a]pyrazol-1-one ring systems utilizing pyrazolidine, however the formulator may utilize substituted cyclic hydrazine reagents to achieve other scaffolds having $R^2$ ring units which are not hydrogen, inter alia, 3-methylpyrazolidine.

General Scheme for Intermediate Type II

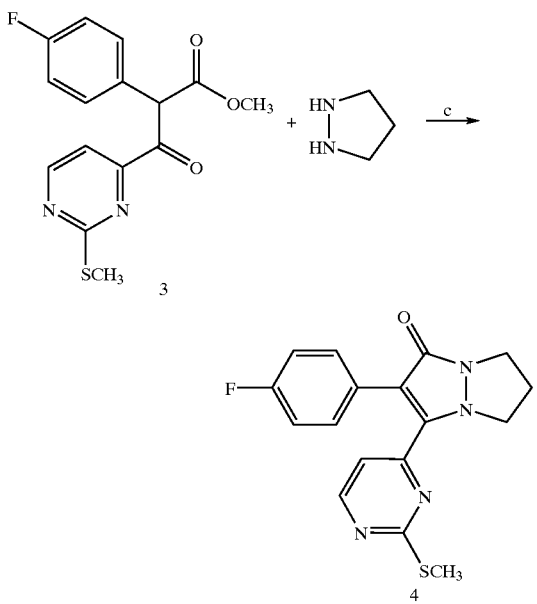

Reagents and conditions: (c) pyridine, 90° C., 16 hr.

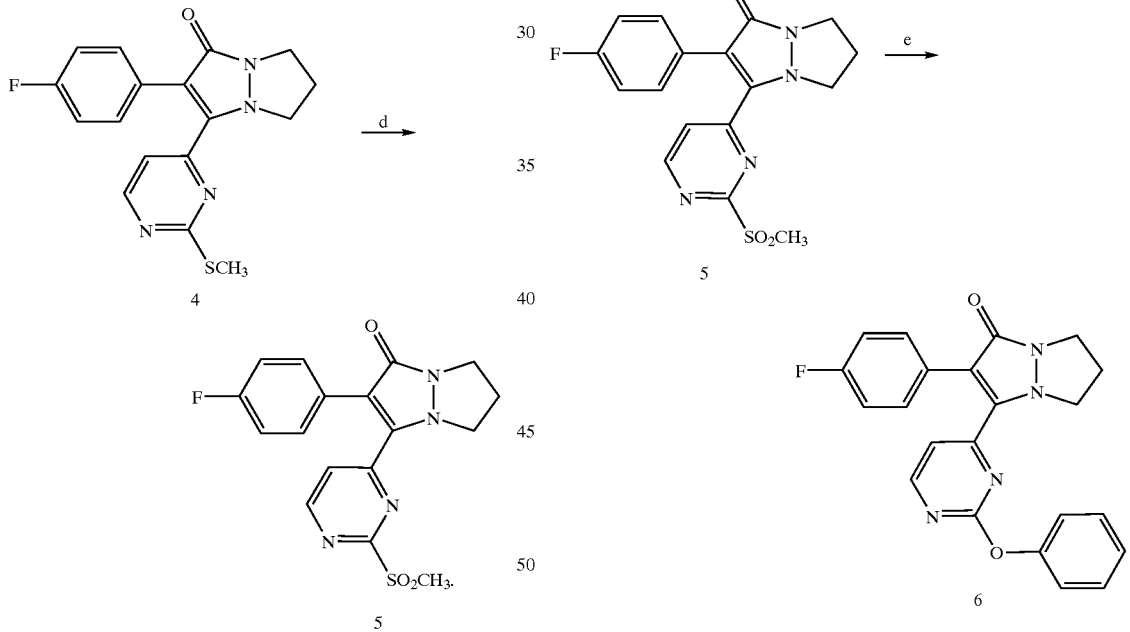

Reagents and conditions: (d) Oxone®, MeOH/THF/H$_2$O; rt 1 hr.

EXAMPLE 2

2-(4-Fluorophenyl)-3-(2-methanesulfonyl-pyrimidin-4-yl)-6,7-dihydro-5H-pyrazolo[1,2-a]pyrazol-1-one (5)

Preparation of 2-(4-fluorophenyl)-3-(2-methylsulfanyl-pyrimidin-4-yl)-6,7-dihydro-5H-pyrazolo[1,2-a]pyrazol-1-one (4): To a solution of pyrazolidine (7.8 g, 54.16 mmol) in pyridine (100 mL) is added 2-(4-fluorophenyl)-3-(2-methylsulfanyl-pyrimidin-4-yl)-3-oxo-propionic acid methyl ester, 3, (11.5 g, 36.1 mmol). The reaction mixture is heated to 90° C. for 16 hours. The solvent is removed in vacuo and the resulting residue purified over silica (100% EtOAc, followed by 10% MeOH/EtOAc) to afford 3.9 g (37% yield) of the desired product as a yellow solid.

Preparation of 2-(4fluorophenyl)-3-(2-methanesulfonyl-pyrimidin-4-yl)-6,7-dihydro-5H-pyrazolo[1,2-a]pyrazol-1-one (5): To a solution of 2-(4-fluorophenyl)-3-(2-methylsulfanyl-pyrimidin-4-yl)-6,7-dihydro-5H-pyrazolo[1,2-a]pyrazol-1-one, 4, (1.3 g. 3.8 mmol) in THF: methanol (56 mL of a 1:1 mixture) is added dropwise a solution of Oxone® (potassium peroxymonosulfate) (9.34 g, 15.2 mmol) in water (42 mL). The reaction is stirred 1 hour at room temperature, diluted with aqueous NaHCO$_3$ and extract three times with ethyl acetate. The organic layers are combined, dried, and concentrated in vacuo too afford the crude desired product which is used without further purification.

The following is a procedure wherein Intermediate Type II compounds can be utilized for preparation of the inflammatory cytokine release inhibitors of Category I.

EXAMPLE 3

2-(4-Fluorophenyl)-3-(2-phenoxy-pyrimidin-4-yl)-6,7-dihydro-5H-pyrazolo-[1,2-a]pyrazol-1-one (6)

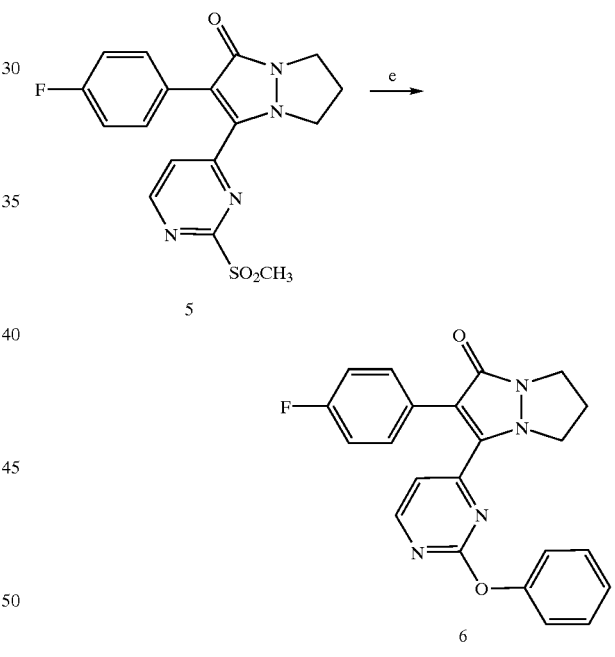

Reagents and conditions: (e) phenol, NaH, THF, 1.5 hr rt.

Preparation of 2-(4-fluorophenyl)-3-(2-phenoxy-pyrimidin-4-yl)-6,7-dihydro-5H-pyrazolo-[1,2-a]pyrazol-1-one (6): To a solution of phenol (0.66 g, 7.08 mmol) in THF (5 mL) is added NaH (0.24 g, 5.91 mmol) followed by a solution of the crude 2-(4-fluorophenyl)-3-(2-methanesulfonyl-pyrimidin4-yl)-6,7-dihydro-5H-pyrazolo[1,2-a]pyrazol-1-one, 5, prepared herein above (0.25 g, 0.67 mmol) in THF (2 mL). The reaction mixture is stirred for 1.5 hours at room temperature, diluted with aqueous NaHCO$_3$ and extracted with twice with ethyl acetate. The organic layers are combined, dried over MgSO$_4$, and concentrated in vacuo to afford the crude product which is purified over silica (100% EtOAc, followed by 10% MeOH/EtOAc) to provide 0.35 g (38% yield) of the desired product as a yellow solid. ¹H NMR (300 MHz, CDCl₃) □ 8.47 (d, J=5.1 Hz, 1H), 7.49 (dd, J=7.8, 7.8 Hz, 2H), 7.40 (ddd, J=5.4, 5.4 Hz, 2H), 7.35–7.22 (m, 3H), 7.10 (dd, J=8.4, 8.4 Hz, 2H), 6.90 (d, J=6.8 Hz, 2H), 4.05 (t, J=7.2 Hz, 2H), 3.86 (t, J=7.2 Hz, 2H), 2.59 (dt, J=7.2, 7.2 Hz, 2H); HRMS cald for $C_{22}H_{18}FN_4O_2(M+H)^+$ 389.1414; found 389.1407. This compound corresponds to analog 1 from Table I.

The following compounds from the first aspect of Category I can be prepared by the procedure described herein above.

N-(3-{4-[2-(4-Fluoro-phenyl)-3-oxo-6,7-dihydro-3H,5H-pyrazolo[1,2-a]pyrazol-1-yl]-pyrimidin-2-yloxy}-phenyl)-acetamide; ¹H NMR (300 MHz, d₆-DMSO) □ 10.11 (s, 1H), 8.66 (d, J=5.1 Hz, 1H), 7.64 (m, 1H), 7.41–7.34 (m, 4H), 7.17 (t, J=9.0 Hz, 2H), 7.02 (d, J=51 Hz, 6.92–6.80 (m, 1H), 3.84 (t, J=6.9 Hz, 2H), 3.81 (t, J=6.9 Hz, 2H), 2.46 (m, 2H), 2.06 (s, 3H); HRMS calcd for $C_{24}H_{20}FN_5O_3$ $(M+H)^+$ 446.1628; found 446.1606.

2-(4-Fluorophenyl)-3-[2-(2,4-dimethylphenoxy)pyrimidin-4-yl)6,7-dihydro-5H-pyrazolo-[1,2-a]pyrazol-1-one; ¹H NMR (300 MHz, CDCl₃) □ 8.44 (dd, J=5.4, 1.5 Hz, 1H), 7.43–7.38 (m, 2), 7.14–7.00 (m, 5H), 6.88 (dd, J=5.1, 1.5 Hz, 1H), 4.02 (t, J=7.2 Hz, 2H), 3.86 (t, J=7.2 Hz, 2H), 2.59 (dt, J=7.2, 7.2 Hz, 2H), 2.38 (s, 3H), 2.19(s, 3H); HRMS calcd for $C_{24}H_{21}FN_4O_2$ $(M+H)^+$417.1727; found 417.1727.

2-(2,4-Difluorophenyl)-3-(2phenoxy-pyrimidin-4-yl)-6,7-dihydro-5H-pyrazolo-[1,2-a]pyrazol-1-one; ¹H NMR (300 MHz, CDCl₃) □ 8.52 (d, J=5.1 HZ, 1H), 7.60–7.46 (m, 3H), 7.33 (d, J=7.5 Hz, 1H), 7.23 (d, J=7.5 Hz, 2H), 7.01 (t, J=8.1 Hz, 1H0, 6.91–6.83 (m, 2H), 4.09 (t, J=6.6 Hz, 2H), 3.92 (t, J=6.9 Hz, 2H), 2.59 (t, J=6.9 Hz, 2H): MS $(M+H)^+$ 407.2.

2-(4-fluorophenyl)-3-[2-(4-fluorophenoxy)pyrimidin-4-yl)-6,7-dihydro-5H-pyrazolo-[1,2-a]pyrazol-1-one; ¹H NMR (300 MHz, CDCl₃) □ 8.51 (d, J=5.1 Hz, 1H), 7.39(dd, J=8.7, 5.4 Hz, 2H), 7.21–7.10 (m, 5H), 6.91 (d, J=5.1 Hz, 1H), 4.42–4.35 (m, 2H), 4.10–4.04 (t, J=7.2 Hz, 2H), 2.71 (dt, J=7.2, 7.2 Hz, 2H); MS $(M+H)^+$406.9.

2-(4-Fluorophenyl)-3-[2-(2,6-difluorophenoxy)pyrimidin-4-yl)-6,7dihydro-5H-pyrazolo-(1,2-a]pyrazol-1-one; ¹H NMR (300 MHz, CDCl₃) □ 8.52 (d, J=5.1 Hz, 1H), 7.41 (dd, J=8.7, 5.4 Hz, 2H), 7.15–7.07 (m, 5H), 6.98 (d, J=5.1 Hz, 1H), 4.31 (t, J=8.2 Hz, 2H), 4.09 (t, J=8.2 Hx, 2H), 2.70 (dt, J=8.2, 8.2 Hz, 2H); MS $(M+H)^+$ 425.2.

2-(4-Fluorophenyl)-3-[2-(2-fluorophenoxy)pyrimidin-4-yl)-6,7-dihydro-5H-pyrazolo-[1,2-a]pyrazol-1-one; ¹H NMR (300 MHz, CDCl₃) □ 8.51 (d, J=5.1 Hz, 1H), 7.41–7.23 (m, 6H), 7.11 (t, J=8.7 Hz, 2H), 6.94 (d, J=5.1 Hz, 1H), 4.27 (t, J=8.2 Hz, 2H), 4.00 (t, J=8.2 Hz, 2H), 2.66 (dt, J=8.2, 8.2 Hz, 2H); MS $(M+H)^+$407.2.

2-(4-Fluorophenyl)-3-[2-(3-fluorophenoxy)pyrimidin-4-yl)-6,7-dihydro-5H-pyrazolo-[1,2-a]pyrazol-1-one; ¹H NMR (300 MHz, CDCl₃) □ 8.49 (d, J=5.1 Hz, 1H), 7.49–7.38 (m, 3H), 7.11 (t, J=8.7 Hz, 2H), 7.04–6.98 (m, 3H), 6.94 (d, J=5.1 Hz, 1H), 4.13 (t, J=6.9 Hz, 2H), 3.97 (t, J=6.9 Hz, 2H), 2.66 (dt, J=6.9, 6.9 Hz, 2H); MS $(M+H)^+$ 406.9.

A second aspect of the Category I inflammatory cytokine release inhibiting compounds according to the present invention have the general scaffold having the formula:

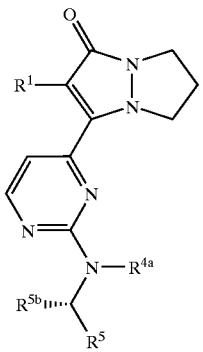

wherein R units are amines having the formula —$NR^{4a}$[$CHR^{5b}$]$R^6$, and $R^1$, $R^{4a}$, $R^{5b}$, and $R^6$ are described herein below in Table II. The stereochemistry of $R^{5b}$ is the configuration shown when $R^{5b}$ or $R^6$ is not hydrogen.

TABLE II

| No. | $R^1$ | $R^{4a}$ | $R^{5b}$ | $R^6$ |
|---|---|---|---|---|
| 49 | 4-fluorophenyl | H | H | phenyl |
| 50 | 4-fluorophenyl | H | H | 4-fluorophenyl |
| 51 | 4-fluorophenyl | H | H | 2-aminophenyl |
| 52 | 4-fluorophenyl | H | H | 2-methylphenyl |
| 53 | 4-fluorophenyl | H | H | 4-methylphenyl |
| 54 | 4-fluorophenyl | H | H | 4-methoxyphenyl |
| 55 | 4-fluorophenyl | H | H | 4-(propanesulfonyl)phenyl |
| 56 | 4-fluorophenyl | H | H | 3-benzo[1,3]dioxol-5-yl |
| 57 | 4-fluorophenyl | H | H | pyridin-2-yl |
| 58 | 4-fluorophenyl | H | H | pyridin-3-yl |
| 59 | 4-fluorophenyl | H | methyl | phenyl |
| 60 | 4-fluorophenyl | H | methyl | 4-fluorophenyl |
| 61 | 4-fluorophenyl | H | methyl | 2-aminophenyl |
| 62 | 4-fluorophenyl | H | methyl | 2-methylphenyl |
| 63 | 4-fluorophenyl | H | methyl | 4-methylphenyl |
| 64 | 4-fluorophenyl | H | methyl | 4-methoxyphenyl |
| 65 | 4-fluorophenyl | H | methyl | 4-(propanesulfonyl)phenyl |
| 66 | 4-fluorophenyl | H | methyl | 3-benzo[1,3]dioxol-5-yl |
| 67 | 4-fluorophenyl | H | methyl | pyridin-2-yl |
| 68 | 4-fluorophenyl | H | methyl | pyridin-3-yl |
| 69 | 4-fluorophenyl | H | H | H |
| 70 | 4-fluorophenyl | H | H | methyl |
| 71 | 4-fluorophenyl | H | H | ethyl |
| 72 | 4-fluorophenyl | H | H | vinyl |
| 73 | 4-fluorophenyl | H | H | cyclopropyl |
| 74 | 4-fluorophenyl | H | H | cyclohexyl |
| 75 | 4-fluorophenyl | H | H | methoxymethyl |
| 76 | 4-fluorophenyl | H | H | methoxyethyl |
| 77 | 4-fluorophenyl | H | H | 1-hydroxy-1-methylethyl |
| 78 | 4-fluorophenyl | H | H | —$CO_2H$ |
| 79 | 4-fluorophenyl | H | methyl | H |
| 80 | 4-fluorophenyl | H | methyl | methyl |
| 81 | 4-fluorophenyl | H | methyl | ethyl |
| 82 | 4-fluorophenyl | H | methyl | vinyl |
| 83 | 4-fluorophenyl | H | methyl | cyclopropyl |
| 84 | 4-fluorophenyl | H | methyl | cyclohexyl |
| 85 | 4-fluorophenyl | H | methyl | methoxymethyl |
| 86 | 4-fluorophenyl | H | methyl | methoxyethyl |
| 87 | 4-fluorophenyl | H | methyl | 1-hydroxy-1-methylethyl |
| 88 | 4-fluorophenyl | H | methyl | —$CO_2H$ |
| 89 | 3-trifluoromethylphenyl | H | methyl | phenyl |
| 90 | 3-trifluoromethylphenyl | H | methyl | 4-fluorophenyl |
| 91 | 3-trifluoromethylphenyl | H | methyl | 2-aminophenyl |
| 92 | 3-trifluoromethylphenyl | H | methyl | 2-methylphenyl |
| 93 | 3-trifluoromethylphenyl | H | methyl | 4-methylphenyl |
| 94 | 3-trifluoromethylphenyl | H | methyl | 4-methoxyphenyl |
| 95 | 3-trifluoromethylphenyl | H | methyl | 4-(propanesulfonyl)phenyl |
| 96 | 3-trifluoromethylphenyl | H | methyl | 3-benzo[1,3]dioxol-5-yl |
| 97 | 3-trifluoromethylphenyl | H | methyl | pyridin-2-yl |

TABLE II-continued

| No. | R¹ | R⁴ᵃ | R⁵ᵇ | R⁶ |
|---|---|---|---|---|
| 98 | 3-trifluoromethylphenyl | H | methyl | pyridin-3-yl |
| 99 | 3-trifluoromethylphenyl | H | methyl | H |
| 100 | 3-trifluoromethylphenyl | H | methyl | methyl |
| 101 | 3-trifluoromethylphenyl | H | methyl | ethyl |
| 102 | 3-trifluoromethylphenyl | H | methyl | vinyl |
| 103 | 3-trifluoromethylphenyl | H | methyl | cyclopropyl |
| 104 | 3-trifluoromethylphenyl | H | methyl | cyclohexyl |
| 105 | 3-trifluoromethylphenyl | H | methyl | methoxymethyl |
| 106 | 3-trifluoromethylphenyl | H | methyl | methoxyethyl |
| 107 | 3-trifluoromethylphenyl | H | methyl | 1-hydroxy-1-methylethyl |
| 108 | 3-trifluoromethylphenyl | H | methyl | —CO₂H |

Utilizing intermediates such as compound 5, as a convenient starting point the analogs 14–108 and others encompassed within the description of this category can be suitably prepared by the procedure outlined herein below. In the following example, R¹ is 4-fluorophenyl, however, the formulator may suitably substitute any starting material compatible with this procedure, inter alia, methyl phenylacetate, methyl 4-chlorophenyl-acetate, and methyl 3-(trifluoromethyl)phenylacetate.

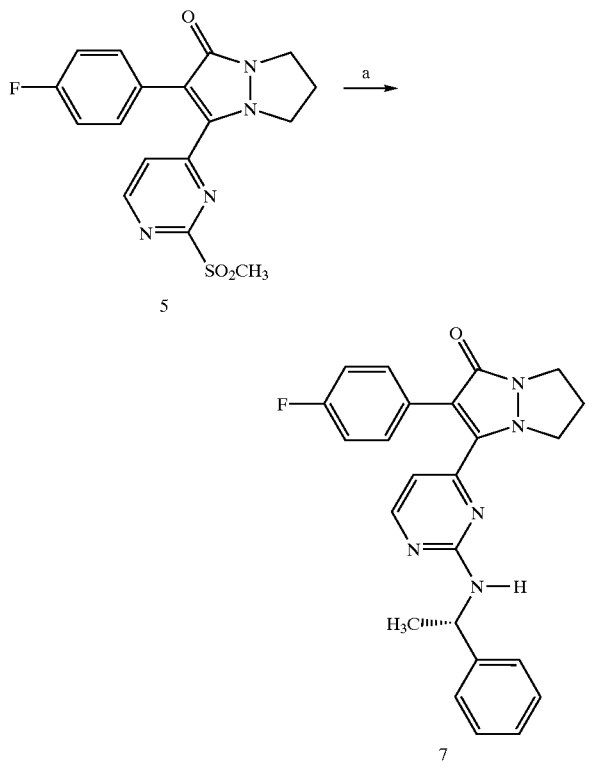

Reagents and conditions: (a) (S)-(□)-methylbenzylamine, toluene, 140° C., 12 hr.

EXAMPLE 4

2-(4-Fluorophenyl)-3-[2-(S)-(1-phenylethylamino) pyrimidin-4-yl]-6,7-dihydro-5H-pyrazolo[1,2a] pyrazol-1-one (7)

Preparation of 2-(4-fluorophenyl)-3-[2-(S)-(1-phenylethylamino)pyrimidin-4-yl]-6,7-dihydro-5H-pyrazolo[1,2-a]pyrazol-1-one (7): A solution of the crude 2-(4-fluorophenyl)-3-(2-methanesulfonyl-pyrimidin4-yl)-6,7-dihydro-5H-pyrazolo[1,2-a]pyrazol-1-one, 5, prepared herein above (0.86 g, 2.3 mmol) and (S)-(-)-□-methyl-benzyl amine (10.5 mL, 81.6 mmol) is dissolved in toluene (18 mL). The resulting mixture is heated to 140° C. for 12 hours, cooled to room temperature and the solvent removed in vacuo. The resulting residue is purified over silica (1:1 EtOAc/hexanes) to afford the desired product which to analog 59 from Table II. ¹H NMR (300 MHz, CDCl₃) □ 8.18 (d, J=5.1 Hz, 1H), 7.42–7.34 (m, 7H), 7.04 (ddd, J=9.0, 6.9, 2.1 Hz), 2H), 6.39 (d, J=5.1 Hz, 1H), 5.68 (bd s, 1H), 5.10 (m, 1H), 3.97 (dt, J=7.5, 7.5, 7.5 Hz, 2H), 2.45 (bd s, 2H), 1.67 (m, 2H), 1.60 (d, J=7.5 Hz, 3H); HRMS calcd for C₂₄H₂₂FN₅O (M+H)⁺416.1887; found 416.1897.

The following compounds from the second aspect of Category I can be prepared by the procedure described herein above.

2-(4-Fluorophenyl)-3-[2-(N'-methyl-N'-phenylhydrazino)-pyrimidin-4-yl]-6,7-dihydro-5H-pyrazolo[1,2-a]pyrazol-1-one: ¹H NMR (300 MHz, CDCl₃) □ 8.29 (d, J=5.1 Hz, 1H), 7.40 (dd, J=8.4, 5.4 Hz, 2H), 7.29–7.25 (m, 2H), 7.06 (dd, J=8.4, 8.4 Hz, 2H), 6.91 (d, J=9.0 Hz, 2H), 6.85 (t, 7.8 Hz, 1H), 6.57 (d, J=5.1 Hz, 1H), 4.00 (t, J=6.9 Hz, 4H), 3.39 (s, 3H), 2.48–2.33 (m, 2H); MS (M+H)⁺417.2.

(R)-{4-[2-(4-Fluorophenyl)-3-oxo-6,7-dihydro-}3H,5H-pyrazolo[1,2-a]pyrazol-1-yl]-pyrimidin-2-ylamino-] phenylacetic acid methyl ester; ¹H NMR (300 MHz, CDCl₃) □ 8.26 (d, J=8.4 Hz, 7.54–7.24 (m, 7H), 7.04 (t, J=8.4 Hz, 2H), 6.47 (d, J=4.8 Hz, 1H), 5.56–5.58 (m, 2H), 4.05–4.00 (m, 2H), 3.79 (s, 3H), 3.78–3.68 (m, 2H), 1.67 (m, 2H); MS (M+H)⁺460.0.

2-(4-Fluorophenyl)-3(2-benzylaminopyrimidin-4-yl)-6,7-dihydro-5H-pyrazolo[1,2-a]pyrazol-1-one; ¹H NMR (300 MHz, CDCl₃) □ 8.21 (d, J=4.5 Hz, 1H), 7.45–7.29 (m, 9H), 7.06 (dd, J=9.0, 8.4 Hz, 2H), 6.47 (d, J=5.4 Hz, 1H), 4.70 (d, J=6.0 Hz, 2H), 4.04 (t, J=7.2 Hz, 2H), 3.80–3.65 (m, 2H), 2.65–2.52 (m, 2H); MS (M+H)⁺402.1.

2-(4-Fluorophenyl)-3-[2-(1-(S)-methylethylamino) pyrimidin-4-yl]-6,7-dihydro-5H-pyrazolo[1,2-a]pyrazol-1-one; ¹H NMR (300 MHz, CDCl₃)□ 8.17 (d, J=4.8 Hz, 7.46–7.40 (m, 2H), 7.05 (dt, J=8.7, 2.4 Hz, 2H), 6.38 (dd, J=4.8, 3.0 Hz, 1H), 5.11 (bd s, 1H), 4.13–3.96 (m, 5H), 2.73 (dt, J=6.9, 6.9 Hz, 2H), 1.66–1.55 (m, 2H), 1.24 (d, J=6.3 Hz, 3H), 0.99 (t, J=7.2 Hz, 3H); HRMS calcd for C₂₀H₂₂FN₅O (M+H)⁺368.1886; found 386.1880.

2(4-Fluorophenyl)-3-[2-(allylamino)pyrimidin-4-yl]-6,7-dihydro-5H-pyrazolo[1,2-a]pyrazol-1-one; ¹H NMR (300 MHz, CDCl₃)□ 8.20 (d, J=5.1 Hz, 1H), 7.43 (dd, J=9.0, 5.4 Hz, 2H), 7.05 (t, J=8.7 Hz, 2H), 6.43 (d, J=5.1 Hz, 1H), 6.00 (dddd, J=7.2, 7.2, 7.2, 5.1 Hz, 1H), 5.45 (bd s, 1H), 5.28 (dd, J=17.1, 1.5 Hz, 1H), 5.20 (dd, J=10.2, 1.5 Hz, 1H), 4.13–4.04 (m, 6H), 2.71 (dt, J=7.2, 7.2 Hz, 2H); HRMS calcd for C₁₉H₁₈FN₅O (M+H)⁺ 352.1573; found 352.1582.

2-(4-Fluorophenyl)-3-{2-[1-(S)-(4-methylphenyl) ethylamino]pyrimidin-4-yl}-6,7-dihydro-5H-pyrazolo[1,2-a]pyrazol-1-one; ¹H NMR (300 MHz, (CDCl₃) □ 8.15 (d, J=5.4 Hz, 1H), 7.40 (dd, J=8.7, 5.7 Hz, 2H), 7.28–7.27 (m, 2H), 7.17 (d, J=7.8 Hz, 2H), 7.04 (t, J=9.0 Hz, 2H), 6.41 (d, J=5.4 Hz, 1H), 5.20 (m, 1H), 4.02–3.96 (m, 4H), 2.52–2.45 (m, 2H), 2.36 (s, 3H), 1.60 (d, J=6.9 Hz, 3H); HRMS calcd for C₂₅H₂₄FN₅O (M+H)⁺ 430.2043; found 430.2057.

2-(4-Fluorophenyl)-3-[2-(1-(S)-cyclohexyl-ethylamino) pyrimidin4-yl]-6,7-dihydro-5H-pyrazolo[1,2-a]pyrazol-1-one; ¹H NMR (300 MHz, CDCl₃) □ 8.16 (d, J=4.8 Hz, 1H), 7.44 (dd, J=9.0, 5.7 Hz, 2H), 7.05 (t, J=8.7 Hz, 2H), 6.37 (d, J=5.1 Hz, 1H), 5.12 (bd s, 1H), 4.14–4.02 (m, 4H), 3.99–3.92 (m, 1H), 2.73 (dt, J=6.9, 6.9 Hz, 2H), 1.88–1.63 (m, 4H), 1.54–1.40 (m, 1H), 1.28–1.03 (m, 6H), 1.20 (d, J=6.9 Hz, 3H); HRMS calcd for $C_{24}H_{28}FN_5O$ (M+H)$^+$ 421.2279; found 421.2264.

2-(4-Fluorophenyl)-3-[2-(1-(R)-phenylethylamino) pyrimidin-4-yl]-6,7-dihydro-5H-pyrazolo[1,2-a]pyrazol-1-one; $^1$H NMR (300 MHz, CDCl$_3$) □ 8.11 (d, J=5.4 Hz, 1H), 7.43–7.23 (m, 7H), 7.05 (1, J=8.4 Hz, 2H), 6.43 (d, J=5.4 Hz, 1H), 5.13 (m, 1H), 4.16–3.94 (m, 2H), 2.58–2.38 (m, 2H), 1.63 (d, J=6.9 Hz, 3H); MS (M+H)$^+$ 416.0.

2-(4-Fluorophenyl)-3-[2-(tert-butylamino)pyrimidin-4-yl]6,7-dihydo-5H-pyrazolo[1,2-a]pyrazol-1-one; $^1$H NMR (300 MHz, CDCl$_3$) □ 8.11 (d, J=5.4 Hz, 1H), 7.43 (dd, J=6.9, 3.3 Hz, 2H), 7.08 (t, J=6.6 Hz, 2H), 6.45 (d, J=5.7 Hz, 1H), 412–4.02 (m, 4H), 2.77 (dt, J=7.2, 7.2 Hz, 2H), 1.52 (s, 9H); MS (M+H)$^+$ 368.1.

2-(4-Fluorophenyl)-3-[2-(2-hydroxy-1,2-dimethylpropylamino)pyrimidin-4-yl]-6,7-dihydro-5H-pyrazolo[1,2-a]pyrazol-1-one; $^1$H NMR (300 MHz, CDCl$_3$) □ 7.99 (mn, 1H), 7.40 (dd, J=9.0, 5.7 Hz, 2H), 7.10(t, J=8.7 Hz, 2H), 6.55 (d, J=5.4 Hz, 1H), 4.24–4.10 (m, 5H), 2.38 (dt, J=8.4, 8.4 Hz, 2H), 1.51–1.36 (m, 9H); MS (M+H)$^+$ 398.1.

2-(4-Fluorophenyl)-3-[(2-cyclopropylamino)pyrimidin-4-yl]-6,7-dihydro-5H-pyrazolo[1,2-a]pyrazol-1-one; $^1$H NMR (300 MHz, CDCl$_3$) □ 8.17 (m, 1H), 7.42 (dd, J=8.7, 5.4 Hz, 2H), 7.12 (t, J=8.7 Hz, 2H), 6.52 (d, J=5.4 Hz, 1H), 4.27 (m, 2H), 4.15 (t, J=8.4 Hz, 2H), 2.88–2.81 (m, 1H), 2.77 (dt, J=8.4, 8.4 Hz, 2H), 0.93–0.87 (m, 2H), 0.71–0.66 (m, 2H); MS (M+H)$^+$ 352.0.

2-(4-Fluorophenyl)-3-[(2-cyclopropylmethyl) aminopyrimidin-4-yl]-6,7-dihydro-5H-pyrazolo[1,2-a] pyrazol-1-one; $^1$H NMR (300 MHz, CDCl$_3$) □ 8.17 (d, J=5.1 Hz, 1H), 7.41 (dd, J=8.7, 5.4 Hz, 2H), 7.07 (t, J=8.7 Hz, 2H), 6.41 (d, J=5.1 Hz, 1H), 5.55 (bd s, 1H), 4.15–4.05 (m, 4H), 3.31 (t, J=5.4 Hz, 2H), 2.78 (dt, J=6.9, 6.9 Hz, 2H), 1.18 (m, 1H), 0.60 (m, 2H), 0.30 (m, 2H); MS (M+H)$^+$ 366.0.

2-(4-Fluorophenyl)-3-[(2-methoxyethylamino)pyrimidin-4-yl]-6,7-dihydro-5H-pyrazolo[1,2-a]pyrazol-1-one; $^1$H NMR (300 MHz, CDCl$_3$) □8.18 (d, J=5.1 Hz, 1H), 7.42 (dd, J=8.7, 5.7 Hz, 2H), 7.06 (t, J=8.7 Hz, 2H), 6.42 (d, J=5.4 Hz, 1H), 4.20–4.03 (m, 4H), 3.68–3.41 (m, 4H), 3.42 (s, 3H), 2.74 (dt, J=6.9, 6.9 Hz, 2H); MS (M+H)$^+$ 370.0.

2-(4-Fluorophenyl)-3-[2-(2-methoxy-1-(S)-methylethylamino)pyrimidin-4-yl]-6,7-dihydro-5H-pyrazolo[1,2-a]pyrazol-1-one; $^1$H NMR (300 MHz, CDCl$_3$) □ 8.18 (d, J=4.8 Hz, 1H), 7.42 (dd, J=8.1, 5.4 Hz, 2H), 7.04 (t, J=8.7 Hz, 2H), 6.39 (d, J=4.8 Hz, 1H), 5.49 (d, J=7.8 Hz, 1H), 4.26 (m, 1H), 4.13 (t, J=6.9 Hz, 2H), 4.06 (t, J=6.9 Hz, 2H), 3.46 (d, J=4.8 Hz, 2H), 3.41 (s, 3H), 2.72 (dt, J=6.9, 6.9 Hz, 2H), 1.30 (s, 3H); MS (M+H)$^+$ 384.0.

2-(4-Fluorophenyl)-3-{2-[1-(S)-(4-fluorophenyl) ethylamino]pyrimidin-4-yl}-6,7-dihydro-5H-pyrazolo[1,2-a]pyrazol-1-one; $^1$H NMR (300 MHz, CDCl$_3$) □18.10 (d, J=5.1 Hz, 1H), 7.39 (dd, J=7.8, 5.1 Hz, 2H), 7.07 (t, J=7.8Hz, 2H), 6.48 (d, J=5.1 Hz, 1H), 5.12 (m, 1H), 4.18–3.98 (m, 2H), 2.61–2.45 (m, 2H), 1.64 (d, J=6.9 Hz, 3H); MS (M+H)$^+$ 433.9.

2-(4-Fluorophenyl)-3-[2-[(pyridin-3-ylmethyl)amino] pyrimidin-4-yl]-6,7-dihydro-5H-pyrazolo[1,2-a]pyrazol-1-one; $^1$H NMR (300 MHz, d$_6$-DMSO) □8.69–8.51 (m, 2H), 8.22 (d, J=5.1 Hz, 1H), 7.73–7.68 (m, 1H), 7.42 (dd, J=8.7, 5.4 Hz, 2H), 7.33–7.26 (m, 1H), 7.04 (t, J=8.7 Hz, 2H), 6.48 (d, J=5.1 Hz, 1H), 5.77 (bd s, 1H), 4.69 (d, J=6.3 Hz, 2H), 4.02 (t, J=6.9 Hz, 2H), 3.80 (m, 2H), 2.62 (dt, J=8.7, 8.7 Hz, 2H); MS (M+H)$^+$ 403.1.

The second category of inflammatory cytokine release inhibiting compounds according to the present invention have the general scaffold having the formula:

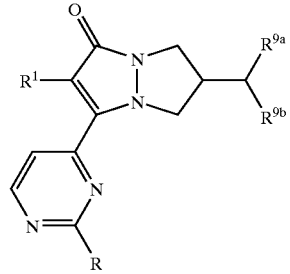

wherein R units are ethers having the formula —OR$^3$ and R$^{9a}$ and R$^{9b}$ are taken together to form a ring as described herein below in Table III.

TABLE III

| No. | R$^1$ | R$^3$ | R$^{9a}$/R$^{9b}$ ring |
|---|---|---|---|
| 109 | 4-fluorophenyl | phenoxy | morpholinyl |
| 110 | 4-fluorophenyl | 2-fluorophenoxy | morpholinyl |
| 111 | 4-fluorophenyl | 3-fluorophenoxy | morpholinyl |
| 112 | 4-fluorophenyl | 4-fluorophenoxy | morpholinyl |
| 113 | 4-fluorophenyl | 2,6-difluorophenoxy | morpholinyl |
| 114 | 4-fluorophenyl | 2-cyanophenoxy | morpholinyl |
| 115 | 4-fluorophenyl | 3-cyanophenoxy | morpholinyl |
| 116 | 4-fluorophenyl | 2-trifluoromethylphenoxy | morpholinyl |
| 117 | 4-fluorophenyl | 4-trifluoromethylphenoxy | morpholinyl |
| 118 | 4-fluorophenyl | 2-methylphenoxy | morpholinyl |
| 119 | 4-fluorophenyl | 4-methylphenoxy | morpholinyl |
| 120 | 4-fluorophenyl | 2,4-dimethylphenoxy | morpholinyl |
| 121 | 4-fluorophenyl | 3-N-acetylaminophenoxy | morpholinyl |
| 122 | 4-fluorophenyl | 2-methoxyphenoxy | morpholinyl |
| 123 | 4-fluorophenyl | 4-methoxyphenoxy | morpholinyl |
| 124 | 4-fluorophenyl | 3-benzo[1,3]dioxol-5-yl | morpholinyl |
| 125 | 4-fluorophenyl | phenoxy | piperidin-1-yl |
| 126 | 4-fluorophenyl | 2-fluorophenoxy | piperidin-1-yl |
| 127 | 4-fluorophenyl | 3-fluorophenoxy | piperidin-1-yl |
| 128 | 4-fluorophenyl | 4-fluorophenoxy | piperidin-1-yl |
| 129 | 4-fluorophenyl | 2,6-difluorophenoxy | piperidin-1-yl |
| 130 | 4-fluorophenyl | 2-cyanophenoxy | piperidin-1-yl |
| 131 | 4-fluorophenyl | 3-cyanophenoxy | piperidin-1-yl |
| 132 | 4-fluorophenyl | 2-trifluoromethylphenoxy | piperidin-1-yl |
| 133 | 4-fluorophenyl | 4-trifluoromethylphenoxy | piperidin-1-yl |
| 134 | 4-fluorophenyl | 2-methylphenoxy | piperidin-1-yl |
| 135 | 4-fluorophenyl | 4-methylphenoxy | piperidin-1-yl |
| 136 | 4-fluorophenyl | 2,4-dimethylphenoxy | piperidin-1-yl |
| 137 | 4-fluorophenyl | 3-N-acetylaminophenoxy | piperidin-1-yl |
| 138 | 4-fluorophenyl | 2-methoxyphenoxy | piperidin-1-yl |
| 139 | 4-fluorophenyl | 4-methoxyphenoxy | piperidin-1-yl |
| 140 | 4-fluorophenyl | 3-benzo[1,3]dioxol-5-yl | piperidin-1-yl |
| 141 | 4-fluorophenyl | phenoxy | piperazin-1-yl |
| 142 | 4-fluorophenyl | 2-fluorophenoxy | piperazin-1-yl |
| 143 | 4-fluorophenyl | 3-fluorophenoxy | piperazin-1-yl |
| 144 | 4-fluorophenyl | 4-fluorophenoxy | piperazin-1-yl |
| 145 | 4-fluorophenyl | 2,6-difluorophenoxy | piperazin-1-yl |
| 146 | 4-fluorophenyl | 2-cyanophenoxy | piperazin-1-yl |
| 147 | 4-fluorophenyl | 3-cyanophenoxy | piperazin-1-yl |
| 148 | 4-fluorophenyl | 2-trifluoromethylphenoxy | piperazin-1-yl |
| 149 | 4-fluorophenyl | 4-trifluoromethylphenoxy | piperazin-1-yl |
| 150 | 4-fluorophenyl | 2-methylphenoxy | piperazin-1-yl |
| 151 | 4-fluorophenyl | 4-methylphenoxy | piperazin-1-yl |
| 152 | 4-fluorophenyl | 2,4-dimethylphenoxy | piperazin-1-yl |
| 153 | 4-fluorophenyl | 3-N-acetylaminophenoxy | piperazin-1-yl |
| 154 | 4-fluorophenyl | 2-methoxyphenoxy | piperazin-1-yl |
| 155 | 4-fluorophenyl | 4-methoxyphenoxy | piperazin-1-yl |
| 156 | 4-fluorophenyl | 3-benzo[1,3]dioxol-5-yl | piperazin-1-yl |
| 157 | 4-fluorophenyl | phenoxy | pyrrolidin-1-yl |
| 158 | 4-fluorophenyl | 2-fluorophenoxy | pyrrolidin-1-yl |
| 159 | 4-fluorophenyl | 3-fluorophenoxy | pyrrolidin-1-yl |
| 160 | 4-fluorophenyl | 4-fluorophenoxy | pyrrolidin-1-yl |
| 161 | 4-fluorophenyl | 2,6-difluorophenoxy | pyrrolidin-1-yl |

TABLE III-continued

| No. | R¹ | R³ | $R^{9a}/R^{9b}$ ring |
|---|---|---|---|
| 162 | 4-fluorophenyl | 2-cyanophenoxy | pyrrolidin-1-yl |
| 163 | 4-fluorophenyl | 3-cyanophenoxy | pyrrolidin-1-yl |
| 164 | 4-fluorophenyl | 2-trifluoromethylphenoxy | pyrrolidin-1-yl |
| 165 | 4-fluorophenyl | 4-trifluoromethylphenoxy | pyrrolidin-1-yl |
| 166 | 4-fluorophenyl | 2-methylphenoxy | pyrrolidin-1-yl |
| 167 | 4-fluorophenyl | 4-methylphenoxy | pyrrolidin-1-yl |
| 167 | 4-fluorophenyl | 2,4-dimethylphenoxy | pyrrolidin-1-yl |
| 169 | 4-fluorophenyl | 3-N-acetylaminophenoxy | pyrrolidin-1-yl |
| 170 | 4-fluorophenyl | 2-methoxyphenoxy | pyrrolidin-1-yl |
| 171 | 4-fluorophenyl | 4-methoxyphenoxy | pyrrolidin-1-yl |
| 172 | 4-fluorophenyl | 3-benzo[1,3]dioxol-5-yl | pyrrolidin-1-yl |

The following is a scheme for preparing compounds belonging to the first aspect of Category II according to the present invention. The first stage encompasses utilization of Type III intermediates to introduce the $R^1$ unit (4-fluorophenyl in the present example) into the molecule. Intermediate ketones such as compound 11 can be used in the next sequence to introduce the selected amino unit to the 6-position of the pyrazolo[1,2-a]pyrazol-1-one ring system.

General Scheme for Intermediate Type III

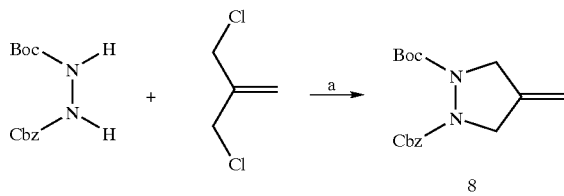

8

Reagents and conditions: (a) NaH, DMF, rt, 12 hr.

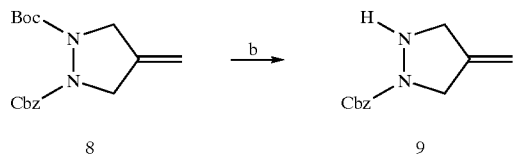

8       9

Reagents and Conditions: (b) SOCl₂, MeOH, 0° C. to rt, 18 hr

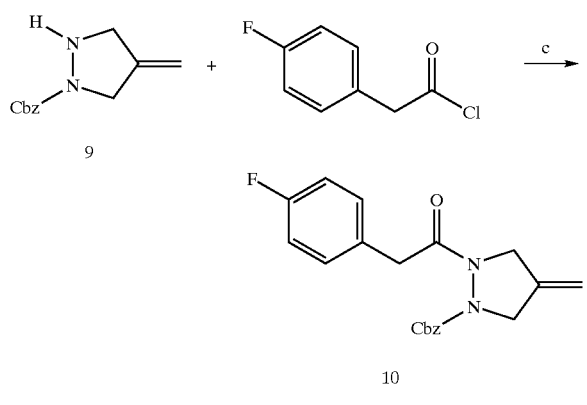

10

Reagents and Conditions: (c) NaOH, CH₂Cl₂/water, rt 18 hr.

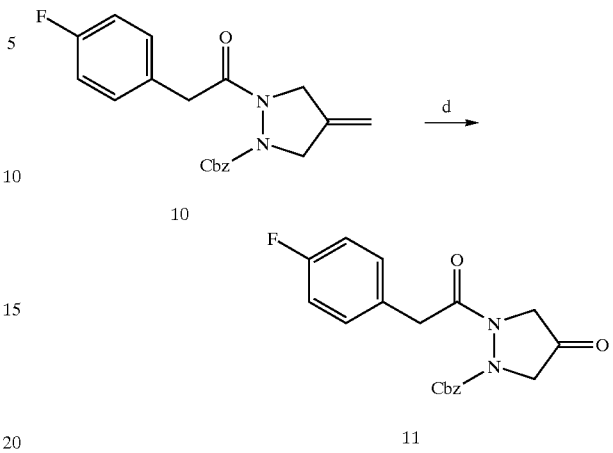

Reagents and Conditions: (d) O₃, CH₂Cl₂, DMS; −78° C. to rt 18 hr.

EXAMPLE 5

2-[2-(4-Fluorophenyl)acetyl]-4-oxo-pyrazolidine-1-carboxylic acid benzyl ester (11)

Preparation of 4-methylenepyrazolidine-1,2-dicarboxylic acid 1-benzyl ester 2-tert-butyl ester (8): To a suspension of NaH (3.81 g, 95.4 mmol) in DMF (80 mL) is add dropwise a solution of N-Cbz-N'-Boc-hydrazine (12.1 g, 45.4 mmol) in DMF (20 mL). The reaction mixture is stirred about 20 minutes and 3-chloro-2chloromethyl-propene (5.8 mL, 50 mmol) is added dropwise and the reaction is allowed to stir at room temperature until the reaction is complete by TLC, approximately 12 hours. The reaction solution is partitioned between ethyl acetate and water, the water layer being extracted several times more with solvent. The combined organic layers are dried, filtered, and concentrated to afford the desired product as a clear oil which is used without further purification.

Preparation of 4-methylene-pyrazolidine-1-carboxylic acid 1-benzyl ester (9): To a solution of crude 4-methylenepyrazolidine-1,2-dicarboxylic acid 1-benzyl ester 2-tert-butyl ester, 8, (30 g) in methanol (300 ml.) is added thionyl chloride dropwise at 0° C. The reaction is warmed to room temperature and stirred an additional 18 hours. Concentration of the reaction in vacuo affords a yellow oil which crystallizes upon standing to provide 23 g (97% yield) of the desired product as the HCl salt.

Preparation of 2-[2-(4-fluorophenyl)acetyl]-4-methylene-pyrazolidine-1-carboxylic acid benzyl ester (10): Sodium hydroxide (0.12 g, 3 mmol) is dissolved in a 1:2 water/methylene chloride solution (30 mL) with rapid stirring followed by the addition of 4-methylene-pyrazolidine-1-carboxylic acid 1-benzyl ester, 9, (0.62 g, 2.8 mmol) at room temperature. (4-Fluorophenyl)acetyl chloride (0.39 mL, 4.2 mmol) is added and the reaction is allowed to stir for 18 hours after which time the reaction mixture is diluted with water (10 mL) and the layers allowed to separate. The aqueous layer is extracted with methylene chloride, the organic layers combined, dried, and filtered. Concentration in vacuo affords the crude product which is purified over silica (1:3 ethyl acetate/hexane) to provide 0.54 g (62% yield) of the desired product.

Preparation of 2-[2-(4fluorophenyl)acetyl]-4-oxo-pyrazolidine-1-carboxylic acid benzyl ester (11): Ozone gas is bubbled into a solution of 2-[2-(4-fluorophenyl)-acetyl] 4-methylene-pyrazolidine-1-carboxylic acid benzyl ester, 10, (0.28 g, 0.8 mmol) in methylene chloride (15 mL) at −78° C. until the solution retains a blue color. The source of ozone is removed and dimethyl sulfoxide (0.23 mL) is added and the reaction solution allowed to warm to room temperature and stir for 18 hours. The solvent is removed in vacuo and the resulting oil purified over silica (1:3 ethyl acetate/hexane) to afford 0.15 g (53% yield) of the desired product as a clear oil.

Synthetic intermediates of Type III, for example, compound 11, can be used as a template for introducing the desired 6-position amino moiety as outlined in the example below.

General Scheme Type IV Intermediates

Introduction of a 6-amino unit into the scaffold of compounds encompassing the first aspect of Category II analogs.

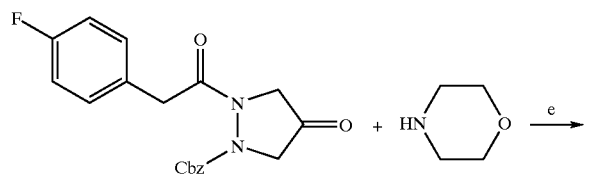

11

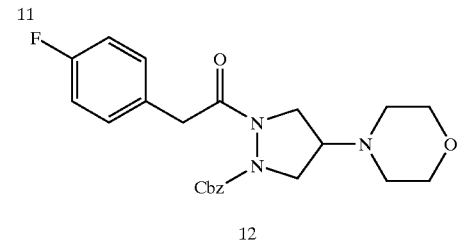

12

Reagents and conditions: (e) Na(OAc)$_3$BH, HOAc, THF; rt 12 hr.

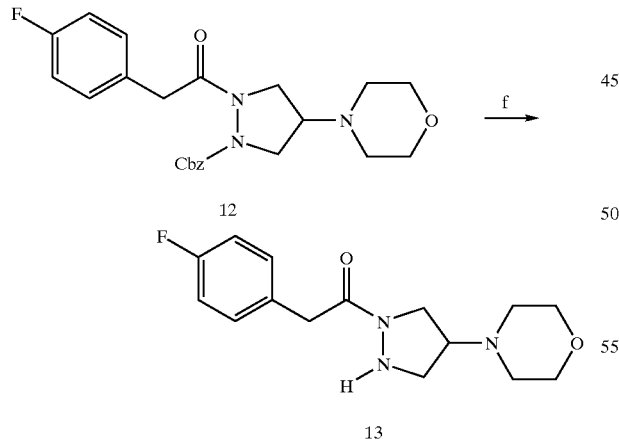

13

Reagents and conditions: (f) H$_2$; Pd/C, MeOH.

EXAMPLE 6

2-(4-Fluorophenyl)-1-(4-morpholin-4-yl-pyrazolidin-1-yl)-ethanone (13)

Preparation of 2-[2-(4-fluorophenyl)acetyl]-4-morpholin-4-yl-pyrazolidine-1-carboxylic acid benzyl ester (12): To a solution of 2-[2-(4-fluorophenyl)acetyl]-4-oxo-pyrazolidine-1-carboxylic acid benzyl ester, 11, (0.14 g, 0.4 mmol) and morpholine (0.038 mL, 0.43 mmol) in THF at room temperature is added Na(OAc)$_3$BH (0.125 g, 0.6 mmol) and HOAc (0.022 mL, 0.4 mmol). The solution is stirred 12 hours then partitioned between diethyl ether and NaHCO$_3$. The aqueous layer was extracted several times with ether and the organic layers combined, dried, and concentrated in vacuo to a clear oil which was re-dissolved in ether and one equivalent of ethereal HCl is added and a white solid forms. The solid is collected by filtration and 100 mg (60% yield) of the desired product is isolated as the HCl salt.

Preparation of 2-(4-Fluorophenyl)-1-(4-morpholin-4-yl-pyrazolidin-1-yl)-ethanone (13): 2-[2-(4-Fluorophenyl) acetyl[4-morpholin4-yl-pyrazolidine-1-carboxylic acid benzyl ester HCl salt, 12, (100 mg, 0.2 mmol) is dissolved in methanol and Pd/C (5 mg) is added. The solution is then hydrogenated in a Parr® Hydrogenation Apparatus for 3 days after which time the catalyst is removed by filtration and the filtrate concentrated in vacuo to afford 55 mg (81% yield) of the desired product as a tan solid.

Once the selected 6-amino unit is in position on the 2-R$^1$-substituted-pyrazolo[1,2-a]pyrazol-1-one scaffold, segments of the final analogs which comprise the selected R units can be assembled utilizing a convergent synthetic step. This step makes use of Intermediate Type V compounds having the general formula:

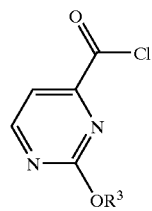

thereby introducing the desired —OR$^3$ unit into the scaffold, said Type V intermediates can be prepared according to the procedure outlined in the scheme herein below.

General Scheme for Intermediate Type V

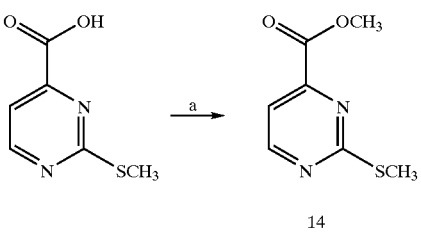

14

Reagents and conditions: (a) SOCl$_2$, MeOH; rt 12 hr.

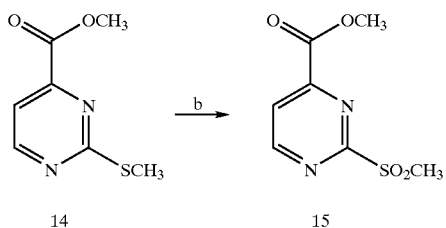

Reagents and conditions: (b) Oxone®, MeOH/THF/H$_2$O; rt 12 hr.

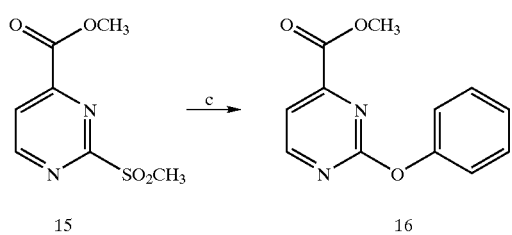

Reagents and conditions: (c) phenol, NaH, THF; rt 12 hr.

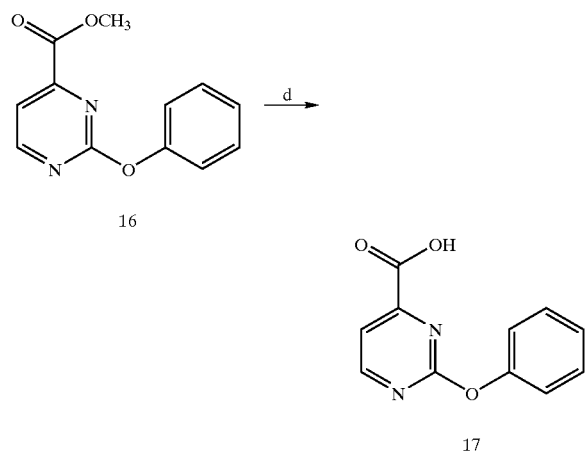

Reagents and conditions: (d) NaOH MeOH/H$_2$O: rt 1.5 hr.

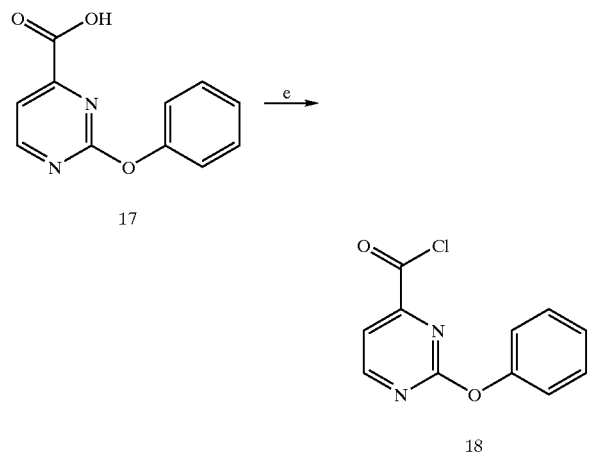

Reagents and conditions: (e) oxalyl chloride, CH$_2$Cl$_2$/DMF; rt 2 hr.

EXAMPLE 7

2-Phenoxy-pyrimidine-4-carbonyl chloride (18)

Preparation of 2-methylsulfanyl-pyrimidine-4-carboxylic acid methyl ester (14): To a suspension of 2-methylsulfanyl-pyrimidine4-carboxylic acid (15 g, 88 mmol) in methanol (200 mL) is added dropwise thionyl chloride (25 mL). The solution is allowed to warm to room temperature and stir 12 hours. The solution is then concentrated in vacuo and the yellow solid which remains can be taken up in methylene chloride and reconcentrated to afford 19 g (97% yield) of the HCl salt of the desired product as a white solid.

Preparation of 2-methanesulfonyl-pyrimidine-4-carboxylic acid methyl ester (15): An aqueous solution (1 L) of Oxone® (211.7 g, 344 mmol) is added dropwise at 0° C. to a solution of 2-methyl-sulfanyl-pyrimidine-4-carboxylic acid methyl ester, 14, (19 g,86.1 mmol) in 1:1 methanol/THF (1 L). The reaction solution is allowed to warm to room temperature and stir for 1.5 hours. The resulting suspension is partitioned between methylene chloride and water. The aqueous phase is made alkaline with the addition of NaOH and re extracted with solvent. The combined organic layers are dried, filtered, and concentrated in vacuo to afford 18.4 g of the desired product as a yellow oil.

Preparation of 2-phenoxy-pyrimidine-4-carboxylic acid methyl ester (16): NaH (3.5 g of a 60% suspension, 87.4 mmol) is added to a solution of phenol (8.23 g, 87.4 mmol) in THF (100 mL) at room temperature. 2-Methanesulfonyl-pyrimidine-4-carboxylic acid methyl ester, 15, (6.3 g, 29.1 mmol) is dissolved in THF (60 mL) and added dropwise to the solution of phenol. The reaction is allowed to stir for 12 hours then quenched by the addition of saturated aqueous NH$_4$Cl. The aqueous phase is extracted with methylene chloride and the combined organic layers are dried, filtered, and concentrated in vacuo to afford a crude oil which is purified over silica (ethyl acetate/hexane 2:3) to afford 1.72 g (25% yield) of the desired product as a white solid.

Preparation of 2-phenoxy-pyrimidine-4-carboxylic acid (17): To a solution of 2-phenoxy-pyrimidine-4-carboxylic acid methyl ester, 16, (1.72 g, 74.8 mmol) in methanol (50 mL) is added a 50% NaOH solution (10 mL) at room temperature. After stirring for 1.5 hours the solvent is removed in vacuo and the remaining aqueous phase is extracted with ethyl acetate. The aqueous phase can then be carefully acidified with concentrated HCl and the white solid which forms extracted twice with ethyl acetate. The organic layers are combined, dried and concentrated in vacuo to afford 0.95 g (60% yield) of the desired product as a white solid.

Preparation of 2-phenoxy-pyrimidine-4-carbonyl chloride (18): To a solution of 2-phenoxy-pyrimidine-4-carboxylic acid, 17, (0.19 g, 0.89 mmol) in methylene chloride (10 mL) containing a few drops of DMF is added oxalyl chloride (0.1 mL). The solution is stirred for 2 hours at room temperature and concentrated in vacuo to afford the desired product which is used without further purification.

The final sequence for preparing the compounds which comprise the first aspect of Category II analogs according to the present invention can be accomplished by the procedure outlined herein below. This procedure involves a convergent step wherein the first half comprises the selected R[1] unit and the 6-position amino unit, for example, as intermediate 13, while the second half comprises the final R unit already introduced to the pyrimidine ring, for example, as in intermediate 18.

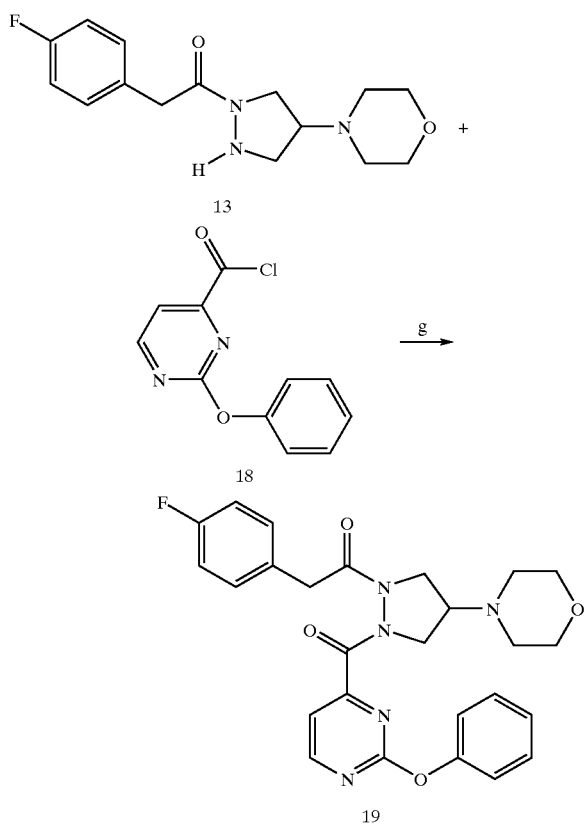

Reagents and Conditions: (g) NaOH: CH$_2$Cl$_2$/water, rt 12 hr.

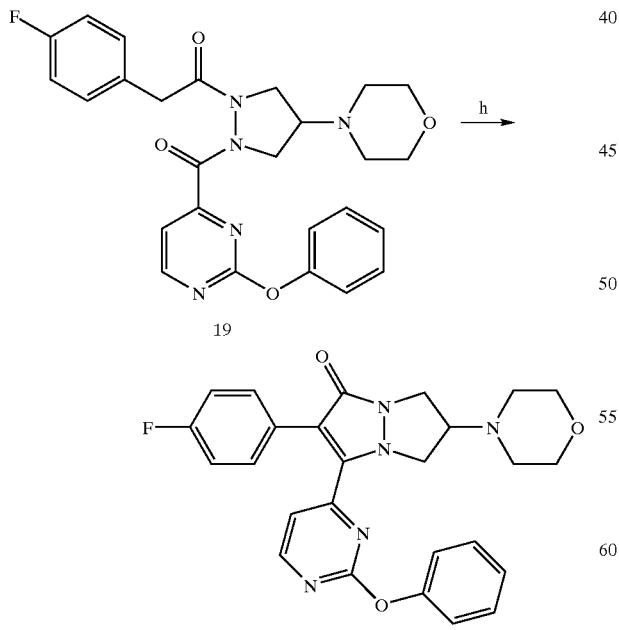

Reagents and Conditions: (h) NaH, DMF; 0° C., 2 hr.

EXAMPLE 8

2-(4-Fluorophenyl)-6-morpholin-4-yl-3-(2-phenoxy-pyrimidin-4-yl)-6,7-dihydro-5H-pyrazolo[1,2-a]pyrazol-1-one (20)

Preparation of 2-(fluorophenyl)-1-[4-morpholin-4-yl-2-(2-phenoxy-pyrimidine-4-carbonyl)pyrazolidine-1-yl] ethanone (19): 2-Phenoxypyrimidine-4carbonyl chloride, 18, (0.07 g, 0.28 mmol) in methylene chloride (1.5 mL) is added dropwise to a suspension of 2-(4-fluorophenyl)-1-(4-morpholin4-yl-pyrazolidin-1-yl)ethanone,13, (0.06 g, 0.18 mmol) in a 2:5 water/CH$_2$Cl$_2$ solution (7 mL) containing NaOH (0.0112 g 0.28 mmol) at room temperature. The solution is stirred 18 hours and diluted with additional 2:5 water/CH$_2$Cl$_2$. The layers are allowed to separate and the aqueous phase extracted with additional methylene chloride. The organic layers are combined, dried, filtered and concentrated in vacuo to afford a tan solid which is purified by preparative HPLC to provide 0.021 g (23% yield) of the desired product as an oily solid.

Preparation of 2-(4-fluorophenyl)-6-morpholin-4-yl-3-(2-phenoxy-pyrimidin-4-yl)-6,7-dihydro-5H-pyrazolo[1,2-a] pyrazol-1-one (20): To a solution of 2-(4-fluorophenyl)-1-[4-morpholin-4-yl-2-(2-phenoxy-pyrimidine-4-carbonyl) pyrazolidine-1-yl]ethanone, 19, (0.2 g, 0.4 mmol) in DMF (10 mL) at 0° C. is added NaH (0.024 g. 0.6 mmol) and the resulting solution is stirred 2 hours. The solvent is removed in vacuo the residue dissolved in methylene chloride and extracted with water, dried, and re-concentrated to afford 37 mg (20% yield) of the desired product as a yellow solid.

The following compounds from the first aspect of Category II can be prepared by the procedure described herein above.

2-(4-Fluorophenyl)-6-morpholin-4-yl-3-[2-(4-fluorophenoxy)-pyrimidin-4-yl]-6,7-dihydro-5H-pyrazolo[1,2-a]pyrazol-1-one: $^1$H NMR (CDCl$_3$, 300 MHz) □ 1.61 (s, 4H), 2.58 (s, 4H), 3.70–3.99 (m, 4H), 4.234–25 (m, 1H), 6.94 (d, 1H, J=5.1 Hz), 7.10 (t, 2H, J=8.7 Hz), 7.26–7.41 (m, 6H), 8.50 (d, 1H, J=5.1 Hz). ESI$^+$ MS: m/z (rel intensity) 491.9 (100, M$^+$+H). Anal. Calculated for C$_{26}$H$_{23}$F$_2$N$_5$O$_3$ 0.5H$_2$O: C, 62.39; H, 4.83; N, 13.99. Found: C, 62.02; H, 4.38; N, 13.62.

The second aspect of Category II analogs relates to compounds having the formula:

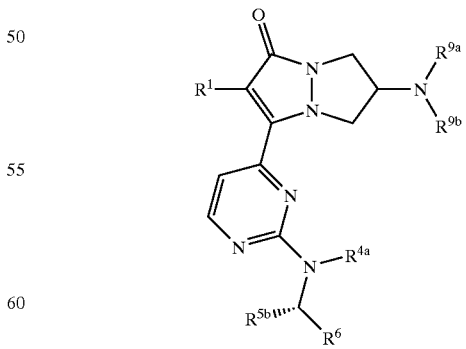

wherein R is an amino unit as indicated in the formula. The analogs of Table IV comprise R units having the formula —NHC(HR$^{5b}$)R$^6$ wherein R$^{4a}$ is hydrogen and R$^1$, R$^{5a}$, R$^6$, R$^{9a}$, and R$^{9b}$ are described herein.

TABLE IV

| No. | R¹ | R⁵ᵇ | R⁶ | R⁹ᵃ | R⁹ᵇ |
|---|---|---|---|---|---|
| 173 | 4-fluorophenyl | H | phenyl | H | H |
| 174 | 4-fluorophenyl | H | 4-fluorophenyl | H | H |
| 175 | 4-fluorophenyl | H | 2-aminophenyl | H | H |
| 176 | 4-fluorophenyl | H | 2-methylphenyl | H | H |
| 177 | 4-fluorophenyl | H | 4-methylphenyl | H | H |
| 178 | 4-fluorophenyl | H | 4-methoxyphenyl | H | H |
| 179 | 4-fluorophenyl | H | 4-(propanesulfonyl)phenyl | H | H |
| 180 | 4-fluorophenyl | H | 3-benzo[1,3]dioxol-5-yl | H | H |
| 181 | 4-fluorophenyl | H | pyridin-2-yl | H | H |
| 182 | 4-fluorophenyl | H | pyridin-3-yl | H | H |
| 183 | 4-fluorophenyl | methyl | phenyl | H | H |
| 184 | 4-fluorophenyl | methyl | 4-fluorophenyl | H | H |
| 185 | 4-fluorophenyl | methyl | 2-aminophenyl | H | H |
| 186 | 4-fluorophenyl | methyl | 2-methylphenyl | H | H |
| 187 | 4-fluorophenyl | methyl | 4-methylphenyl | H | H |
| 188 | 4-fluorophenyl | methyl | 4-methoxyphenyl | H | H |
| 189 | 4-fluorophenyl | methyl | 4-(propanesulfonyl)phenyl | H | H |
| 190 | 4-fluorophenyl | methyl | 3-benzo[1,3]dioxol-5-yl | H | H |
| 191 | 4-fluorophenyl | methyl | pyridin-2-yl | H | H |
| 192 | 4-fluorophenyl | methyl | pyridin-3-yl | H | H |
| 193 | 4-fluorophenyl | H | phenyl | methyl | methyl |
| 194 | 4-fluorophenyl | H | 4-fluorophenyl | methyl | methyl |
| 195 | 4-fluorophenyl | H | 2-aminophenyl | methyl | methyl |
| 196 | 4-fluorophenyl | H | 2-methylphenyl | methyl | methyl |
| 197 | 4-fluorophenyl | H | 4-methylphenyl | methyl | methyl |
| 198 | 4-fluorophenyl | H | 4-methoxyphenyl | methyl | methyl |
| 199 | 4-fluorophenyl | H | 4-(propanesulfonyl)phenyl | methyl | methyl |
| 200 | 4-fluorophenyl | H | 3-benzo[1,3]dioxol-5-yl | methyl | methyl |
| 201 | 4-fluorophenyl | H | pyridin-2-yl | methyl | methyl |
| 202 | 4-fluorophenyl | H | pyridin-3-yl | methyl | methyl |
| 203 | 4-fluorophenyl | methyl | phenyl | methyl | methyl |
| 204 | 4-fluorophenyl | methyl | 4-fluorophenyl | methyl | methyl |
| 205 | 4-fluorophenyl | methyl | 2-aminophenyl | methyl | methyl |
| 206 | 4-fluorophenyl | methyl | 2-methylphenyl | methyl | methyl |
| 207 | 4-fluorophenyl | methyl | 4-methylphenyl | methyl | methyl |
| 208 | 4-fluorophenyl | methyl | 4-methoxyphenyl | methyl | methyl |
| 209 | 4-fluorophenyl | methyl | 4-(propanesulfonyl)phenyl | methyl | methyl |
| 210 | 4-fluorophenyl | methyl | 3-benzo[1,3]dioxol-5-yl | methyl | methyl |
| 211 | 4-fluorophenyl | methyl | pyridin-2-yl | methyl | methyl |
| 212 | 4-fluorophenyl | methyl | pyridin-3-yl | methyl | methyl |
| 213 | 4-fluorophenyl | —CO₂CH₃ | phenyl | H | H |
| 214 | 4-fluorophenyl | —CO₂CH₃ | 4-fluorophenyl | H | H |
| 215 | 4-fluorophenyl | —CO₂CH₃ | 2-aminophenyl | H | H |
| 216 | 4-fluorophenyl | —CO₂CH₃ | 2-methylphenyl | H | H |
| 217 | 4-fluorophenyl | —CO₂CH₃ | 4-methylphenyl | H | H |
| 218 | 4-fluorophenyl | —CO₂CH₃ | 4-methoxyphenyl | H | H |
| 219 | 4-fluorophenyl | —CO₂CH₃ | 4-(propanesulfonyl)phenyl | H | H |
| 220 | 4-fluorophenyl | —CO₂CH₃ | 3-benzo[1,3]dioxol-5-yl | H | H |
| 221 | 4-fluorophenyl | —CO₂CH₃ | pyridin-2-yl | H | H |
| 222 | 4-fluorophenyl | —CO₂CH₃ | pyridin-3-yl | H | H |
| 223 | 4-fluorophenyl | —CO₂CH₃ | phenyl | methyl | methyl |
| 224 | 4-fluorophenyl | —CO₂CH₃ | 4-fluorophenyl | methyl | methyl |
| 225 | 4-fluorophenyl | —CO₂CH₃ | 2-aminophenyl | methyl | methyl |
| 226 | 4-fluorophenyl | —CO₂CH₃ | 2-methylphenyl | methyl | methyl |
| 227 | 4-fluorophenyl | —CO₂CH₃ | 4-methylphenyl | methyl | methyl |
| 228 | 4-fluorophenyl | —CO₂CH₃ | 4-methoxyphenyl | methyl | methyl |
| 229 | 4-fluorophenyl | —CO₂CH₃ | 4-(propanesulfonyl)phenyl | methyl | methyl |
| 230 | 4-fluorophenyl | —CO₂CH₃ | 3-benzo[1,3]dioxol-5-yl | methyl | methyl |
| 231 | 4-fluorophenyl | —CO₂CH₃ | pyridin-2-yl | methyl | methyl |
| 232 | 4-fluorophenyl | —CO₂CH₃ | pyridin-3-yl | methyl | methyl |

The compounds which comprise the second aspect of Category II analogs wherein R is an amino unit, can be prepared by the Scheme outlined herein below starting with common intermediate 11. For the following example $R^{9a}$ and $R^{9b}$ are each methyl and R is (S)-(1-phenyl)ethylamino.

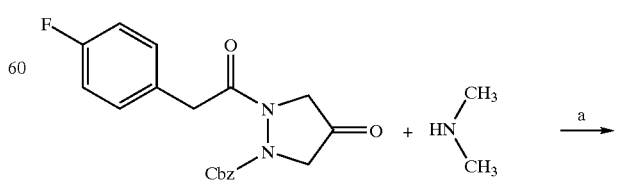

11

-continued
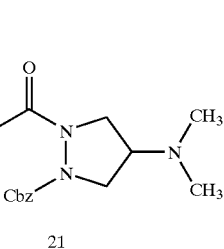
21
Reagents and Conditions: (a) Na(OAc)₃BH, HOAc, THF; rt 12 hr.
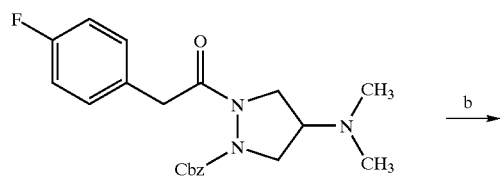
21
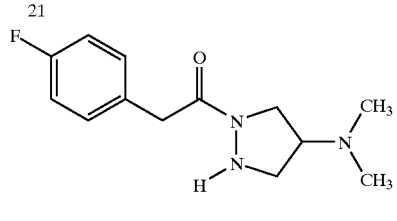
22
Reagents and Conditions: (b) H₂; Pd/C, MeOH.
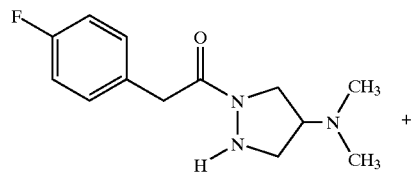
22
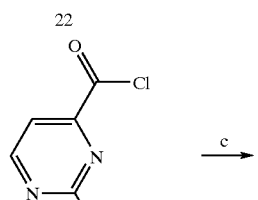
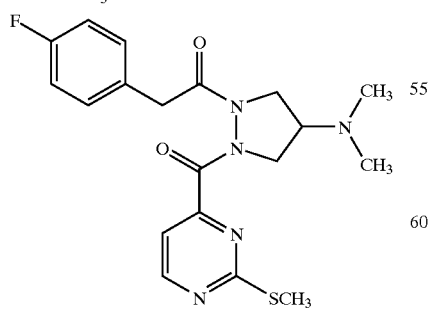
23
Reagents and Conditions: (c) NaOH: CH₂Cl₂/water, rt 12 hr.
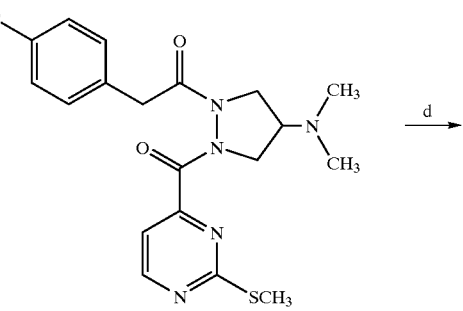
23
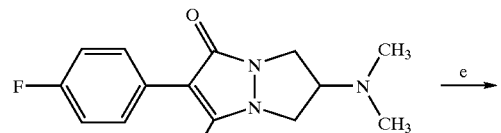
24
Reagents and Conditions: (d) NaH, DMF; 0° C. to rt, 2 hr.
24
25
Reagents and Conditions: (e) Oxone®, MeOH/THF/H2O, rt 12 hr.
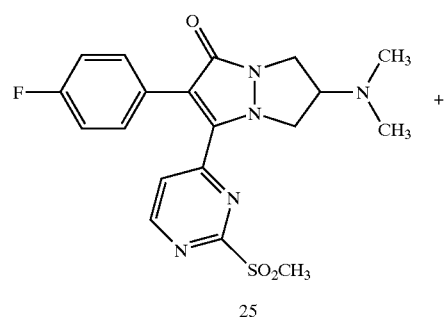
25

-continued

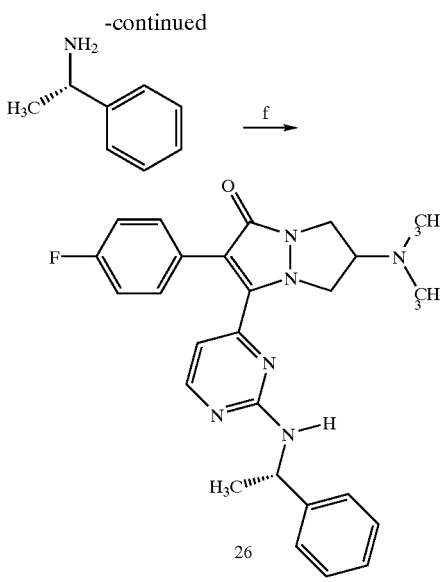

Reagents and Conditions: (f) toluene, 140° C., 12 hr.

EXAMPLE 9

6-Dimethylamino-2-(4-fluorophenyl)-3-[2-(1-phenylethylamino)pyrimidin-4-yl]-6,7-dihydro-5H-pyrazolo[1,2-a]pyrazol-1-one (26)

Preparation of 4dimethylamino-2-[2-(4-fluorophenyl) acetyl]-pyrazolidine-1-carboxylic acid benzyl ester (21): To a solution of 2-[2-(4-fluorophenyl)acetyl]-4oxo-pyrazolidine-1-carboxylic acid benzyl ester, 11, (3.6 g, 10 mmol) and dimethylamine (10 mL of a 2M solution, 20 mmol) in THF at room temperature is added Na(OAc)$_3$BH (3.1 g, 15 mmol) and HOAc (0.6 g, 10 mmol). The solution is stirred 12 hours then partitioned between diethyl ether and NaHCO$_3$. The aqueous layer was extracted several times with ether and the organic layers combined, dried, and concentrated in vacuo to a clear oil which was re-dissolved in ether and one equivalent of ethereal HCl is added and a white solid forms. The solid is collected by filtration to afford the desired product as the HCl salt.

Preparation of 1-(4-dimethylamino-pyrazolidin-1-yl)-2-(4-fluorophenyl)-ethanone (22): 4-dimethylamino-2-[2-(4-fluorophenyl)acetyl]-pyrazolidine-1-carboxylic acid benzyl ester HCl salt, 21, (4.22 g, 10 mmol) is dissolved in methanol and Pd/C (100 mg) is added. The solution is then hydrogenated of a Parr® Hydrogenation Apparatus 18 hours after which time the catalyst is removed by filtration and the filtrate concentrated in vacuo to afford the desired product.

Preparation of 1-[4-dimethylamino-2-(2-methylsulfanyl-pyrimidine-4-carbonyl)-pyrazolidin-1-yl]-2-(4-fluorophenyl)-ethanone (23): To a solution of 1-(4-dimethylamino-pyrazolidin-1-yl)-2-(4-fluorophenyl)-ethanone, 22, (2.5 g, 10 mmol) in dichloromethane (20 mL) is added 2-methylsulfonyl-pyrimidine-4-carbonyl chloride (3.7 g, 20 mmol) followed by dropwise addition of a 1.0 N aqueous solution of sodium hydroxide (35 mL). The mixture is vigorously stirred at room temperature for 12 hours. The reaction is diluted with dichloromethane (100 mL) and washed with water (100 mL). The aqueous layer is back-extracted with dichloromethane (100 mL). The combined organic layers are washed with a saturated aqueous solution of sodium bicarbonate (100 mL) and brine (100 mL), dried, filtered and concentrated in vacuo. The resulting crude material is purified over silica (1:1 hexane/ethyl acetate to 100% ethyl acetate) to afford the desired product.

Preparation of 6-dimethylamino-2-(4-fluorophenyl)-3-(2-methylsulfanyl-pyrimidin-4-yl)-6,7-dihydro-5H-pyrazolo[1,2-a]pyrazol-1-one (24): 1-[4-Dimethylamino-2-(2-methylsulfanyl-pyrimidine-4-carbonyl)-pyrazolidin-1-yl]-2-(4-fluorophenyl)-ethanone, 23, (4.0 g, 10 mmol) is dissolved in THF (75 mL). This solution is then added dropwise via cannula to a suspension of NaH (0.440 g of a 60% dispersion in mineral oil, 11 mmol) at −30° C. The reaction is allowed to gradually warm to 0° C. over 3 hours. The reaction is quenched with NH$_4$Cl (sat. aq.) (15 ml ). The mixture is stirred at room temperature, then concentrated in vacuo. The residue is diluted with tetrahydrofuran (250 mL) and the mixture filtered through Celite. The filtrate is concentrated in vacuo to give an oil. The crude product is purified over silica (100% ethyl acetate to 5% to 10% to 20% methyl alcohol/ethyl acetate) to afford the desired product.

Preparation of 6-dimethylamino-2-(4-fluorophenyl)-3-(2-methanesulfonyl-pyrimidin-4-yl)-6,7-dihydro-5H-pyrazolo[1,2-a]pyrazol-1-one (25): To a solution of 6-dimethylamino-2-(4-fluorophenyl)-3-(2-methylsulfanyl-pyrimidin-4-yl)-6,7-dihydro-5H-pyrazolo[1,2-a]pyrazol-1-one, 24, (3.9 g, 10 mmol) in THF:methanol (150 mL of a 1:1 mixture) is added dropwise a solution of Oxone® (potassium peroxymonosulfate) (24.3 g, 39.5 mmol) in water (100 mL). The reaction is stirred 1 hour at room temperature, diluted with aqueous NaHCO$_3$ and extract three times with ethyl acetate. The organic layers are combined, dried, and concentrated in vacuo to afford the crude desired product which is used without further purification.

Preparation of 6-dimethylamino-2-(4fluorophenyl)-3-[2-(1-(S)-phenylethylamino)-pyrimidin-4-yl]-6,7-dihydro-5H-pyrazolo[1,2a]pyrazol-1-one (26): A solution of the crude 6-dimethylamino-2-(4-fluorophenyl)-3-(2-methanesulfonyl-pyrimidin-4-yl)-6,7dihydro-5H-pyrazolo[1,2-a]pyrazol-1-one, 25, prepared as described herein above (4.2 g, 10 mmol) and (S)-(-)-□-methyl-benzyl amine (45.2 mL, 351 mmol) are dissolved in toluene (100 mL). The resulting mixture is heated to 140° C. for 12 hours, cooled to room temperature and the solvent removed in vacuo. The resulting residue is purified over silica (1:1 EtOAc/hexanes) to afford the desired product.

Category III of inflammatory cytokine release inhibiting compounds according to the present invention have the general scaffold having the formula:

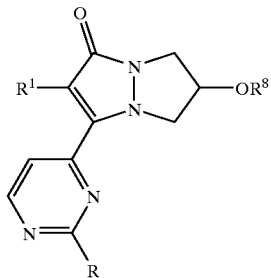

the first aspect of which relates to ether analogs having the formula:

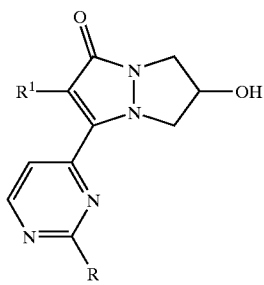

wherein R and R¹ units are defined herein below in Table IV.

TABLE IV

| No. | R¹ | R |
|---|---|---|
| 233 | 4-fluorophenyl | phenoxy |
| 234 | 4-fluorophenyl | 2-fluorophenoxy |
| 235 | 4-fluorophenyl | 3-fluorophenoxy |
| 236 | 4-fluorophenyl | 4-fluorophenoxy |
| 237 | 4-fluorophenyl | 2,6-difluorophenoxy |
| 238 | 4-fluorophenyl | 2-cyanophenoxy |
| 239 | 4-fluorophenyl | 3-cyanophenoxy |
| 240 | 4-fluorophenyl | 2-trifluoromethylphenoxy |
| 241 | 4-fluorophenyl | 4-trifluoromethylphenoxy |
| 242 | 4-fluorophenyl | 2-methylphenoxy |
| 243 | 4-fluorophenyl | 4-methylphenoxy |
| 244 | 4-fluorophenyl | 2,4-dimethylphenoxy |
| 245 | 4-fluorophenyl | 3-N-acetylaminophenoxy |
| 246 | 4-fluorophenyl | 2-methoxyphenoxy |
| 247 | 4-fluorophenyl | 4-methoxyphenoxy |
| 248 | 4-fluorophenyl | 3-benzo[1,3]dioxol-5-yl |
| 249 | 3-fluorophenyl | phenoxy |
| 250 | 3-fluorophenyl | 2-fluorophenoxy |
| 251 | 3-fluorophenyl | 3-fluorophenoxy |
| 252 | 3-fluorophenyl | 4-fluorophenoxy |
| 253 | 3-fluorophenyl | 2,6-difluorophenoxy |
| 254 | 3-fluorophenyl | 2-cyanophenoxy |
| 255 | 3-fluorophenyl | 3-cyanophenoxy |
| 256 | 3-fluorophenyl | 2-trifluoromethylphenoxy |
| 257 | 3-fluorophenyl | 4-trifluoromethylphenoxy |
| 258 | 3-fluorophenyl | 2-methylphenoxy |
| 259 | 3-fluorophenyl | 4-methylphenoxy |
| 260 | 3-fluorophenyl | 2,4-dimethylphenoxy |
| 261 | 3-fluorophenyl | 3-N-acetylaminophenoxy |
| 262 | 3-fluorophenyl | 2-methoxyphenoxy |
| 263 | 3-fluorophenyl | 4-methoxyphenoxy |
| 264 | 3-fluorophenyl | 3-benzo[1,3]dioxol-5-yl |
| 265 | 3-trifluoromethylphenyl | phenoxy |
| 266 | 3-trifluoromethylphenyl | 2-fluorophenoxy |
| 267 | 3-trifluoromethylphenyl | 3-fluorophenoxy |
| 268 | 3-trifluoromethylphenyl | 4-fluorophenoxy |
| 269 | 3-trifluoromethylphenyl | 2,6-difluorophenoxy |
| 270 | 3-trifluoromethylphenyl | 2-cyanophenoxy |
| 271 | 3-trifluoromethylphenyl | 3-cyanophenoxy |
| 272 | 3-trifluoromethylphenyl | 2-trifluoromethylphenoxy |
| 273 | 3-trifluoromethylphenyl | 4-trifluoromethylphenoxy |
| 274 | 3-trifluoromethylphenyl | 2-methylphenoxy |
| 275 | 3-trifluoromethylphenyl | 4-methylphenoxy |
| 276 | 3-trifluoromethylphenyl | 2,4-dimethylphenoxy |
| 277 | 3-trifluoromethylphenyl | 3-N-acetylaminophenoxy |
| 278 | 3-trifluoromethylphenyl | 2-methoxyphenoxy |
| 279 | 3-trifluoromethylphenyl | 4-methoxyphenoxy |
| 280 | 3-trifluoromethylphenyl | 3-benzo[1,3]dioxol-5-yl |

The compounds which comprise the first aspect of the Category III compounds can be prepared by the scheme outline below utilizing intermediate 8 as a convenient starting material.

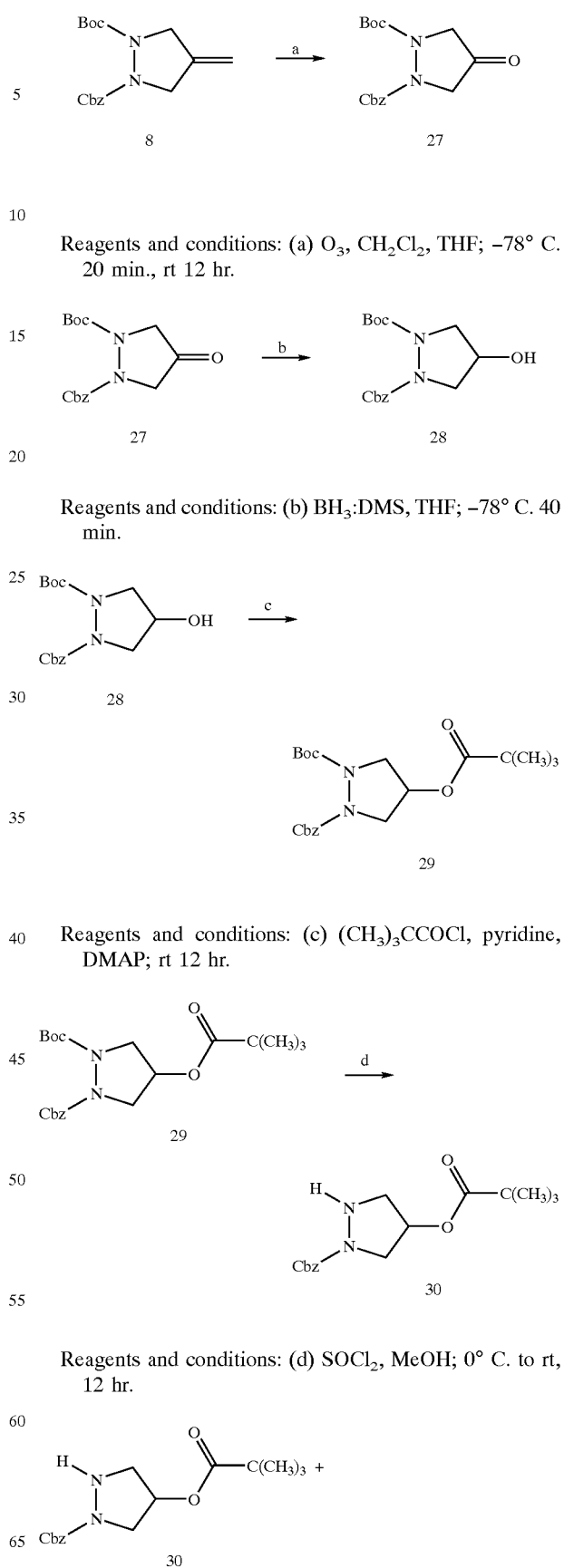

Reagents and conditions: (a) O₃, CH₂Cl₂, THF; −78° C. 20 min., rt 12 hr.

Reagents and conditions: (b) BH₃:DMS, THF; −78° C. 40 min.

Reagents and conditions: (c) (CH₃)₃CCOCl, pyridine, DMAP; rt 12 hr.

Reagents and conditions: (d) SOCl₂, MeOH; 0° C. to rt, 12 hr.

41
-continued
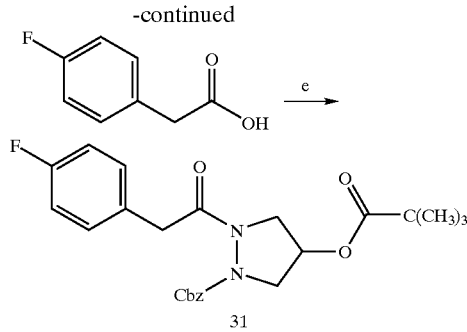
31
Reagents and conditions: (e) Et$_3$N at 0° C.; RCO$_2$H at rt; EDCI, CH$_2$Cl$_2$, 0° C. to rt, 12 hr.
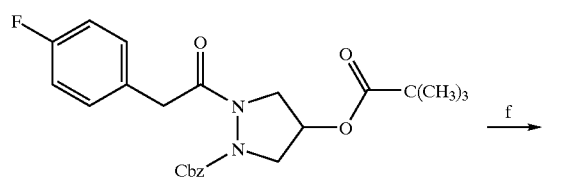
31
Reagents and conditions: (f) H$_2$: Pd/C, MeOH; rt 6 hr.
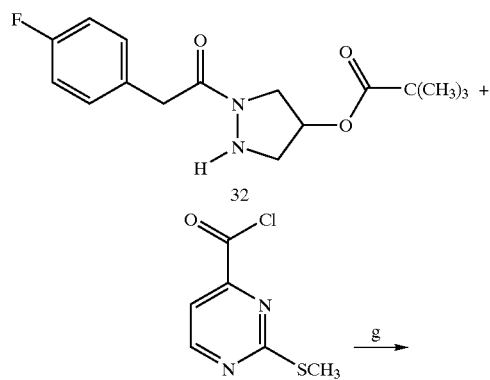
32
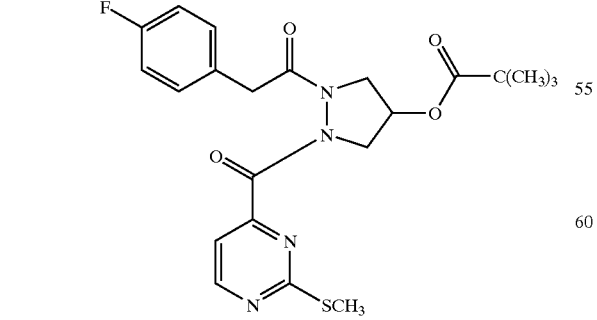
33
42
Reagents and Conditions: (g) NaOH: CH$_2$Cl$_2$/water, rt 12 hr.
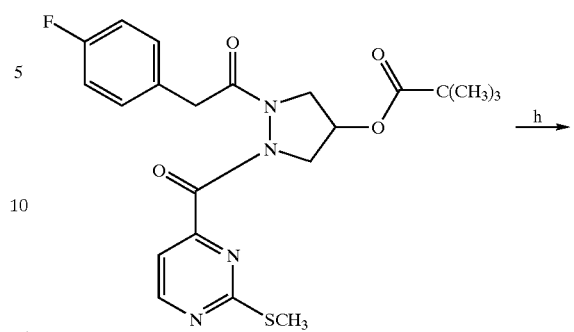
33
34
Reagents and Conditions: (h) NaH, DMF; 0° C. to rt, 3 hr.
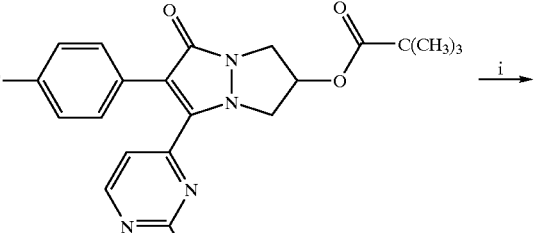
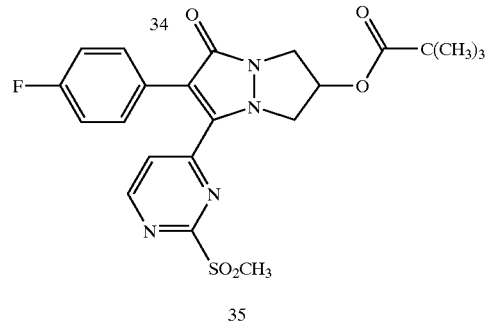
35
Reagents and Conditions: (i) Oxone®, MeOH/THF/H$_2$O; rt 12 hr.
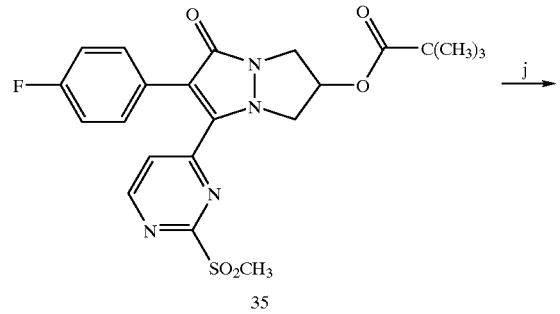
35

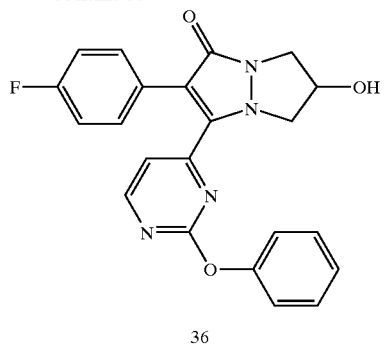

Reagents and Conditions: (j) phenol, base, 0° C. to rt 1 hr.

EXAMPLE 10

2-(4-Fluorophenyl)-6-hydroxy-3-(2-phenoxypyrimidin-4-yl)-6,7-dihydro-5H-pyrazolo[1,2a]pyrazol-1-one (36)

Preparation of 4-oxopyrazolidine-1,2-dicarboxylic acid 1-benzyl ester 2-tert-butyl ester (27): 4-methylene-pyrazolidine-1,2-dicarboxylic acid 1-benzyl ester 2-tert-butyl ester, 8, (23.9 g, 75.1 mmol) is dissolved in dichloromethane (200 mL). The solution is cooled to −78° C. and purged with oxygen for 5 minutes. Ozone gas is passed through the solution until a deep blue color persists in the solution (approx. 20 minutes). The solution is purged with oxygen and argon, and then charged with 40 mL of dimethylsulfide. The cooling bath is removed, and the solution stirred at ambient temperature for 12 hours. The reaction solution is then concentrated in vacuo and the resulting oil purified over silica (3:1 to 2:1 hexane/ethyl acetate) to afford 13.5 g (56% yield).of the desired product as a viscous, clear oil Preparation of 4-hydroxypyrazolidine-1,2-dicarboxylic acid 1-benzyl ester 2-tert-butyl ester (28): 4-Oxo-pyrazolidine-1,2-dicarboxylic acid 1-benzyl ester 2-tert-butyl ester, 27, (5.0 g, 15.6 mmol) is dissolved in tetrahydrofuran (150 mL) and the solution cooled to −78° C. A 5.0 M solution of borane-dimethyl sulfide complex in ether (6.24 mL, 31.2 mmol) is added dropwise via syringe. After 40 minutes at −78° C., the reaction is quenched by slow addition of a saturated aqueous solution of ammonium chloride (20 mL) The cooling bath is removed, and the mixture allowed to warm to ambient temperature with vigorous stirring. The solvent is removed in vacuo and the residue diluted with dichloromethane (200 mL). The mixture is washed with water (150 mL) and saturated aqueous sodium bicarbonate solution (150 mL), water and brine. The combined aqueous layers are extracted with dichloromethane (200 mL), water (150 mL), NaCl (sat.) (200 mL), dried over sodium sulfate, filtered and concentrated in vacuo to afford 4.66 g (93% yield) of the desired product as a clear, viscous oil.

Preparation of 4-(2,2-dimethylpropionyloxy) pyrazolidine-1,2-dicarboxylic acid 1-benzyl ester 2-tert-butyl ester (29): 4-Hydroxypyrazolidine-1,2-dicarboxylic acid 1-benzyl ester 2-tert-butyl ester, 28, (1.42 mg, 4.40 mmol) is dissolved in pyridine (22 mL). 4-Dimethylamino-pyridine (10 mg) is added followed by trimethylacetyl chloride (1.63 mL, 13.2 mmol). The reaction is stirred at ambient temperature for 12 hours. The cloudy reaction mixture is then concentrated in vacuo to afford a white residue. Dichloro-methane (75 mL) is added to the residue and the mixture washed with a 1.0 N aqueous solution of hydrochloric acid (75 mL). The aqueous layer is extracted with dichloro-methane (75 mL), the combined organic layers washed with a saturated aqueous solution of NaHCO₃ (75 mL), water (75 mL), brine (75 mL), then dried, filtered and concentrated in vacuo to afford the crude product. The crude product is purified over silica(4:1 to 1:1 hexane/ethyl acetate) to afford 1.76 g (98% yield) of the desired product as a clear, viscous oil.

Preparation of 4-(2,2-dimethylpropionyloxy) pyrazolidine-1-carboxylic acid 1-benzyl ester (30): 4-(2,2-Dimethylpropionyloxy)pyrazolidine-1,2-dicarboxylic acid 1-benzyl ester 2-tert-butyl ester, 29, (1.76 g, 4.33 mmol) is dissolved in methanol (40 mL) and the solution cooled to 0° C. Thionyl chloride (3.16 mL, 43.3 mmol) is added dropwise and the reaction allowed to warm to room temperature and continue stirring 12 hours. The reaction solution is concentrated in vacuo to give afford 1.45 g (98% yield) of the desired product as the HCl salt as an off-white solid.

Preparation of 2-[2-(4-fluorophenyl)acetyl]-4-(2,2-dimethylpropionyloxy) pyrazolidine-1-carboxylic acid 1-benzyl ester (31): 4-(2,2-Dimethylpropionyloxy)-pyrazolidine-1-carboxylic acid 1-benzyl ester, 30, (1.45 g, 4.23 mmol) is dissolved in dichloromethane (21 mL). The solution is cooled to 0° C. and triethylamine (1.30 mL, 9.31 mmol) added dropwise via syringe. The cold bath is removed and the reaction allowed to warm to room temperature and continue stirring 20 minutes. 4-Fluorophenylacetic acid (848 mg, 5.50 mmol) is added. After stirring for 5 minutes, the reaction mixture is transferred via cannula into a solution of 1-ethyl-3-(3-dimethylaminopropyl)-carbodiimide hydrogen chloride in dichloromethane (21 mL) maintained at 0° C. The reaction is allowed to stir and gradually warm to room temperature over 12 hours. The reaction is washed with a 5% aqueous solution of Na₂CO₃ (2×50 mL). The combined aqueous layers are extracted several times with dichloromethane (50 mL) and the combined organic layers washed with brine, dried, filtered and concentrated in vacuo. The crude product is purified over silica (2:1 to 1:1 hexane/ethyl acetate) to afford 1.71 g (91% yield) of the desired product as a white solid.

Preparation of 2,2-dimethyl-propionic acid 1-[2-(4fluorophenyl)acetyl]-pyrazolidin-4-yl ester (32): 2-[2-(4-Fluorophenyl)acetyl]-4-(2,2-dimethylpropionyloxy)-pyrazolidine-1-carboxylic acid 1-benzyl ester, 31, (1.71 g, 3.86 mmol) is dissolved in methanol (40 mL). The flask is flushed with nitrogen and charged with 10% palladium on carbon (300 mg). The reaction flask is stirred vigorously at room temperature under 1 atmosphere of hydrogen gas for 6 hours. The flask is flushed with nitrogen and the reaction mixture filtered through a pad of Celite, rinsing with ethyl acetate (100 mL). The filtrate is concentrated in vacuo to afford 1.18 g (98% yield) of the desired product as a tan solid.

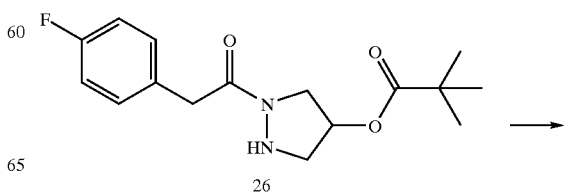

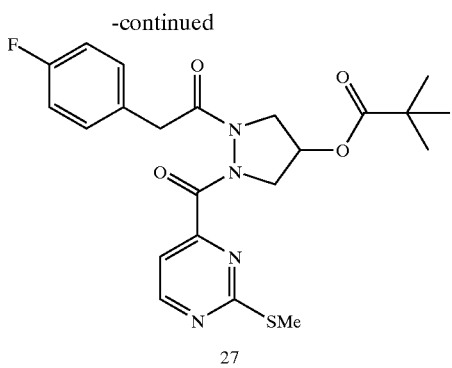

27

Preparation of 2,2-dimethyl-propionic acid 1-[2-(4-fluorophenyl)acetyl]-2-(methylsulfanyl-pyrimidine-4-carbonyl)-pyrazolidin-4-yl ester (33): To a solution of 2,2-dimethyl-propionic acid 1-[2-(4-fluorophenyl)acetyl]-pyrazolidin-4-yl ester, 32, (427 mg, 1.79 mmol) in dichloromethane (3 mL) is added 2-methylsulfonyl-pyrimidine-4-carbonyl chloride (676 mg, 3.58 mmol) followed by dropwise addition of a 1.0 N aqueous solution of sodium hydroxide (6 mL). The mixture is vigorously stirred at room temperature for 12 hours. The reaction is diluted with dichloromethane (25 mL) and washed with water (25 mL). The aqueous layer is back-extracted with dichloromethane (25 mL). The combined organic layers are washed with a saturated aqueous solution of sodium bicarbonate (25 mL) and brine (25 mL), dried, filtered and concentrated in vacuo. The resulting crude material is purified over silica (1:1 hexane/ethyl acetate to 100% ethyl acetate) to afford 464 mg (96.6% yield) of the desired product as a brown, viscous oil.

Preparation of 2,2-dimethyl-propionic acid 6(4-fluorophenyl)-7-(2-methylsulfanyl-pyrimidin-4-yl)-5-oxo-2,3-dihydro-1H,5H-pyrazolo[1,2-a]pyrazol-2-yl ester (34): 2,2-Dimethyl-propionic acid 1-[2-(4-fluorophenyl)acetyl]-2-(methylsulfanyl-pyrimidine-4-carbonyl)-pyrazolidin-4-yl ester, 33, (300 mg, 0.651 mmol) is dissolved in THF (6 mL. This solution is then added dropwise via cannula to a suspension of NaH (29 mg of a 60% dispersion in mineral oil, 0.716 mmol) at −30° C. The reaction is allowed to gradually warm to 0° C. over 3 hours. The reaction is quenched with NH$_4$Cl (sat. aq.) (1 mL). The mixture is stirred at room temperature, then concentrated in vacuo. The residue is diluted with tetrahydrofuran (50 mL) and the mixture filtered through Celite. The filtrate is concentrated in vacuo to give an orange oil. The crude product is purified over silica (100% ethyl acetate to 5% to 10% to 20% methyl alcohol/ethyl acetate) to afford 87 mg (30% yield) of the desired product as a yellow solid.

Preparation of 2,2-dimethyl-propionic acid 6-(4-fluorophenyl)-7-(2-methane-sulfonyl-pyrimidin-4-yl)-5oxo-2,3-dihydro-1H,5H-pyrazolo1,2-a]pyrazol-2-yl ester (35): 2,2-Dimethyl-propionic acid 6-(4-fluorophenyl)-7-(2-methylsulfanyl-pyrimidin-4-yl)-5-oxo-2,3-dihydro1H,5H-pyrazolo[1,2-a]pyrazol-2-yl ester, 34, (96 mg, 0.217 mmol) is dissolved in chloroform (2 mL). The solution was cooled to 0° C. and a solution of 3-chloroperbenzoic acid (117 mg of ~77% purity, 0.521 mmol) in chloroform (3 mL) is added dropwise to the yellow suspension. The reaction is stirred at 0° C. for 3 hours, then at room temperature for 12 hours. The yellow-colored reaction solution is washed with NaHSO$_3$ (sat. aq.) (2×15 mL). The layers are separated and the aqueous layer extracted with chloroform (2×15 mL). The combined organic layers are washed with NaHCO$_3$ (sat. aq.) (20 mL), dried, filtered and concentrated in vacuo to afford 50 mg (48% yield) of the desired product as a yellow oil.

Preparation of 2-(4-fluorophenyl)-6hydroxy-3-(2-phenoxypyrimidin-4-yl)-6,7-dihydro-5H-pyrazolo[1,2-a]pyrazol-1-one (36): A solution of 2,2-dimethyl-propionic acid 6-(4-fluorophenyl)-7-(2-methane-sulfonyl-pyrimidin-4-yl)-5-oxo-2,3-dihydro-1H,5H-pyrazolo[1,2-a]pyrazol-2-yl ester, 35, (50 mg, 0.105 mmol) in THF (1 mL) is slowly cannulated into a solution of sodium phenolate in THF (1 mL) at 0° C. The cooling bath is removed and the reaction stirred at room temperature for 1 hour. The reaction is quenched with NH$_4$Cl (sat. aq.) (500 μL). The reaction mixture is concentrated in vacuo and the residue diluted taken up in ethyl acetate (15 mL). The solution is washed with water (20 mL) and a 5% aqueous Na$_2$CO$_3$ (20 mL). The combined aqueous layers are extracted with ethyl acetate (25 mL) and brine (20 mL), dried, filtered and concentrated in vacuo. The crude material is purified over silica (100% ethyl acetate to 5% to 10% to 20% methyl alcohol/ethyl acetate) to afford 9 mg (21% yield) of the desired product as a yellow solid. $^1$H NMR (300 MHz, CDCl$_3$) □ 8.43 (d, J=5.2 Hz, 1H), 7.46 (t, J=7.8 Hz, 2H), 7.31–7.27 (m, 3H), 7.19 (d, J=8.2 Hz, 2H), 7.03 (t, J=8.6 Hz 2H), 6.80 (d, J=5.2 Hz, 1H), 5.41 (br s, 1H), 4.82 (m, 1H), 4.23 (d, J=12.4 Hz, 1H), 3.95–3.85 (m, 2H), 3.76 (dd, J=12.4, 4.4 Hz, 1H); HRMS m/z calcd for C$_{22}$H$_{18}$FN$_4$O$_3$ (MH$^+$) 405.1363, found 405.1365.

This procedure can be used to prepare Category III analogs of the first aspect wherein R$^8$ is C$_1$–C$_4$ alkyl. Conversion of intermediate 28 to an Intermediate of Type IV, for example, the methoxy analog 37, by the following procedure allows the formulator to assemble 6-alkoxy ring analogs of Category III.

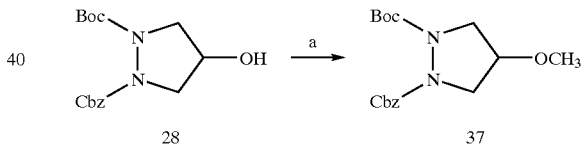

Reagents and conditions: CH$_3$I, Ag$_2$O; DMF; dark, rt 12 hr.

Preparation of 4-methoxypyrazolidine-1,2-dicarboxylic acid 1-benzyl ester 2-tert-butyl ester (37): 4-Methoxypyrazolidine-1,2-dicarboxylic acid 1-benzyl ester 2-tert-butyl ester, 28, (2.55 g, 7.91 mmol) is dissolved in dimethylformamide (40 mL). Methyl iodide (1.97 mL, 31.6 mmol) is added followed by silver oxide (3.67 g, 15.8 mmol). The flask is cover with foil and stirred for 12 hours in the absence of light. The reaction mixture is poured into ether (150 mL). The mixture is stirred vigorously at room temperature and filtered through a pad of Celite. The filtrate is washed with water (2×150 mL) and brine (150 mL), dried, filtered and concentrated in vacuo to afford 2.58 g (97% yield) of the desired product as a yellow, clear oil.

The second aspect of Category III analogs relates to scaffolds having the R$^2$ substituent at the 6-position of the pyrazolo[1,2-a]pyrazol-1-one ring system comprise a carbonyl unit selected from the group consisting of —(CH$_2$)$_j$CO$_2$R$^{10}$; —(CH$_2$)$_j$OCO$_2$R$^{10}$; —(CH$_2$)$_j$CON(R$^{10}$)$_2$, and —(CH$_2$)$_j$OCON(R$^{10}$)$_2$, wherein R$^{10}$ is the same as defined herein above. A non-limiting example of an analog according to the second aspect of Category III has the formula:

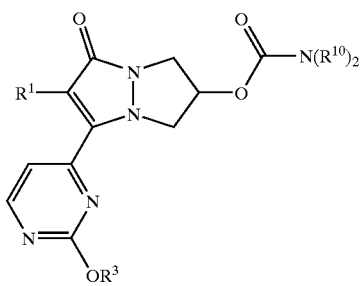

Table VII illustrates examples of this aspect of the present invention wherein two $R^{10}$ units are taken together to form a ring.

TABLE VII

| No. | $R^1$ | $R^3$ | $R^{10}$ ring |
|---|---|---|---|
| 281 | 4-fluorophenyl | phenyl | morpholin-1-yl |
| 282 | 4-fluorophenyl | 4-fluorophenyl | morpholin-1-yl |
| 283 | 4-fluorophenyl | 2-aminophenyl | morpholin-1-yl |
| 284 | 4-fluorophenyl | 2-methylphenyl | morpholin-1-yl |
| 285 | 4-fluorophenyl | 4-methylphenyl | morpholin-1-yl |
| 286 | 4-fluorophenyl | 4-methoxyphenyl | morpholin-1-yl |
| 287 | 4-fluorophenyl | 4-(propanesulfonyl)phenyl | morpholin-1-yl |
| 288 | 4-fluorophenyl | 3-benzo[1,3]dioxol-5-yl | morpholin-1-yl |
| 289 | 4-fluorophenyl | pyridin-2-yl | morpholin-1-yl |
| 290 | 4-fluorophenyl | pyridin-3-yl | morpholin-1-yl |
| 291 | 4-fluorophenyl | phenyl | piperidin-1-yl |
| 292 | 4-fluorophenyl | 4-fluorophenyl | piperidin-1-yl |
| 293 | 4-fluorophenyl | 2-aminophenyl | piperidin-1-yl |
| 294 | 4-fluorophenyl | 2-methylphenyl | piperidin-1-yl |
| 295 | 4-fluorophenyl | 4-methylphenyl | piperidin-1-yl |
| 296 | 4-fluorophenyl | 4-methoxyphenyl | piperidin-1-yl |
| 297 | 4-fluorophenyl | 4-(propanesulfonyl)phenyl | piperidin-1-yl |
| 298 | 4-fluorophenyl | 3-benzo[1,3]dioxol-5-yl | piperidin-1-yl |
| 299 | 4-fluorophenyl | pyridin-2-yl | piperidin-1-yl |
| 300 | 4-fluorophenyl | pyridin-3-yl | piperidin-1-yl |
| 301 | 4-fluorophenyl | phenyl | piperazin-1-yl |
| 302 | 4-fluorophenyl | 4-fluorophenyl | piperazin-1-yl |
| 303 | 4-fluorophenyl | 2-aminophenyl | piperazin-1-yl |
| 304 | 4-fluorophenyl | 2-methylphenyl | piperazin-1-yl |
| 305 | 4-fluorophenyl | 4-methylphenyl | piperazin-1-yl |
| 306 | 4-fluorophenyl | 4-methoxyphenyl | piperazin-1-yl |
| 307 | 4-fluorophenyl | 4-(propanesulfonyl)phenyl | piperazin-1-yl |
| 308 | 4-fluorophenyl | 3-benzo[1,3]dioxol-5-yl | piperazin-1-yl |
| 309 | 4-fluorophenyl | pyridin-2-yl | piperazin-1-yl |
| 310 | 4-fluorophenyl | pyridin-3-yl | piperazin-1-yl |

As described herein above, the procedure for preparing compounds included within the first aspect of category m encompasses a final step wherein the O-protecting unit, inter alia, —C(O)C(CH$_3$)$_3$ is removed during the same step which adds the —OR$^3$ unit to the scaffold, for example, the conversion of 35 to 36. For the analogs of the second aspect the following procedure, as outlined below, is use to prepare the analogs wherein one of the 6-position R$^2$ unit is a carbonyl unit as described herein under the second aspect of Category III.

The following scheme begins with intermediate 11 prepared as described herein above.

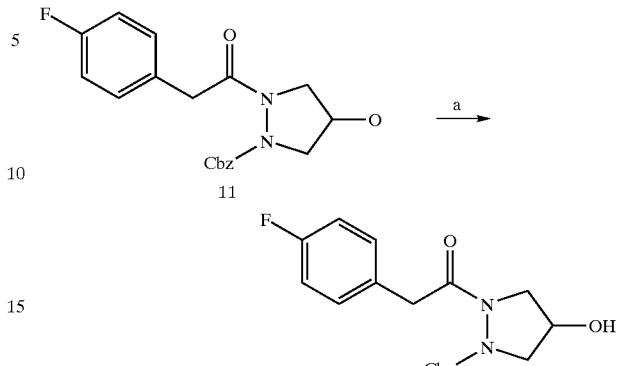

Reagents and conditions: (a) BH$_3$; DMS, THF; −78° C. 1 hr.

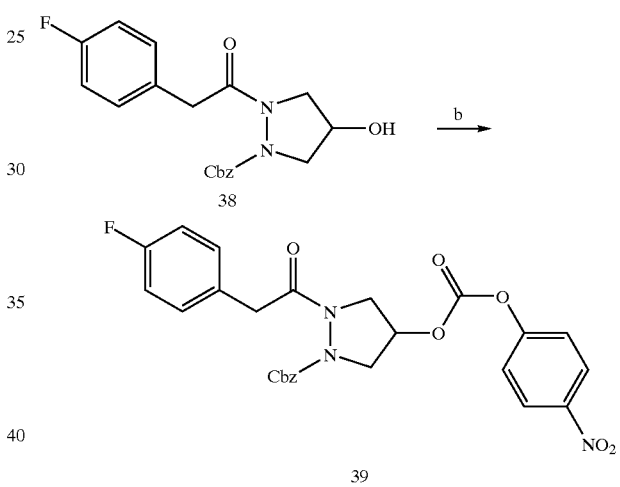

Reagents and conditions: (b) p-nitrorphenyl chloroformate, CH$_2$Cl$_2$, pyridine, 0° C. 1 hr, rt 12 hr.

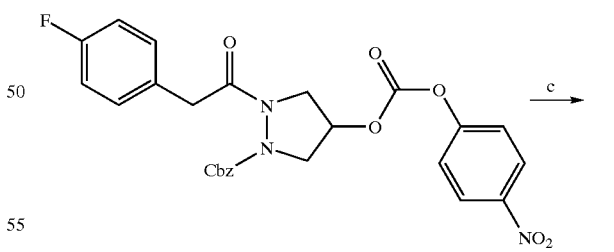

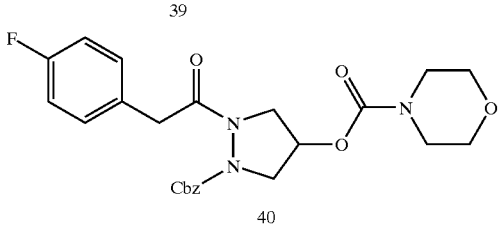

Reagents and conditions: (c) morpholine, CH$_2$Cl$_2$, rt 1.5 hr.

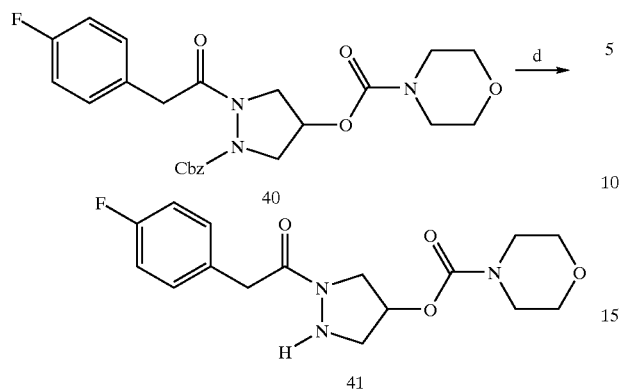

Reagents and conditions: (d) H$_2$, Pd/C; MeOH:, rt 2.5 hr.

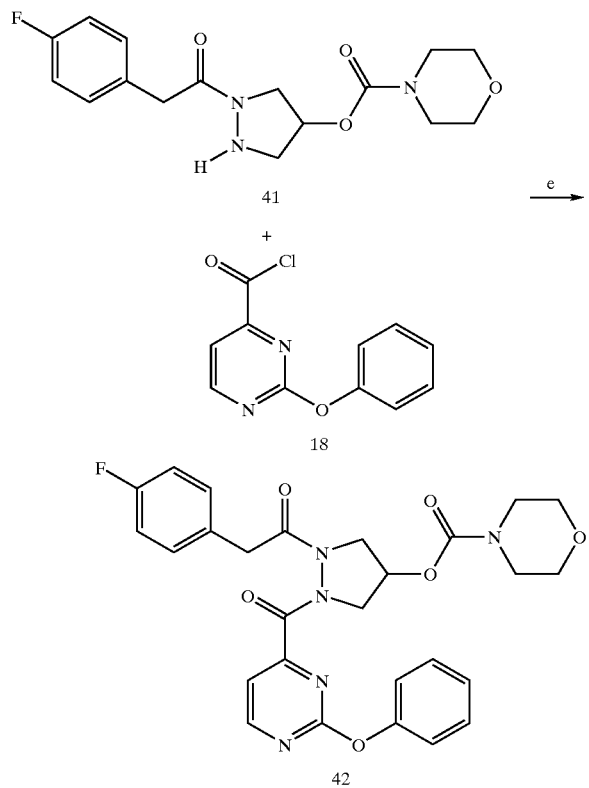

Reagents and conditions: (e) 1N NaOH, CH$_2$Cl$_2$.

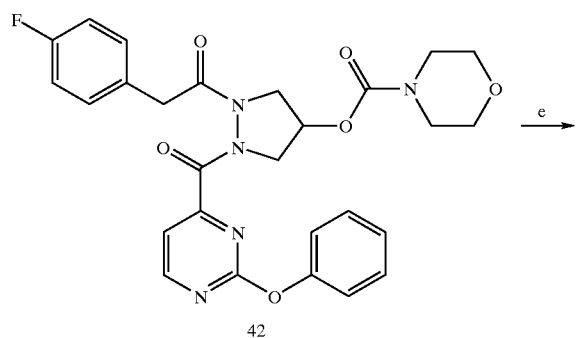

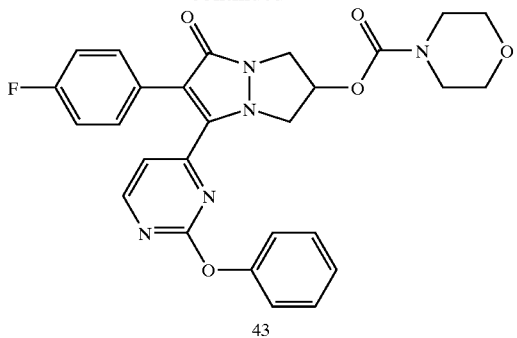

Reagents and conditions: (b) NaH. THF, DMF: −10° C. 1 hr, 0° C. 2 hr.

EXAMPLE 12

Morpholine-4-carboxylic acid 6-(4-fluorophenyl)-5-oxo-7-(2-phenoxypyrimidin-4-yl)-2,3-dihydro-1H, 5H-pyrazolo[1,2-a]pyrazol-2-yl ester (43)

Preparation of 2-[2-(4-fluorophenyl)acetyl]4-hydroxy-pyrazolidine-1-carboxylic acid benzyl ester (38): 2-[2-(4-Fluorophenyl)acetyl]-4-oxo-pyrazolidine-1-carboxylic acid benzyl ester, 11, (1.0 g, 2.81 mmol) is dissolved in THF (30 mL) and the solution cooled to −78° C. A S 5.0M solution of borane-dimethyl sulfide complex in ether (1.2 mL, 5.61 mmol) is added dropwise. After 1 hour at −78° C., the reaction is quenched by slow addition of NH$_4$Cl (sat. aq.) (10 mL). The cooling bath is then removed, and the mixture allowed to warm to room temperature with vigorous stirring. The THF is removed in vacuo and the residue diluted with water (50 mL) The mixture is extracted with ethyl acetate (2×100 mL), dried, filtered and concentrated in vacuo to give a yellow oil which is purified over silica (1:1 to 1:2 hexane/ethyl acetate to 100% ethyl acetate) to afford 731 mg (73% yield) as a clear, viscous oil.

Preparation of 2-[2-(4-fluorophenyl)acetyl]-4-(4-nitro-phenoxycarbonyloxy)-pyrazolidine-1-carboxylic acid benzyl ester (39): 2-[2-(4-Fluorophenyl)acetyl]-4-hydroxy-pyrazolidine-1-carboxylic acid benzyl ester, 38, (366 mg, 1.02 mmol) is dissolved in dichloromethane (10 mL). The solution is cooled to 0° C. and p-nitrophenyl chloroformate (411 mg, 2.04 mmol) is added in one portion. The solution is stirred at 0° C., and pyridine (198 μL, 2.45 mmol) added. Stirring is continued at 0° C. for 1 hour followed by stirring at room temperature for 12 hours. The reaction is diluted with water (40 mL) and extracted with dichloromethane (40 mL). The organic layer is washed with 0.5 N NaOH (2×40 mL). The combined aqueous layers are back-extracted with dichloromethane (30 mL). The combined organic layers are washed with brine (30 mL), dried, filtered, and concentrated in vacuo. The crude material is purified over silica (3:1 to 2:1 to 1:1 hexane/ethyl acetate) to afford 462 mg (86% yield) of the desired product as a white foam.

Preparation of morpholine-4-carboxylic acid 1-benzyloxycarbonyl-2-[2-(4-fluorophenyl)acetyl]-pyrazolidin-4-yl ester (40): 2-[2-(4-Fluorophenyl)acetyl]-4-(4-nitro-phenoxycarbonyloxy)-pyrazolidine-1-carboxylic acid benzyl ester, 39, (462 mg, 0.882 mmol) is dissolved in dichloromethane (9 mL). Morpholine (770 μL, 8.82 mmol) is added and the reaction immediately develops a light yellow color. After stirring about 1.5 hours at room temperature, the reaction is diluted with dichloromethane (20 mL) and washed with a 5% solution of $Na_2CO_3$ (2×20 mL). The combined aqueous layers are extracted with dichloromethane (20 mL), the organic layers combined, washed with water, brine, and dried. The solvent is removed in vacuo to afford 414 mg of the desired product as a clear oil.

Preparation of morpholine-4-carboxylic acid 1-[2-(4-fluorophenyl)acetyl]-pyrazolidin-4-yl ester (41): morpholine4-carboxylic acid 1-benzyloxycarbonyl-2-[2-(4-fluorophenyl)acetyl]-pyrazolidin-4-yl ester, 40, (512 mg, 1.09 mmol) is dissolved in methanol (10 mL) and the flask flushed with nitrogen then charged with 10% palladium on carbon (103 mg). The reaction mixture is vigorously stirred and hydrogenated at 1 atmosphere for 2.5 hours at room temperature. The reaction mixture is filtered through a pad of Celite, rinsed with ethyl acetate (100 ml.) and concentrated in vacuo to afford 354 mg of the desired product as a white powder.

Preparation of morpholine-4-carboxylic acid 1-[2-(4-fluorophenyl)acetyl]-2-(2-phenoxypyrimidine-4-carbonyl)-pyrazolidin-4-yl ester (42): Morpholine-4-carboxylic acid 1-[2-(4-fluorophenyl)acetyl]-pyrazolidin-4-yl ester, 41, (354 mg, 1.05 mmol) and 2-phenoxypyrimidine-4-carbonyl chloride, 18, (345 mg, 1.47 mmol) are dissolved in dichloromethane (2 mL). 1.0 N NaOH (3 mL) is added dropwise at room temperature while vigorously stirring. The reaction is allowed to proceed for 12 hours after which time additional acid chloride, 18, is added and stirring continued for 3 hours. Additional acid chloride, 18, (83 mg) is added and stirring continued for an additional 12 hours. After which time the reaction is diluted with dichloromethane (50 mL) and washed with water (50 mL). The combined organic layers are washed with $NaHCO_3$ (sat.) (50 mL) and brine (50 mL), dried, filtered and concentrated to provide a brown oil. The crude material is purified over silica (100% ethyl acetate to 5% methyl alcohol/ethyl acetate) afford 348 mg (61% yield) of the desired product as a viscous oil.

Preparation of morpholine-4-carboxylic acid 6-(4-fluorophenyl)-5-oxo-7-(2-phenoxypyrimidin-4-yl)-2,3-dihydro-1H,5H-pyrazolo[1,2-a]pyrazol-2-yl ester (43); A solution of morpholine-4-carboxylic acid 1-[2-(4-fluorophenyl)acetyl]-2-(2-phenoxypyrimidine-4-carbonyl)-pyrazolidin-4-yl ester, 42, (154 mg, 0.287 mmol) in dimethylformamide (3 mL) is added dropwise to a -10° C. suspension of sodium hydride (16.4 mg of a 60% dispersion in mineral oil, 0.410 mmol) in tetrahydrofuran (3 mL). After 1 hour at -10° C., the reaction was warmed to 0° C. for 2 hours. The orange-colored solution is then quenched by slowly adding saturated $NH_4Cl$ (400 μL). The cooling bath is removed, and the solution allowed to warm to room temperature. The reaction mixture is concentrated in vacuo and the resulting residue is dissolved in THF (25 mL) and filtered through a pad of Celite. The filtrate is concentrated in vacuo and the residue purified by Prep HPLC to afford 47 mg (32% yield) of the desired product as a yellow solid. $^1$H NMR (300 MHz, $CDCl_3$) δ 8.46 (d, J=4.9 Hz, 1H), 7.47–7.18 (m, 9H), 7.08 (t, J=8.7 Hz, 2H), 6.89 (d, J=4.9 Hz, 1H), 5.66 (m, 1H), 4.16 (m, 2H), 4.02 (d, J=12.9 Hz, 1H), 3.87 (dd, J=12.9, 5.1 Hz, 1H), 3.79–3.30 (m, 8H1); HRMS m/z calcd for $C_{27}H_{25}FN_5O_5$ (MH$^+$) 518.1840, found 518.1815.

The third aspect of Category III analogs relates to amino analogs having the formula:

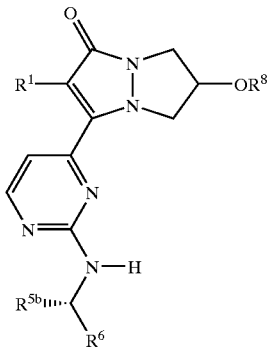

wherein R units are amines having the formula —NH[CHR$^{5b}$]R$^6$, and R$^1$, R$^{5b}$, R$^6$ and R$^8$ are herein below in Table VIII.

TABLE VIII

| No. | R$^1$ | R$^{5b}$ | R$^6$ | R$^8$ |
|---|---|---|---|---|
| 311 | 4-fluorophenyl | H | phenyl | methyl |
| 312 | 4-fluorophenyl | H | 4-fluorophenyl | methyl |
| 313 | 4-fluorophenyl | H | 2-aminophenyl | methyl |
| 314 | 4-fluorophenyl | H | 2-methylphenyl | methyl |
| 315 | 4-fluorophenyl | H | 4-methylphenyl | methyl |
| 316 | 4-fluorophenyl | H | 4-methoxyphenyl | methyl |
| 317 | 4-fluorophenyl | H | 4-(propanesulfonyl)phenyl | methyl |
| 318 | 4-fluorophenyl | H | 3-benzo[1,3]dioxol-5-yl | methyl |
| 319 | 4-fluorophenyl | H | pyridin-2-yl | methyl |
| 320 | 4-fluorophenyl | H | pyridin-3-yl | methyl |
| 321 | 4-fluorophenyl | H | H | methyl |
| 322 | 4-fluorophenyl | H | methyl | methyl |
| 323 | 4-fluorophenyl | H | ethyl | methyl |
| 324 | 4-fluorophenyl | H | vinyl | methyl |
| 325 | 4-fluorophenyl | H | cyclopropyl | methyl |
| 326 | 4-fluorophenyl | H | cyclohexyl | methyl |
| 327 | 4-fluorophenyl | H | methoxymethyl | methyl |
| 328 | 4-fluorophenyl | H | methoxyethyl | methyl |
| 329 | 4-fluorophenyl | H | 1-hydroxy-1-methylethyl | methyl |
| 330 | 4-fluorophenyl | H | —CO$_2$H | methyl |
| 331 | 4-fluorophenyl | methyl | phenyl | methyl |
| 332 | 4-fluorophenyl | methyl | 4-fluorophenyl | methyl |
| 333 | 4-fluorophenyl | methyl | 2-aminophenyl | methyl |
| 334 | 4-fluorophenyl | methyl | 2-methylphenyl | methyl |
| 335 | 4-fluorophenyl | methyl | 4-methylphenyl | methyl |
| 336 | 4-fluorophenyl | methyl | 4-methoxyphenyl | methyl |
| 337 | 4-fluorophenyl | methyl | 4-(propanesulfonyl)phenyl | methyl |
| 338 | 4-fluorophenyl | methyl | 3-benzo[1,3]dioxol-5-yl | methyl |
| 339 | 4-fluorophenyl | methyl | pyridin-2-yl | methyl |
| 340 | 4-fluorophenyl | methyl | pyridin-3-yl | methyl |
| 341 | 4-fluorophenyl | methyl | H | methyl |
| 342 | 4-fluorophenyl | methyl | methyl | methyl |
| 343 | 4-fluorophenyl | methyl | ethyl | methyl |
| 344 | 4-fluorophenyl | methyl | vinyl | methyl |
| 345 | 4-fluorophenyl | methyl | cyclopropyl | methyl |
| 346 | 4-fluorophenyl | methyl | cyclohexyl | methyl |
| 347 | 4-fluorophenyl | methyl | methoxymethyl | methyl |
| 348 | 4-fluorophenyl | methyl | methoxyethyl | methyl |
| 349 | 4-fluorophenyl | methyl | 1-hydroxy-1-methylethyl | methyl |
| 350 | 4-fluorophenyl | methyl | —CO$_2$H | methyl |

The analogs which comprise the third aspect of Category III of the present invention can be prepared using the procedure outlined herein below beginning with intermediate 28.

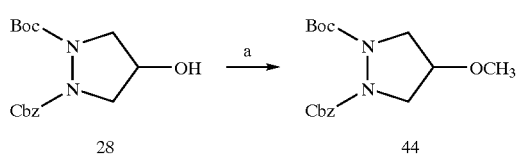
Reagents and conditions: (a) CH$_3$I, Ag$_2$O, DMF, dark, rt, 12 hr.
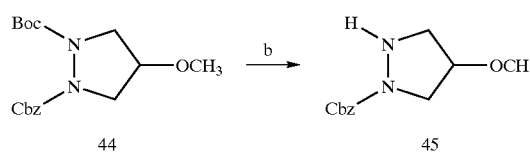
Reagents and conditions: (b) SOCl$_2$, MeOH; 0° C. to rt, 12 hr.
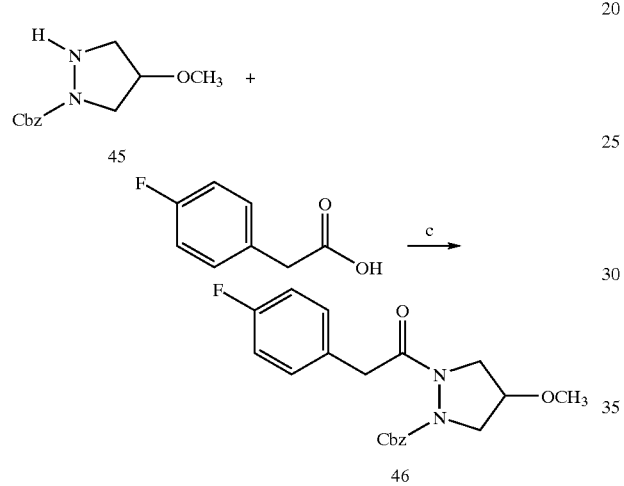
Reagents and conditions: (c) RCOCl, NaOH, rt, 6 hr.
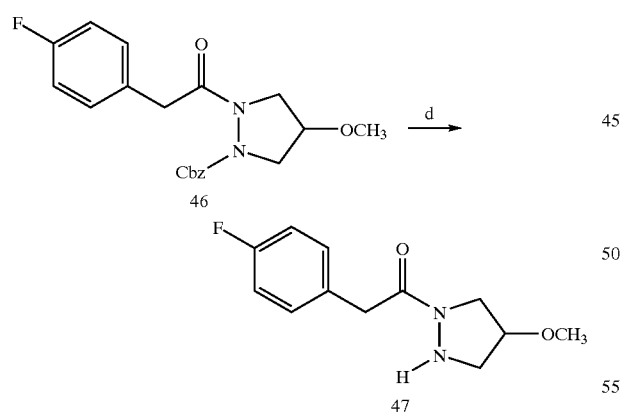
Reagents and conditions: (6) H$_2$: Pd/C, MeOH; rt, 3 hr.
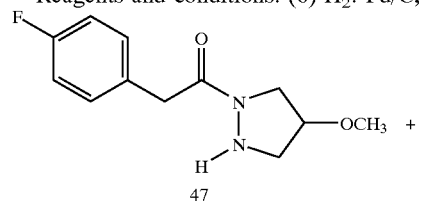
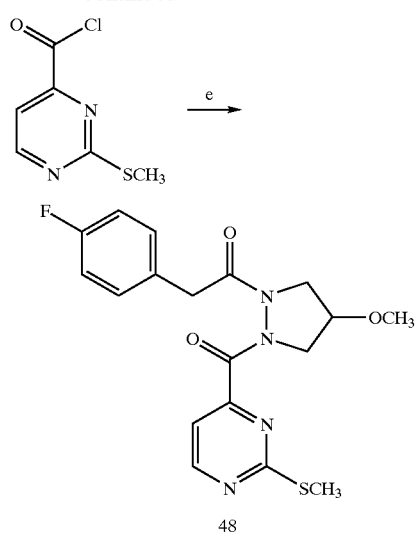
Reagents and Conditions: (e) NaOH: CH$_2$Cl$_2$/water, rt 4 hr.
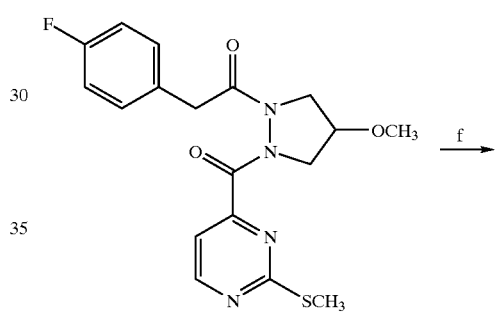
Reagents and Conditions: (h) NaH, DMF; 0° C. to t, 2 hr.
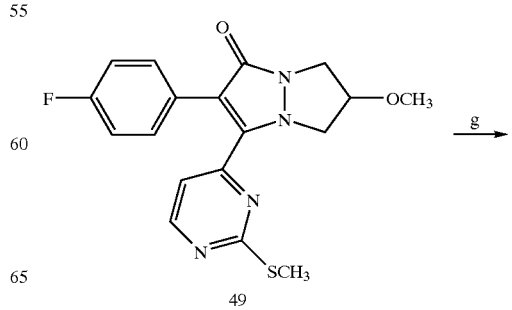

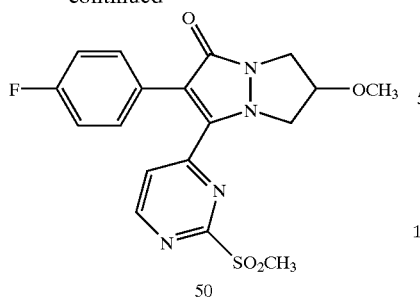

Reagents and Conditions: (g) m-chloroperbenzoic acid; CH₂Cl₂; rt 30 min.

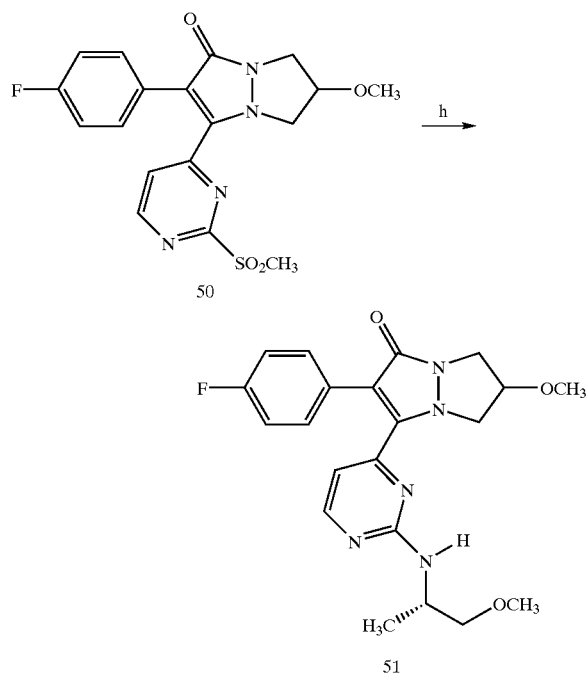

Reagents and Conditions: (h) toluene: 120° C. 2 hr.

EXAMPLE 13

2-(4-fluorophenyl)-6-methoxy-3-[2-(2-(S)-methoxy-1-methylethylamino)-pyrimidin-4-yl]-6,7-dihydro-5H-pyrazolo[1,2a]pyrazol-1-one (51)

Preparation of 2-[2-(4-fluorophenyl)acetyl]-4-methoxy-pyrazolidine-1-carboxylic acid benzyl ester (44): 2-[2-(4-Fluorophenyl)acetyl]-4-hydroxy-pyrazolidine-1-carboxylic acid benzyl ester, 28, (2.55 g, 7.91 mmol) is dissolved in dimethylformamide (40 mL). Methyl iodide (1.97 mL, 31.6 mmol) is added followed by silver oxide (3.67 g, 15.8 mmol). The flask is cover with foil and stirred overnight in the absence of light. The reaction mixture is poured into ether (150 mL). The mixture is stirred vigorously at room temperature and filtered through a pad of Celite. The filtrate is washed with water (2×150 mL) and brine (150 mL), dried over sodium sulfate, filtered and concentrated in vacuo to afford 2.58 g (97% yield) of the desired product as a yellow, clear oil.

Preparation of 2-[2-(4-fluorophenyl)acetyl]-4-(4-methoxy)-pyrazolidine-1-carboxylic acid benzyl ester (45): 2-[2-(4-fluorophenyl)acetyl]4-methoxy-pyrazolidine-1-carboxylic acid benzyl ester, 44, (2.57 g, 7.64 mmol) is dissolved in methyl alcohol (75 mL) and the solution cooled to 0° C. Thionyl chloride (5.58 mL, 76.4 mmol) is added dropwise and the reaction is allowed to warm to room temperature overnight. The reaction solution is concentrated in vacuo to afford 2.07 g (99% yield) of the desired product as the HCl salt as an off-white solid.

Preparation or 2-[2-(4-fluorophenyl)acetyl]-4-methoxy-pyrazolidine-1-carboxylic acid benzyl ester (46): 2-[2-(4-Fluorophenyl)acetyl]4-(4-methoxy)-pyrazolidine-1-carboxylic acid benzyl ester, 45, (8.81 g, 32.3 mmol) is dissolved in dichloromethane (150 mL). 4-fluorophenylacetyl chloride (5.31 g, 38.8 mmol) is added followed by a 0.5 N aqueous solution of sodium hydroxide (150 mL). The mixture is stirred vigorously at room temperature for 6 hours. The reaction is diluted with dichloromethane (200 mL) and washed with water (200 mL). The aqueous layer is extracted with dichloromethane (2×200 mL). The combined organic layers are washed with 5% aqueous sodium carbonate solution (250 ml) and brine (250 mL), dried over sodium sulfate, filtered and concentrated in vacuo to afford 12.0 g of the desired product as a viscous, tan oil.

Preparation of 2-(4-fluorophenyl)-1-(4-methoxy-pyrazolidin-1-yl)-ethanone (47): 2-[2-(4-Fluorophenyl)acetyl]-4-methoxy-pyrazolidine-1-carboxylic acid benzyl ester, 46, (12.0 g, 32.2 mmol) is dissolved in methyl alcohol (300 mL). The flask is flushed with nitrogen and charged with 10% palladium on carbon (1.2 g). The reaction mixture is stirred vigorously at room temperature under 1 atmosphere of hydrogen gas for 3 hours. The flask is flushed with nitrogen and the reaction mixture filtered through a pad of Celite, rinsing with ethyl acetate (100 mL). The filtrate is concentrated in vacuo to afford 7.67 g of the desired product as a viscous, clear oil.

Preparation of 2-(4-fluorophenyl)-1-[4methoxy-2-(2-methylsulfanyl-pyrimidine-4-carbonyl)pyrazolidine-1-yl]-ethanone (48): 2-(4-Fluorophenyl)-1-(4-methoxy-pyrazolidin-1-yl)ethanone, 47, (7.67 g, 32.2 mmol) and 2-methylsulfonyl-pyrimidine-4-carbonyl chloride (9.11 g, 48.3 mmol) are dissolved in dichloromethane (150 mL). A 0.5 N aqueous solution of sodium hydroxide (150 mL) is added steadily via addition funnel and the mixture is stirred vigorously at room temperature for 4 hours. The reaction is diluted with 5% aqueous sodium carbonate solution (1 L). The mixture is extracted with dichloromethane (6×200 mL). The combined organic layers are dried over magnesium sulfate, filtered and concentrated to give a red oil. The crude material is purified by over silica (1:1 to 1:3 hexane/ethyl acetate to 100% ethyl acetate) to afford 10.3 g of the desired product as a brown, viscous oil.

Preparation of 2-(4-fluorophenyl)-6-methoxy-3-(2-methylsulfanyl-pyrimidin-4yl)-6,7-dihydro-5H-pyrazolo[1,2-a]pyrazol-1-one (49): A solution of 2-(4-fluorophenyl)-1-[4-methoxy-2-(2-methylsulfanyl-pyrimidine-4-carbonyl)pyrazolidine-1-yl]-ethanone, 48, (2.04 g, 5.22 mmol) in 1:1 dimethylformamide/tetrahydrofuran (30 mL) is added dropwise to a 0° C. suspension of sodium hydride (230 mg of a 60% dispersion in mineral oil, 5.75 mmol) in dimethylformamide (60 mL). After 2 hours at 0° C., the bright red solution is quenched by slow addition of a saturated aqueous solution of ammonium chloride (5 mL). The cold bath is removed, and the solution allowed to warm to room temperature. The reaction mixture is concentrated in vacuo and the resultant residue diluted with ethyl acetate (175 mL.). The mixture is washed with a saturated aqueous solution of ammonium chloride (150 mL). The aqueous layer is extracted with ethyl acetate (4×75 mL). The combined organic layers are dried over magnesium sulfate, filtered and concentrated in vacuo. The crude material is purified over silica gel (100% ethyl acetate to 5% to 10% to 20% methyl alcohol/ethyl acetate) to afford 1.1 g (57% yield) of the desired product as an orange oil.

Preparation of 2-(4-fluorophenyl)-6-methoxy-3-(2-methanesulfonyl-pyrimidin-4-yl)-6,7-dihydro-5H-pyrazolo[1,2a]pyrazol-1-one (50): 2-(4-Fluorophenyl)-6-methoxy-3-(2-methylsulfanyl-pyrimidin-4-yl)-6,7-dihydro-5H-pyrazolo[1,2-a]pyrazol-1-one, 49, (1.10 g, 2.95 mmol) is diluted with dichloromethane (60 mL). 3-Chloroperbenzoic acid (662 mg of ~77% purity, 2.95 mmol) is added all at once to the yellow suspension. After 20 min, additional 3-chloroperbenzoic acid (240 mg, 1.07 mmol) is added. After 10 minutes, the clear, yellow reaction solution is poured in a 10% aqueous solution of sodium bisulfite (60 mL). The layers are separated and the aqueous layer extracted with dichloromethane (2×50 mL). The combined organic layers are washed with a'saturated aqueous solution of sodium bicarbonate (2×50 mL), dried over sodium sulfate, filtered and concentrated in vacuo to afford 948 mg of a mixture of the corresponding sulfoxide and sulfone as a yellow solid. Used as is for next step.

Preparation of 2-(4-fluorophenyl)-6-methoxy-3-[2-(2-(S)-methoxy-1-methylethylamino)-pyrimidin-4-yl]-6,7-dihydro-5H-pyrazolo[1,2-a]pyrazol-1-one (51): 2-(4-Fluorophenyl)-6-methoxy-3-(2-methanesulfonyl-pyrimidin-4-yl)-6,7-dihydro-5H-pyrazolo[1,2-a]pyrazol-1-one admixture, 50, (948 mg, 2.44 mmol) and (S)-2-amino-1-methoxypropane (652 mg, 7.32 mmol) is diluted with toluene (16 mL). The mixture is heated to 120° C. for 2 hours. The orange solution is allowed to cool to room temperature prior to concentration in vacuo to give an orange residue. The crude product is purified over silica (5% to 10% methyl alcohol/dichloro-methane) to afford 550 mg of the desired product as a fluorescent yellow solid. $^1$H NMR (300 MHz, CDCl$_3$) δ 8.16 (d, J=5.1 Hz, 1H), 7.40 (dd, J=8.8, 5.5 Hz, 2H), 7.03 (t, J=8.8 Hz, 2H), 6.39 (d, J=5.1 Hz, 1H), 5.39 (br d, J=8.0 Hz, 1H), 4.57 (m, 1H), 4.30–4.02 (m, 5H), 3.45 (d, J=4.6 Hz, 2H), 3.42 (s, 3H), 3.39 (s, 3H), 1.28 (d, J=6.6 Hz, 3H); HRMS m/z calcd for $C_{21}H_{25}FN_5O_3$ (MH$^+$) 414.1941, found 414.1945.

Using intermediate 10, which comprises a 6-methylene unit, the following analog can be prepared using the same procedures as outlined herein above:

2-(4-fluorophenyl)-6-methylene-3-[2-(2-(S)-phenyl-1-methylethylamino)-pyrimidin-4-yl]-6,7-dihydro-5H-pyrazolo[1,2-a]pyrazol-1-one, 52; $^1$H NMR (CDCl$_3$,300 MHz)☐ 1.60 (d, 3H, J=6.9 Hz), 4.52 (dd, 2H, J=15.9, 24 Hz), 5.08–5.15 (m, 2H), 5.26 (s, 1H), 6.03 (s, 1H), 6.38 (d, 1H, J=5.1 Hz), 7.00–7.05 (m, 2H), 7.22–7.42 (m, 8H), 8.16 (d, 1H, J=5.1 Hz). HRMS: Exact Mass $C_{25}H_{22}FN_5O$ 428.1887 (M$^+$+H), found 428.1871.

Intermediate 10 can also be oxidized under standard conditions, according to the scheme herein below, using OsO$_4$ to afford the intermediate, 53:

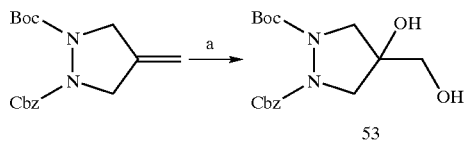

which can be used to prepare the following:

2-(4-Fluorophenyl)-6-hydroxy-6-hydroxymethyl-3-(2-phenoxypyrimidin-4-yl)-6,7-dihydro-5H-pyrazolo[1,2-a]pyrazol-1-one, 54; $^1$H NMR (DMSO-d$_6$, 300 MHz) ☐ 3.41–3.52 (m, 2H), 3.72–3.86 (m, 3H), 3.94 (d, 1H, J=11.1 Hz), 5.23 (t, 1H, J=5.7 Hz), 5.71 (s, 1H), 7.06 (d, 1H, J=4.8 Hz), 7.18–7.34 (m, 5H), 7.40–7.50 (m, 4H), 8.69 (d, 1H, J=4.8 Hz). ESI$^-$MS: m/z (rel intensity) 435.32 (100, M$^+$+H) Anal. Calculated for $C_{23}H_{19}FN_4O_4$ 0.5H2O: C, 62.30; H, 4.55: N, 12.63. Found: C, 62.33; H, 4.13; N, 12.41.

Other compounds of the present invention which can be prepared by the procedures or modifications thereof disclosed herein above include the following.

2-(3-trifluoromethylphenyl)-3-(2-phenoxy-pyrimidin-4-yl)-6,7-dihydro-5H-pyrazolo-[1,2-a]pyrazol-1-one;

2-(4-fluorophenyl)-3-(2-(6-aminopyrimidin-4-yloxy) pyrimidin-4-yl)-6,7dihydro-5H-pyrazolo-[1,2-a] pyrazol-1-one;

2-(4-fluorophenyl)-3-[2-(3-fluorophenoxy)pyrimidin-4-yl)-6,7-dihydro-5H-pyrazolo-[1,2-a]pyrazol-1-one;

2-(4-fluorophenyl)-3-[2-(2,4-dimethylphenoxy) pyrimidin-4-yl)-6,7 dihydro-5H-pyrazolo-[1,2-a] pyrazol-1-one;

2-(2,4-difluorophenyl)-3-(2-phenoxy-pyrimidin-4-yl)-6,7-dihydro-5H-pyrazolo-[1,2-a]pyrazol-1-one;

2-(4-fluorophenyl)-3-[2-(4-chlorophenoxy)pyrimidin-4-yl)-6,7-dihydro-5H-pyrazolo-[1,2-a]pyrazol-1-one 2-(4-Fluorophenyl)-3-{2-[1-(R,S)-(4-fluorophenyl) ethylamino]pyrimidin-4-yl}-6,7-dihydro-5H-pyrazolo[1,2-a]pyrazol-1-one;

2-{4-[2-(4-Fluorophenyl )-3-oxo-6,7-dihydro-3H,5H-pyrazolo[1,2-a]pyrazol-1yl]-pyrimidin-2-ylamino}-propionic acid;

2-{4-[2-(4-Fluorophenyl)-3-oxo-6,7-dihydro-3H,5H-pyrazolo[1,2-a]pyrazol-1-yl]-pyrimidin-2-ylamino}-N,N-dimethyl propionamide;

2-(4-Fluorophenyl)-3-(2-([1,3,4]thiadiazol-2-ylamino) pyrimidin-4-yl)-6,7-dihydro-5H-pyrazolo[1,2-a] pyrazol-1-one;

2-(4-Fluorophenyl)-3-{2-[(pyridin-2-ylmethyl)amino] pyrimidin-4-yl]-6,7-dihydro-5H-pyrazolo[1,2-a] pyrazol-1-one;

2-(4-Fluorophenyl)-3-[(2-methoxypropylamino) pyrimidin-4-yl]-6,7-dihydro-5H-pyrazolo[1,2-a] pyrazol-1-one;

2-(4-Fluorophenyl)-3-{2-[(furan-2-ylmethyl)amino] pyrimidin-4-yl]-6,7-dihydro-5H-pyrazolo[1,2-a] pyrazol-1-one;

2-(4-Fluorophenyl)-3-{2-[(3-benzo[1,3]dioxol-5-yl) amino]pyrimidin-4-yl]-6,7-5H-pyrazolo[1,2-a] pyrazol-1-one;

2-(4-Fluorophenyl)-3-{2-[(1-(propane-1-sulfonyl) piperidin-4-ylamino]pyrimidin-4-yl]-6,7-dihydro-5H-pyrazolo[1,2-a]pyrazol-1-one; and 2-(4-Fluorophenyl)-3-{2-(4-methoxybenzylamino) amino]-pyrimidin-4-yl]-6,7-dihydro-5H-pyrazolo[1,2-a]pyrazol-1-one.

Category IV of the inflammatory cytokine release inhibiting compounds according to the present invention have the general scaffold having the formula:

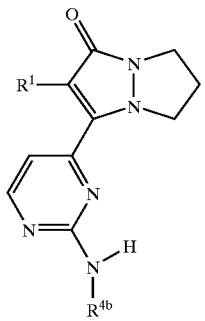

the first aspect of which relates to compounds having the $R^1$ and $R^{4b}$ units as defined herein below in TABLE IX.

TABLE IX

| No. | $R^1$ | $R^4$ |
| --- | --- | --- |
| 351 | 4-fluorophenyl | phenyl |
| 352 | 4-fluorophenyl | 2-fluorophenyl |
| 353 | 4-fluorophenyl | 3-fluorophenyl |
| 354 | 4-fluorophenyl | 4-fluorophenyl |
| 355 | 4-fluorophenyl | 2-chlorophenyl |
| 356 | 4-fluorophenyl | 3-chlorophenyl |
| 357 | 4-fluorophenyl | 4-chlorophenyl |
| 358 | 4-fluorophenyl | 2,4-difluorophenyl |
| 359 | 4-fluorophenyl | 2,6-difluorophenyl |
| 360 | 4-fluorophenyl | 3,5-difluorophenyl |
| 361 | 4-fluorophenyl | 2,4,6-trifluorophenyl |
| 362 | 4-fluorophenyl | 2,4-dichlorophenyl |
| 363 | 4-fluorophenyl | 2,6-dichlorophenyl |
| 364 | 4-fluorophenyl | 3,5-dichlorophenyl |
| 365 | 4-fluorophenyl | 2,4,6-trichlorophenyl |
| 366 | 4-fluorophenyl | naphthylen-1-yl |
| 367 | 4-fluorophenyl | naphthylen-2-yl |
| 368 | 4-fluorophenyl | 2-aminophenyl |
| 369 | 4-fluorophenyl | 3-aminophenyl |
| 370 | 4-fluorophenyl | 4-aminophenyl |
| 371 | 4-fluorophenyl | 2-cyanophenyl |
| 372 | 4-fluorophenyl | 3-cyanophenyl |
| 373 | 4-fluorophenyl | 4-cyanophenyl |
| 374 | 4-fluorophenyl | 2-methylphenyl |
| 375 | 4-fluorophenyl | 3-methylphenyl |
| 376 | 4-fluorophenyl | 4-methylphenyl |
| 377 | 4-fluorophenyl | 2-methoxyphenyl |
| 378 | 4-fluorophenyl | 3-methoxyphenyl |
| 379 | 4-fluorophenyl | 4-methoxyphenyl |
| 380 | 4-fluorophenyl | 2-methoxyphenoxy |
| 381 | 4-fluorophenyl | 4-methoxyphenoxy |
| 382 | 4-fluorophenyl | 2-(N-acylamino)phenyl |
| 383 | 4-fluorophenyl | 3-(N-acylamino)phenyl |
| 384 | 4-fluorophenyl | 4-(N-acylamino)phenyl |
| 385 | 4-fluorophenyl | 4-(methanesulfonyl)phenyl |
| 386 | 4-fluorophenyl | 4-(ethanesulfonyl)phenyl |
| 387 | 4-fluorophenyl | 4-(propanesulfonyl)phenyl |
| 388 | 4-fluorophenyl | 2-trifluoromethylphenyl |
| 389 | 4-fluorophenyl | 3-trifluoromethylphenyl |
| 390 | 4-fluorophenyl | 4-trifluoromethylphenyl |
| 391 | 4-fluorophenyl | 3,5-bis(trifluoromethyl)phenyl |
| 392 | 4-fluorophenyl | 3-benzo[1,3]dioxol-5-yl |
| 393 | 3-trifluomethylphenyl | phenyl |
| 394 | 3-trifluomethylphenyl | 2-fluorophenyl |
| 395 | 3-trifluomethylphenyl | 3-fluorophenyl |
| 396 | 3-trifluomethylphenyl | 4-fluorophenyl |
| 397 | 3-trifluomethylphenyl | 2-chlorophenyl |
| 398 | 3-trifluomethylphenyl | 3-chlorophenyl |
| 399 | 3-trifluomethylphenyl | 4-chlorophenyl |
| 400 | 3-trifluomethylphenyl | 2,4-difluorophenyl |
| 401 | 3-trifluomethylphenyl | 2,6-difluorophenyl |

TABLE IX-continued

| No. | $R^1$ | $R^4$ |
| --- | --- | --- |
| 402 | 3-trifluomethylphenyl | 3,5-difluorophenyl |
| 403 | 3-trifluomethylphenyl | 2,4,6-trifluorophenyl |
| 404 | 3-trifluomethylphenyl | 2,4-dichlorophenyl |
| 405 | 3-trifluomethylphenyl | 2,6-dichlorophenyl |
| 406 | 3-trifluomethylphenyl | 3,5-dichlorophenyl |
| 407 | 3-trifluomethylphenyl | 2,4,6-trichlorophenyl |
| 408 | 3-trifluomethylphenyl | naphthylen-1-yl |
| 409 | 3-trifluomethylphenyl | naphthylen-2-yl |
| 410 | 3-trifluomethylphenyl | 2-aminophenyl |
| 411 | 3-trifluomethylphenyl | 3-aminophenyl |
| 412 | 3-trifluomethylphenyl | 4-aminophenyl |
| 413 | 3-trifluomethylphenyl | 2-cyanophenyl |
| 414 | 3-trifluomethylphenyl | 3-cyanophenyl |
| 415 | 3-trifluomethylphenyl | 4-cyanophenyl |
| 416 | 3-trifluomethylphenyl | 2-methylphenyl |
| 417 | 3-trifluomethylphenyl | 3-methylphenyl |
| 418 | 3-trifluomethylphenyl | 4-methylphenyl |
| 419 | 3-trifluomethylphenyl | 2-methoxyphenyl |
| 420 | 3-trifluomethylphenyl | 3-methoxyphenyl |
| 421 | 3-trifluomethylphenyl | 4-methoxyphenyl |
| 422 | 3-trifluomethylphenyl | 2-methoxyphenoxy |
| 423 | 3-trifluomethylphenyl | 4-methoxyphenoxy |
| 424 | 3-trifluomethylphenyl | 2-(N-acylamino)phenyl |
| 425 | 3-trifluomethylphenyl | 3-(N-acylamino)phenyl |
| 426 | 3-trifluomethylphenyl | 4-(N-acylamino)phenyl |
| 427 | 3-trifluomethylphenyl | 4-(methanesulfonyl)phenyl |
| 428 | 3-trifluomethylphenyl | 4-(ethanesulfonyl)phenyl |
| 429 | 3-trifluomethylphenyl | 4-(propanesulfonyl)phenyl |
| 430 | 3-trifluomethylphenyl | 2-trifluoromethylphenyl |
| 431 | 3-trifluomethylphenyl | 3-trifluoromethylphenyl |
| 432 | 3-trifluomethylphenyl | 4-trifluoromethylphenyl |
| 433 | 3-trifluomethylphenyl | 3,5-bis(trifluoromethyl)phenyl |
| 434 | 3-trifluomethylphenyl | 3-benzo[1,3]dioxol-5-yl |

The compounds which comprise the first aspect of the Category IV compounds can be prepared by the scheme outline below utilizing intermediate 5 as a convenient starting material.

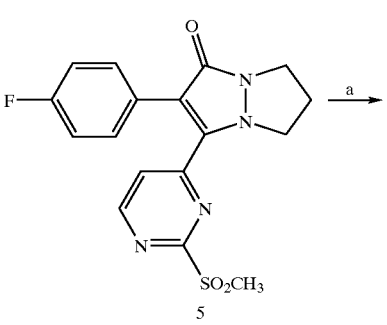

-continued

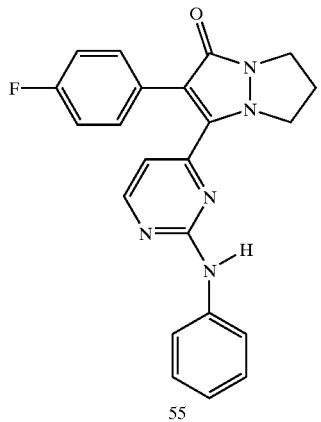

Reagents and conditions: (a) aniline, NaH, THF; reflux 1 hr.

EXAMPLE 14

2-(4-Fluoro-phenyl)-3-(2-phenylamino-pyrimidin-4-yl)-6,7-dihydro-5H-pyrazolo-[1,2-a]pyrazol-1-one (2)

Preparation of 2-(4-fluoro-phenyl)-3-(2-phenylamino-pyrimidin-4-yl)-6,7-dihydro-5H-pyrazolo[1,2-a]pyrimidin-1-one (55): To a solution of aniline (0.12 mL, 1.34 mmol) in THF (4 mL) is added NaH (0.07 g, 1.00 mmol). After stirring the mixture for 5 min at room temperature, 2-(4-fluorophenyl)-3-(2-methanesulfonyl-pyrimidin-4-yl)-6,7dihydro-5H-pyrazolo[1,2-a]pyrazol-1-one, 5, (0.25 g, 0.67 mmol) is added to the reaction mixture. The reaction mixture is heated to reflux and stirred for 1 h. The mixture is diluted with aqueous saturated $NH_4Cl$ and extracted with twice with chloroform. The organic layers are combined, dried over $MgSO_4$, and concentrated in vacuo to afford the crude product that is purified over silica (5% MeOH/chloroform) to provide 0.05 g (20% yield) of the desired product as a yellow solid. $^1H$ NMR (300 MHz, $CDCl_3$) □ 8.34 (d, J=5.1 Hz, 1H), 7.57 (dd, J=8.7, 1.2 Hz, 2H), 7.47–7.29 (m, 4H), 7.16–7.05 (m, 3H), 6.62 (d, J=5.1 Hz, 1H), 4.11 (t, J=6.9 Hz, 2H), 4.06 (t, J=6.9 Hz, 2H), 2.70 (dddd, J=6.9, 6.9, 6.9, 6.9 Hz, 2H). $ESI^+$ MS m/z (rel intensity) 388.1 (100, $M^++H$). Anal. Calculated for $C_{22}H_{18}FN_5O$ $0.5H_2O$: C, 66.66; H, 4.83; N, 17.67. Found: C, 66.55; H, 4.49; N, 17.39. This compound corresponds to analog 351 from Table IX.

The following compounds from the first aspect of Category IV can be prepared by the procedure described herein above.

3-[2-(2,6-Difluoro-phenylamino)-pyrimidin-4-yl]-2-(4-fluoro-phenyl)-6,7-dihydro-5H-pyrazolo[1,2-a]pyrazol-1-one: $^1H$ NMR (300 MHz, $d_6$-DMSO) □ 9.36 (s, NH), 8.38 (d, J=5.1 Hz, 1H),7.40–7.33 (m, 3H), 7.21–7.11 (m, 4H), 6.58 (d, J=5.1 Hz, 1H), 3.90–3.82 (m, 4H), 2.55–2.51(m, 2H). $ESI^+$ MS m/z (rel intensity) 424.1 (100, $M^++H$). Anal. Calculated for $C_{22}H_{16}F_3N_5O$ $0.5H_2O$: C, 61.11; H, 3.96; N, 16.20. Found: C, 61.67; H. 4.03; N, 15.73.

3-[2(2,6-Dichloro-phenylamino)-pyrimidin-4-yl]-2-(4-fluoro-phenyl)-6,7-dihydro-5H-pyrazolo[1,2-a]pyrazol-1-one: $^1H$ NMR (300 MHz, $CDCl_3$) □ 8.32 (d, J=5.1 Hz, 1H), 7.47 (d, J=8.1 Hz, 2H), 7.41 (dd, J=8.7, 5.4 Hz, 2H), 7.29–7.25 (m, 1H), 7.08 (t, J=8.7 Hz, 2H), 6.93 (bd s, NH), 6.64 (d, J=5.1 Hz, 1H), 4.06 (t, J=6.9 Hz, 2H), 3.93 (t, J=6.9 Hz, 2H), 2.61 (dddd, J=6.9, 6.9, 6.9, 6.9 Hz, 2H). $ESI^+$MS m/z (rel intensity) 433.1 (100, $M^++H$). Anal. Calculated for $C_{22}H_{16}FCl_2N_5O$ $0.5H_2O$: C, 56.79; H, 3.68; N, 15.05. Found: C, 56.50; H, 3.63; N, 14.59.

2-(4-Fluoro-phenyl)-3-[2-(pyridin-2-ylamino)-pyrimidin-4-yl]-6,7-dihydro-5H-pyrazolo[1,2-a]pyrazol-1-one: $^1H$ NMR (300 MHz, $CDCl_3$) □ 8.46 (d, J=5.1 Hz, 1H). 8.38–8.36 (m, 2H), 8.22 (d, J=8.7 Hz, 1H), 7.69 (ddd, J=9.0, 7.5, 1.8 Hz, 1H), 7.45 (dd, J=8.7, 5.4 Hz, 2H), 7.07 (dd, J=8.7, 8.7 Hz, 2H), 7.02–6.98 (m, 1H), 6.72 (d, J=5.1 Hz, 1H), 4.09 (t, J=6.9 Hz, 2H), 4.06 (t, J=6.9 Hz, 2H), 2.73 (dddd, J=6.9, 6.9, 6.9, 6.9 Hz, 2H). $ESI^+$ MS m/z (rel intensity) 389.1 (70, $M^++H$). Anal. Calculated for $C_{21}H_{17}FN_6O$ $H_2O$: C, 62.06; H, 4.71; N, 20.68. Found: C, 61.77; H, 4.26; N, 20.05.

The second aspect of which relates to compounds having the $R^1$ and $R^{4b}$ units as defined herein below in Table IX.

TABLE X

| No. | $R^1$ | $R^4$ |
|---|---|---|
| 435 | 4-fluorophenyl | pyridin-2-yl |
| 436 | 4-fluorophenyl | pyridin-3-yl |
| 437 | 4-fluorophenyl | pyridin-4-yl |
| 438 | 4-fluorophenyl | pyrimidin-2-yl |
| 439 | 4-fluorophenyl | pyrimidin-4-yl |
| 440 | 4-fluorophenyl | pyrimidin-5-yl |
| 441 | 4-fluorophenyl | 4,6-dichloropyrimidin-5-yl |
| 442 | 4-fluorophenyl | s-triazinyl |
| 443 | 3-trifluomethylphenyl | pyridin-2-yl |
| 444 | 3-trifluomethylphenyl | pyridin-3-yl |
| 445 | 3-trifluomethylphenyl | pyridin-4-yl |
| 446 | 3-trifluomethylphenyl | pyrimidin-2-yl |
| 447 | 3-trifluomethylphenyl | pyrimidin-4-yl |
| 448 | 3-trifluomethylphenyl | pyrimidin-5-yl |
| 449 | 3-trifluomethylphenyl | 4,6-dichloropyrimidin-5-yl |
| 450 | 3-trifluomethylphenyl | s-triazinyl |

The compounds which comprise the second aspect of the Category IV compounds can be prepared by the scheme outline below utilizing intermediate 5 as a convenient starting material.

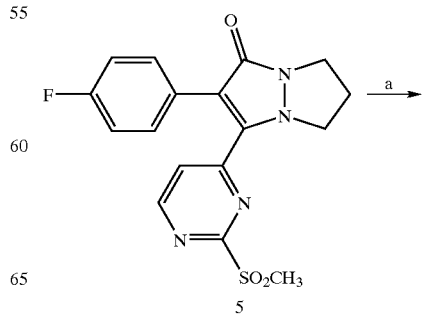

-continued

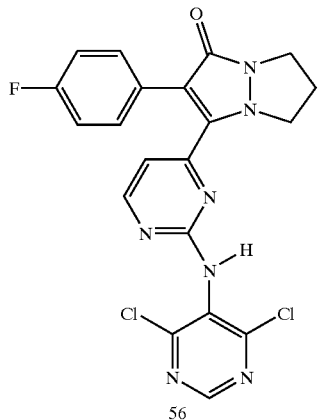

56

Reagents and conditions: (a) 5-amino-4,6-dichloropyrimidine, NaH, THF; reflux 1 hr.

EXAMPLE 15

3-[2-(4,6-Dichloro-pyrimidin-5-ylamino)-pyrimidin-4-yl]-2-(4-fluoro-phenyl)-6,7-dihydro-5H-pyrazolo[1,2-a]pyrazol-1-one (56)

Preparation of 3-[2-(4,6-dichloro-pyrimidin-5-ylamino)-pyrimidin-4-yl]-2-(4-fluoro-phenyl)-6,7-dihydro-5H-pyrazolo[1,2-a]pyrazol-1-one (56): To a solution of 5-amino-4,6-dichloropyrimidine (219 mg, 1.34 mmol) in THF (4 mL) is added NaH (0.07 g, 1.00 mmol). After stirring the mixture for 5 min at room temperature, 2-(4-fluorophenyl)-3-(2-methanesulfonyl-pyrimidin-4-yl)-6,7-dihydro-5H-pyrazolo[1,2-a]pyrazol-1-one, 5, (0.25 g, 0.67 mmol) is added to the reaction mixture. The reaction mixture is heated to reflux and stirred for 1 h. The mixture is diluted with aqueous saturated $NH_4Cl$ and extracted with twice with chloroform. The organic layers are combined, dried over $MgSO_4$, and concentrated in vacuo to afford the crude product that is purified over silica (5% MeOH/chloroform) to provide the desired product as a yellow solid. $^1H$ NMR (300 MHz, $CDCl_3$) $\square$ 8.77 (s, 1H), 8.35 (d, J=5.1 Hz, 1H), 7.35 (dd, J=9.0, 5.1 Hz, 1H), 7.10 (dd, J=8.7, 8.7 Hz, 2H), 6.71 (d, J=5.1 Hz, 1H), 4.25 (t, J=6.9 Hz, 2H), 4.12 (t, J=6.9 Hz, 2H), 2.74 (dddd, J=6.9, 6.9, 6.9, 6.9 Hz, 2H). $ESI^+$ MS m/z (rel intensity) 458.1 (100, $M^++H$). This compound corresponds to analog 441 from Table X.

The analogs (compounds) of the present invention are arranged in several categories to assist the formulator in applying a rational synthetic strategy for the preparation of analogs which are not expressly exampled herein. The arrangement into categories does not imply increased or decreased efficacy for any of the compositions of matter described herein.

Compounds listed and described herein above have been found in many instances to exhibit activities ($IC_{50}$ in the cell based assay described herein below or ones which are referenced herein) at a level below 1 micromolar ($\square M$).

The compounds of the present invention are capable of effectively blocking the production of inflammatory cytokine production from cells, which thereby allows for the mitigation, alleviation, control, abatement, retardation, or prevention of one or more disease states or syndromes which are related to the extracellular release of one or more cytokines. Inflammatory disease states include those which are related to the following non-limiting examples:

i) Interleukin-1 (IL-1): implicated as the molecule responsible for a large number of disease states, inter alia, rheumatoid arthritis, osteoarthritis, as well as other disease stales which relate to connective tissue degradation.

ii) Cycloxygenase-2 (COX-2): inhibitors of cytokine release are proposed as inhibitors of inducible COX-2 expression, which has been shown to be increased by cytokines. M. K. O'Banion et al., *Proc. Natl. Acad. Sci. U.S.A.*, 89, 4888 (1998).

iii) Tumor Necrosis Factor-$\square$ (TNF-$\square$): This pro-inflammatory cylokine is suggested as an important mediator in many disease states or syndromes, inter alia, rheumatoid arthritis, osteoarthritis, inflammatory bowel disease (IBS), septic shock, cardiopulmonary dysfunction, acute respiratory disease, and cachexia.

Each of the disease states or conditions which the formulator desires to treat may require differing levels or amounts of the compounds described herein to obtain a therapeutic level. The formulator can determine this amount by any of the known testing procedures known to the artisan.

The present invention further relates to forms of the present compounds, which under normal human or higher mammalian physiological conditions, release the compounds described herein. One iteration of this aspect includes the pharmaceutically acceptable salts of the analogs described herein. The formulator, for (he purposes of compatibility with delivery mode, excipients, and the like, can select one salt form of the present analogs over another since the compounds themselves are the active species which mitigate the disease processes described herein.

Related to this aspect are the various precursor of "pro-drug" forms of the analogs of the present invention. It may be desirable to formulate the compounds of the present invention as a chemical species which itself is not active against the cytokine activity described herein, but instead are forms of the present analogs which when delivered to the body of a human or higher mammal will undergo a chemical reaction catalyzed by the normal function of the body, inter alia, enzymes present in the stomach, blood serum, said chemical reaction releasing the parent analog. The term "pro-drug" relates to these species which are convened in vivo to the active pharmaceutical.

FORMULATIONS

The present invention also relates to compositions or formulations which comprise the inflammatory cytokine release-inhibiting compounds according to the present invention. In general, the compositions of the present invention comprise:

a) an effective amount of one or more bicyclic pyrazolones and derivatives thereof according to the present invention which are effective for inhibiting release of inflammatory cytokines; and b) one or more pharmaceutically acceptable excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient.

An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present invention also relates to compositions or formulations which comprise a precursor or "pro-drug" form of the inflammatory cylokine release-inhibiting compounds according to the present invention. In general, these precursor-comprising compositions of the present invention comprise:

a) an effective amount of one or more derivatives of bicyclic pyrazolones according to the present invention which act to release in vivo the corresponding analog which is effective for inhibiting release of inflammatory cytokines; and b) one or more pharmaceutically acceptable excipients.

Method of use

The present invention also relates to a method for controlling the level of one or more inflammation inducing cytokines, inter alia, interleukin-1 (IL-1), Tumor Necrosis Factor-□ (TNF-□), interleukin-6 (IL-6), and interleukin-8 (IL-8) and thereby controlling, mediating, or abating disease states affected by the levels of extracellular inflammatory cytokines. The present method comprises the step of administering to a human or higher mammal an effective amount of a composition comprising one or more of the inflammatory cytokine inhibitors according to the present invention.

Because the inflammatory cytokine inhibitors of the present invention can be delivered in a manner wherein more than one site of control can be achieved, more than one disease state can be modulated at the same time. Non-limiting examples of diseases which are affected by control or inhibition of inflammatory cytokine inhibitors, thereby modulating excessive cytokine activity, include osteoarthritis, rheumatoid arthritis, diabetes, human Immunodeficiency virus (HIV) infection.

Procedures

The compounds of the present invention can be evaluated for efficacy, for example, measurements of cytokine inhibition constants, $K_i$, and $IC_{50}$ values can be obtained by any method chosen by the formulator.

Non-limiting examples of suitable assays include:

i) UV-visible substrate enzyme assay as described by L. Al Reiter, *Int. J. Peptide Protein Res.*, 43, 87–96 (1994).

ii) Fluorescent substrate enzyme assay as described by Thornberry et al., *Nature*, 356, 768–774 (1992).

iii) PBMC Cell assay as described in U.S. Pat. No. 6,204,261 B1 Batchelor et al., issued Mar. 20, 2001.

Each of the above citations is included herein by reference.

In addition, Tumor Necrosis Factor, TNF-□, inhibition can be measured by utilizing lipopolysaccharide (LPS) stimulated human monocytic cells (THP-1) as described in:

i) K. M. Mohler et al., "Protection Against a Lethal Dose of Endotoxin by an Inhibitor of Tumour Necrosis Factor Processing", *Nature*, 370, pp 218–220 (1994).

ii) U.S. Pat. No. 6,297,381 B1 Cirillo et al., issued Oct. 2, 2001, incorporated by reference and reproduced herein below in relevant portion thereof.

The inhibition of cytokine production can be observed by measuring inhibition of TNF-□ in lipopolysaccharide stimulated THP cells. All cells and reagents are diluted in RPMI 1640 with phenol red and L-glutamine, supplemented with additional L-glutamine (total: 4 mM), penicillin and streptomycin (50 units/mL each) and fetal bovine serum (FBS 3%) (GIBCO, all conc. Final). Assay is performed under sterile conditions, only test compound preparation is non-sterile. Initial stock solutions are made in DMSO followed by dilution into RPMI 1640 2-fold higher than the desired final assay concentration. Confluent THP.1 cells ($2\times10^6$ cells/mL, final conc.; American Type Culture Company, Rockville, Md.) are added to 96 well polypropylene round bottomed culture plates (Costar 3790; sterile) containing 125 □L test compound (2-fold concentrated) or DMSO vehicle (controls, blanks). DMSO concentration should not exceed 0.2% final. Cell mixture is allowed to preincubate for 30 minutes at 37° C., 5% $CO_2$ prior to stimulation with lipopolysaccharide (LPS, 1 □g/mL final; Sigma L-2630, from *E. coli* serotype 0111.B4; stored as 1 mg/mL stock in endotoxin screened diluted $H_2O$ vehicle at −80° C.). Blanks (unstimulated) receive $H_2O$ vehicle; final incubation volume is 250 □L. Incubation (4 hours) proceeds as described above. Assay is to be terminated by centrifuging plates 5 minutes at room temperature, 1600 rpm (4033 g); supernatants are then transferred to clean 96 well plates and stored at −80° C. until analyzed for human TNF-□ by a commercially available ELISA kit (Biosource #KHC3015, Camarillo, Calif.). The calculated $IC_{50}$ value is the concentration of the test compound that caused a 50% decrease in the maximal TNF-□ production.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound, including all enantiomeric and diasteriomeric forms and pharmaceutically acceptable salts thereof, said compound having the formula:

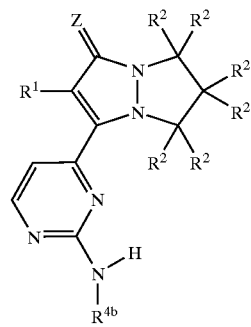

wherein $R^1$ is:
a) substituted or unsubstituted aryl; or
b) substituted or unsubstituted heteroaryl;

each $R^2$ unit is independently selected from the group consisting of:
a) hydrogen;
b) —$(CH_2)_jO(CH_2)_nR^8$;
c) —$(CH_2)_jNR^{9a}R^{9b}$;
d) —$(CH_2)_jCO_2R^{10}$;
e) —$(CH_2)_jOCO_2R^{10}$ f) —(CH2)$_j$CON(R$^{10}$)$_2$;
g) —(CH$_2$)$_j$OCON(R$^{10}$)$_2$;
h) two R$^2$ units can be taken together to form a carbonyl unit;
i) and mixtures thereof;

R$^8$, R$^{9a}$, R$^{9b}$, and R$^{10}$ are each independently hydrogen, C$_1$–C$_4$ alkyl, and mixtures thereof;

R$^{9a}$ and R$^{9b}$ can be taken together to form a carbocyclic or heterocyclic ring comprising from 3 to 7 atoms; two R$^{10}$ units can be take together to form a carbocyclic or heterocyclic ring comprising from 3 to 7 atoms; j is an index from 0 to 5, n is an index from 0 to 5;

Z is O, S, NR$^{11}$, or NOR$^{11}$; R$^{11}$ is hydrogen or C$_1$–C$_4$ alkyl

R$^{4b}$ is substituted or unsubstituted aryl or substituted or unsubstituted heteroaryl.

2. A compound according to claim 1 having the formula:

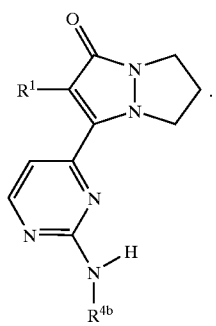

3. A compound according to claim 2 wherein R$^1$ is 4-fluorophenyl, 3-fluorophenyl, 2,4-difluorophenyl, 4-chlorophenyl, 3-chlorophenyl, 2,4-chlorophenyl, or 3-trifluorophenyl.

4. A compound according to claim 3 wherein R$^1$ is 4-fluorophenyl.

5. A compound according to claim 2 wherein R$^{4b}$ is an aryl unit or halogen substituted aryl unit selected from the group consisting of phenyl, 2-fluorophenyl, 3-fluorophenyl, 4-fluorophenyl, 2,4-difluorophenyl, 2,6-difluorophenyl, 3,5-difluorophenyl, 2,4,6-trifluorophenyl, 2-chlorophenyl, 3-chlorophenyl, 4-chlorophenyl, 2,4-dichlorophenyl, 2,6dichlorophenyl, 3,5-dichlorophenyl, 2,4,6-trichlorophenyl, naphthylen-1-yl, and naphthylen-2-yl.

6. A compound according to claim 2 wherein R$^{4b}$ is a substituted aryl unit selected from the group consisting of 2-aminophenyl, 3-aminophenyl, 4-aminophenyl, 2-methylphenyl, 3-methylphenyl, 4-methylphenyl, 2,4dimethylphenyl, 2-methoxyphenyl, 3-methoxyphenyl, 4-methoxyphenyl, 2-cyanophenyl, 3-cyanophenyl, and 4-cyanophenyl.

7. A compound according to claim 2 wherein R$^{4b}$ is a substituted aryl unit selected from the group consisting of 4-(methanesulfonyl)phenyl, 4-(ethanesulfonyl)phenyl 4-(propane-sulfonyl)phenyl, 2-(N-acylamino)phenyl, 3-(N-acylamino)phenyl, 4-(N-acylamino)phenyl, and 3-benzo[1,3]dioxol-5-yl.

8. A compound according to claim 2 wherein R$^{4b}$ is an aryl unit selected from the group consisting of 2-trifluoromethylphenyl, 3-trifluoromethylphenyl, 4-trifluoromethylphenyl, and 3,5-bis(trifluoromethyl)phenyl.

9. A compound according to claim 2 wherein R$^{4b}$ is a heteroaryl or substituted heteroaryl unit selected from the group consisting of pyridin-2-yl, pyridin-3-yl, pyridin-4-yl, pyrimidin-2-yl, pyrimidin-4-yl, pyrimidin-5-yl, 4,6-dichloropyrimidin-5-yl, and 5-triazinyl.

10. A compound, including all enantiomeric and diasteriomeric forms and pharmaceutically acceptable salts thereof, said compound having the formula:

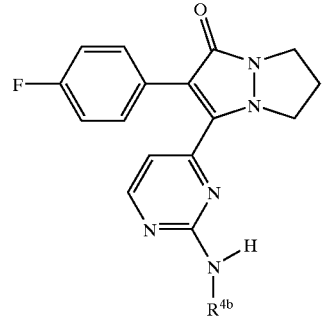

wherein R$^{4b}$ is substituted or unsubstituted aryl or substituted or unsubstituted heteroaryl.

11. A compound according to claim 10 wherein said aryl or substituted aryl unit is phenyl or naphthyl.

12. A compound according to claim 11 wherein said aryl or substituted aryl unit is selected from the group consisting of phenyl, 2-fluorophenyl, 3-fluorophenyl, 4-fluorophenyl, 2,6-difluorophenyl, 2,6-dichlorophenyl, 3-cyanophenyl, 2,4-dimethylphenyl, 3-trifluoromethyl-phenyl, 4-trifluoromethylphenyl, 4-methylphenyl, 4-methoxyphenyl, and 3-benzo[1,3]-dioxol-5-yl.

13. A compound according to claim 11 wherein said heteroaryl or substituted heteroaryl unit is pyridinyl, pyrimidinyl, or triazinyl.

14. A compound according to claim 13 wherein said heteroaryl or substituted heteroaryl unit is selected from the group consisting of pyridin-2-yl, pyridin-3-yl, pyridin-4-yl, pyrimidin-2-yl, pyrimidin-4-yl, pyrimidin-5-yl, and 4,6-dichloropyrimidin-5-yl.

15. A compound according to claim 10 wherein R$^{4b}$ is phenyl, 2-fluorophenyl, 3-fluorophenyl, 4-fluorophenyl, 2,6-difluorophenyl, 2,6-dichlorophenyl, 3-cyanophenyl, 2,4-dimethylphenyl, 3-trifluoromethyl-phenyl, 4-trifluoromethylphenyl, 4-methylphenyl, 4-methoxyphenyl, 3-(N-acylamino)phenyl, 4,6dichloropyrimidin-5-yl, and 3-benzo[1,3]-dioxol-5-yl.

16. A compound, including all enantiomeric and diasteriomeric forms and pharmaceutically acceptable salts thereof, said compound selected from the group consisting of:

2-(4-Fluorophenyl)-3-(2-phenylamino-pyrimidin-4-yl)-6,7-dihydro-5H-pyrazolo[1,2-a]pyrazol-1-one;

3-[2-(2,6-Difluoro-phenylamino)-pyrimidin-4-yl]-2-(4-fluorophenyl)-6,7-dihydro-5H-pyrazolo[1,2-a]pyrazol-1-one;

3-[2-(2,6-Dichlorophenylamino)-pyrimidin-4-yl]-2-(4-fluorophenyl)-6,7-dihydro-5H-pyrazolo[1,2-a]pyrazol-1-one;

2-(4-Fluorophenyl)-3-[2-(pyridin-2-ylamino)-pyrimidin-4-yl]-6,7-dihydro-5H-pyrazolo[1,2-a]pyrazol-1-one; and 3-[2-(4,6-Dichloropyrimidin-5-ylamino)-pyrimidin-4-yl]-2-(4-fluoro-phenyl)-6,7-dihydro-5H-pyrazolo[1,2-a]pyrazol-1-one.

17. A pharmaceutical composition comprising:
a) an effective amount of one or more bicyclic pyrazolones including all enantiomeric and diasteriomeric forms and pharmaceutically acceptable salts thereof, said compound having the formula:

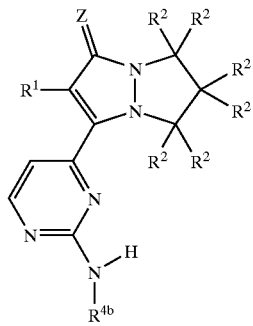

wherein $R^1$ is:
a) substituted or unsubstituted aryl; or
b) substituted or unsubstituted heteroaryl;
each $R^2$ unit is independently selected from the group consisting of:
a) hydrogen;
b) —$(CH_2)_jO(CH_2)_nR^8$;
c) —$(CH_2)_jNR^{9a}R^{9b}$;
d) —$(CH_2)_jCO_2R^{10}$;
e) —$(CH_2)_jOCO_2R^{10}$
f) —$(CH_2)_jCON(R^{10})_2$;
g) —$(CH_2)_jOCON(R^{10})_2$;
h) two $R^2$ units can be taken together to form a carbonyl unit;
i) and mixtures thereof;
$R^8$, $R^{9a}$, $R^{9b}$, and $R^{10}$ are each independently hydrogen, $C_1$–$C_4$ alkyl, and mixtures thereof; $R^{9a}$ and $R^{9b}$ can be taken together to form a carbocyclic or heterocyclic ring comprising from 3 to 7 atoms; two $R^{10}$ units can be take together to form a carbocyclic or heterocyclic ring comprising from 3 to 7 atoms; j is an index from 0 to 5, n is an index,from 0 to 5;
Z is O, S, $NR^{11}$, or $NOR^{11}$; $R^{11}$ is hydrogen or $C_1$-$C_4$ alkyl
$R^{4b}$ is substituted or unsubstituted aryl or substituted or unsubstituted heteroaryl; and
b) one or more pharmaceutically acceptable excipients.

* * * * *

UNITED STATES PATENT AND TRADEMARK OFFICE
CERTIFICATE OF CORRECTION

PATENT NO.        : 6,849,627 B2
APPLICATION NO.   : 10/390216
DATED             : February 1, 2005
INVENTOR(S)       : Clark et al.

It is certified that error appears in the above-identified patent and that said Letters Patent is hereby corrected as shown below:

Column 1
    Line 32, please delete "(1NF-" and insert -- (TNF- --.

Column 6
    Line 19, please delete "4cyanophenoxy" and insert -- 4-cyanophenoxy --.

Column 7
    Line 44, please delete "benzol_b1,3]" and insert -- benzol[1,3] --.

Column 8
    Line 31, please delete "D) K units" and insert -- D) R units --.

Column 12
    Line 38, please delete "4,6dicholoropyrimidin" and insert -- 4,6-dicholoropyrimidin --.
    Line 59, please delete "6,7dihydro" and insert -- 6,7-dihydro --.

Column 13
    Line 38, please delete "-5H-1-pyrazolo" and insert -- -5H-pyrazolo --.

Column 16
    Line 20, please delete "4dimethoxymethyl" and insert -- 4-dimethoxymethyl --.

Column 19
    Line 17, please delete "J=51 HZ" and insert -- J=5.1 Hz --.
    Line 25, please delete "(m, 2)," and insert -- (m, 2H) --.
    Line 32, please delete "J=5.1 HZ," and insert -- J=5.1Hz, --.
    Line 49, please delete "J=8.2 Hx" and insert -- J=8.2 Hz --.

Column 22
    Line 25, please delete "-}3H,5H-" and insert -- -3H,5H- --.
    Line 61, please delete "(m," and insert -- (m 2H) --.

Column 36
    Line 53, please delete "THF/H2O" and insert -- THF/$H_2O$ --.

UNITED STATES PATENT AND TRADEMARK OFFICE
CERTIFICATE OF CORRECTION

PATENT NO. : 6,849,627 B2
APPLICATION NO. : 10/390216
DATED : February 1, 2005
INVENTOR(S) : Clark et al.

It is certified that error appears in the above-identified patent and that said Letters Patent is hereby corrected as shown below:

Column 46
    Line 50, please add a line after hr. and insert -- EXAMPLE 11 --.

Column 47
    Line 59, please delete "category m" and insert -- Category III --.

Column 50
    Line 30, please delete "C. A S 5.0M" and insert -- C. A 5.0M --.

Column 54
    Line 59, please delete in the chemical structure "OCH$_3$" and insert -- OCH$_2$ --.

Column 58
    Line 17, please delete "0.5H2O" and insert -- 0.5H$_2$O --.

Column 61
    Line 29, please delete "2-a]pyrimidin-" and insert -- 2-a] pyrazol --.

Column 64
    Line 27, please delete "(he purposes of" and insert -- the purposes of --.

Column 68
    Line 2, please delete "5-triaziny" and insert -- *S*-triazinyl --.

Signed and Sealed this

Eighth Day of September, 2009

David J. Kappos
*Director of the United States Patent and Trademark Office*